United States Patent
Andersson et al.

(10) Patent No.: US 6,756,393 B2
(45) Date of Patent: Jun. 29, 2004

(54) AZACYCLIC COMPOUNDS

(75) Inventors: Carl-Magnus A. Andersson, Glostrup (DK); Glenn Croston, San Diego, CA (US); Eva L. Hansen, Glostrup (DK); Allan Kjaersgaard Uldam, Glostrup (DK)

(73) Assignee: Acadia Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 10/409,782

(22) Filed: Apr. 7, 2003

(65) Prior Publication Data

US 2003/0220316 A1 Nov. 27, 2003

Related U.S. Application Data

(63) Continuation of application No. 09/800,096, filed on Mar. 6, 2001.
(60) Provisional application No. 60/187,289, filed on Mar. 6, 2000.

(51) Int. Cl.$^7$ ............. A61K 31/44; C07D 211/00; C07D 211/56
(52) U.S. Cl. ............. 514/352; 514/183; 514/357; 514/358; 546/244; 546/246; 546/248
(58) Field of Search ............. 514/183, 352, 514/357, 358; 546/244, 246, 248

(56) References Cited

U.S. PATENT DOCUMENTS

| 4,853,394 A | 8/1989 | King et al. |
| 5,216,165 A | 6/1993 | Mobilio et al. |

FOREIGN PATENT DOCUMENTS

| EP | 0 260 070 | 3/1988 |
| EP | 0 625 507 | 7/1997 |
| WO | WO 94/27967 | 12/1994 |
| WO | 9738984 | * 10/1997 |
| WO | WO 98/50534 | 11/1998 |
| WO | 9850534 | * 11/1998 |
| WO | WO 00/23076 | 4/2000 |
| WO | WO 01/44191 | 6/2001 |
| WO | WO 01/87839 | 11/2001 |

OTHER PUBLICATIONS

Wade, et al., Application of Base Cleavable Safety Catch Linkers to Solid Phase Library Production, J. Comb. Chem. 2:266–275 (2000).

* cited by examiner

*Primary Examiner*—Mukund J. Shah
*Assistant Examiner*—Sudhaker B. Patel
(74) *Attorney, Agent, or Firm*—Knobbe Martens Olson & Bear LLP

(57) ABSTRACT

Compounds and methods are provided for the treatment of disease conditions in which modification of serotonergic receptor activity has a beneficial effect. In the method, an effective amount of a compound is adminstered to a patient in need of such treatment.

5 Claims, 4 Drawing Sheets

AZACYCLIC COMPOUNDS

This application is a continuation of U.S. patent application Ser. No. 09/800,096, entitled "AZACYCLIC COMPOUNDS," filed Mar. 6, 2001, by Anderson, et al., which in turn claims priority to U.S. Provisional Patent Serial No. 60/187,289, filed Mar. 6, 2000, all of which are incorporated by reference herein in their entirety, including any drawings,

FIELD OF THE INVENTION

The present invention relates to novel compounds that affect monoamine receptors, including serotonin receptors. The invention specifically provides compounds that are active as inverse agonists, and therefore also as antagonists, at the 5-HT2A subtype of human serotonin receptors. The invention also provides methods, utilizing the compounds of the invention for modulating 5-HT2A receptor-mediated events, that are useful for treating or alleviating disease conditions in which modification of the activity of these receptors is beneficial.

BACKGROUND OF THE INVENTION

Serotonin or 5-hydroxytryptamine (5-HT) plays a significant role in the functioning of the mammalian body. In the central nervous system, 5-HT is an important neurotransmitter and neuromodulator that is implicated in such diverse behaviors and responses as sleeping, eating, locomotion, perceiving pain, learning and memory, sexual behavior, controlling body temperature and blood pressure. In the spinal column, serotonin plays an important role in the control systems of the afferent peripheral nociceptors (Moulignier, Rev. Neurol. 150:3–15, (1994)). Peripheral functions in the cardiovascular, hematological and gastrointestinal systems have also been ascribed to 5-HT. 5-HT has been found to mediate a variety of contractile, secretory, and electrophysiologic effects including vascular and non-vascular smooth muscle contraction, and platelet aggregation. (Fuller, Biology of Serotonergic Transmission, 1982; Boullin, Serotonin In Mental Abnormalities 1:316 (1978); Barchas, et al., Serotonin and Behavior, (1973)). The 5-HT2A receptor subtype (also referred to as subclass) is widely yet discretely expressed in the human brain, including many cortical, limbic, and forebrain regions postulated to be involved in the modulation of higher cognitive and affective functions. This receptor subtype is also expressed on mature platelets where it mediates, in part, platelet aggregation, one of the initial steps in the process of vascular thrombosis.

Given the broad distribution of serotonin within the body, it is understandable that tremendous interest in drugs that affect serotonergic systems exists (Gershon, et al., The Peripheral Actions of 5-Hydroxytryptamine, 246 (1989); Saxena, et al., J. Cardiovascular Pharmacol. 15: Supp. 7 (1990)). Serotonin receptors are members of a large human gene family of membrane-spanning proteins that function as transducers of intercellular communication. They exist on the surface of various cell types, including neurons and platelets, where, upon their activation by either their endogenous ligand serotonin or exogenously administered drugs, they change their conformational structure and subsequently interact with downstream mediators of cellular signaling. Many of these receptors, including the 5-HT2A subclass, are G-protein coupled receptors (GPCRs) that signal by activating guanine nucleotide binding proteins (G-proteins), resulting in the generation, or inhibition of, second messenger molecules such as cyclic AMP, inositol phosphates, and diacylglycerol. These second messengers then modulate the function of a variety of intracellular enzymes, including kinases and ion channels, which ultimately affect cellular excitability and function.

At least 15 genetically distinct 5-HT receptor subtypes have been identified and assigned to one of seven families (5-HT1–7). Each subtype displays a unique distribution, preference for various ligands, and functional correlate(s).

Serotonin may be an important component in various types of pathological conditions such as certain psychiatric disorders (depression, aggressiveness, panic attacks, obsessive compulsive disorders, psychosis, schizophrenia, suicidal tendency), certain neurodegenerative disorders (Alzheimer-type dementia, Parkinsonism, Huntington's chorea), anorexia, bulimia, disorders associated with alcoholism, cerebral vascular accidents, and migraine (Meltzer, Neuropsychopharmacology, 21:106S–115S (1999); Barnes & Sharp, Neuropharmacology, 38:1083–1152 (1999); Glennon, Neurosci. Biobehavioral Rev., 14:35 (1990)). Recent evidence strongly implicates the 5-HT2 receptor subtype in the etiology of such medical conditions as hypertension, thrombosis, migraine, vasospasm, ischemia, depression, anxiety, psychosis, schizophrenia, sleep disorders and appetite disorders.

Schizophrenia is a particularly devastating neuropsychiatric disorder that affects approximately 1% of the human population. It has been estimated that the total financial cost for the diagnosis, treatment, and lost societal productivity of individuals affected by this disease exceeds 2% of the gross national product (GNP) of the United States. Current treatment primarily involves pharmacotherapy with a class of drugs known as antipsychotics. Antipsychotics are effective in ameliorating positive symptoms (e.g., hallucinations and delusions), yet they frequently do not improve negative symptoms (e.g., social and emotional withdrawal, apathy, and poverty of speech).

Currently, nine major classes of antipsychotics are prescribed to treat psychotic symptoms. Use of these compounds is limited, however, by their side effect profiles. Nearly all of the "typical" or older generation compounds have significant adverse effects on human motor function. These "extrapyramidal" side effects, so termed due to their effects on modulatory human motor systems, can be both acute (e.g., dystonic reactions, a potentially life threatening but rare neuroleptic malignant syndrome) and chronic (e.g., akathisias, tremors, and tardive dyskinesia). Drug development efforts have, therefore, focused on newer "atypical" agents free of these adverse effects.

Antipsychotic drugs have been shown to interact with a large number of central monoaminergic neurotransmitter receptors, including dopaminergic, serotonergic, adrenergic, muscarinic, and histaminergic receptors. It is likely that the therapeutic and adverse effects of these drugs are mediated by distinct receptor subtypes. The high degree of genetic and pharmacological homology between these receptor subtypes has hampered the development of subtype-selective compounds, as well as the determination of the normal physiologic or pathophysiologic role of any particular receptor subtype. Thus there is a need to develop drugs that are selective for individual receptor classes and subclasses amongst monoaminergic neurotransmitter receptors.

The prevailing theory for the mechanism of action of antipsychotic drugs involves antagonism of dopamine D2 receptors. Unfortunately, it is likely that antagonism of dopamine D2 receptors also mediates the extrapyramidal side effects. Antagonism of 5-HT2A is an alternate molecular mechanism for drugs with antipsychotic efficacy, possibly through antagonism of heightened or exaggerated signal transduction through serotonergic systems. 5-HT2A antagonists are therefore good candidates for treating psychosis without extrapyramidal side effects.

Traditionally, these receptors have been assumed to exist in a quiescent state unless activated by the binding of an agonist (a drug that activates a receptor). It is now appreciated that many, if not most, of the GPCR monoamine receptors, including serotonin receptors, can exist in a partially activated state in the absence of their endogenous agonists. This increased basal activity (constitutive activity) can be inhibited by compounds called inverse agonists. Both agonists and inverse agonists possess intrinsic activity at a receptor, in that they alone can activate or inactivate these molecules, respectively. In contrast, classic or neutral antagonists compete against agonists and inverse agonists for access to the receptor, but do not possess the intrinsic ability to inhibit elevated basal or constitutive receptor responses.

We have recently elucidated an important aspect of 5-HT2A receptor function by applying the Receptor Selection and Amplification Technology (U.S. Pat. No. 5,707,798, 1998; Chem Abstr. 128:111548 (1998) and citations therein), to the study of the 5-HT2 subclass of serotonin receptors. R-SAT is a phenotypic assay of receptor function that involves the heterologous expression of receptors in mammalian fibroblasts. Using this technology we were able to demonstrate that native 5-HT2A receptors possess significant constitutive, or agonist-independent, receptor activity (U.S. Patent Application Ser. No. 60/103,317, herein incorporated by reference). Furthermore, by directly testing a large number of centrally acting medicinal compounds with known clinical activity in neuropsychiatric disease, we determined that compounds with antipsychotic efficacy all shared a common molecular property. Nearly all of these compounds, which are used by psychiatrists to treat psychosis, were found to be potent 5-HT2A inverse agonists. This unique clinico-pharmacologic correlation at a single receptor subtype is compelling evidence that 5-HT2A receptor inverse agonism is a molecular mechanism of antipsychotic efficacy in humans.

Detailed pharmacological characterization of a large number of antipsychotic compounds revealed that they possess broad activity at multiple related receptor subtypes. Most of these compounds display agonist, competitive antagonist, or inverse agonist activity at multiple monoaminergic receptor subtypes, including serotoninergic, dopaminergic, adrenergic, muscarinic and histaminergic receptors. This broad activity is likely responsible for the sedating, hypotensive, and motor side effects of these compounds. It would therefore be of great advantage to develop compounds that are selective inverse agonists of the 5-HT2A receptor, but which have little or no activity on other monamine receptors subtypes, especially dopamine D2 receptors. Such compounds may be useful in the treatment of human disease (e.g., as anti-psychotics), and may avoid the adverse side effects associated with non-selective receptor interactions.

SUMMARY OF THE INVENTION

The present invention provides compounds of the general formula (I) that affect monoamine receptors, especially serotonin receptors, and share as a common property inverse agonist activity at the 5-HT2A subtype of human serotonin receptors:

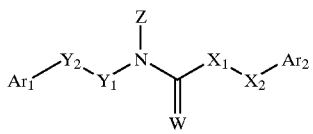

wherein

Z is a group selected from

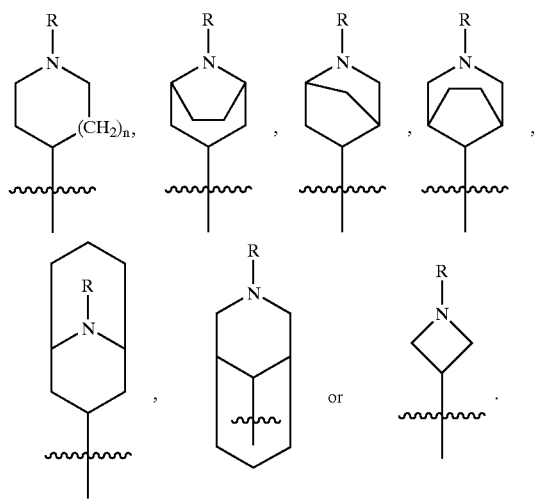

R is hydrogen, a cyclic or straight-chained or branched acyclic organyl group, a lower hydroxyalkyl group, a lower aminoalkyl group, or an aralkyl or heteroaralkyl group;

n is 0, 1, or 2;

$X_1$ is methylene, vinylene, or an NH or N(lower alkyl) group; and $X_2$ is methylene, or, when $X_1$ is methylene or vinylene, $X_2$ is methylene or a bond; or when $X_1$ is methylene, $X_2$ is O, S, NH, or N(lower alkyl) or a bond;

$Y_1$ is methylene and $Y_2$ is methylene, vinylene, ethylene, propylene, or a bond; or $Y_1$ is a bond and $Y_2$ is vinylene; or $Y_1$ is ethylene and $Y_2$ is O, S, NH, or N(lower alkyl);

$Ar_1$ and $Ar_2$ independently are unsubstituted or substituted aryl or heteroaryl groups;

W is oxygen or sulfur; or a pharmaceutically acceptable salt, ester, or prodrug thereof.

The present invention also provides pharmaceutical compositions comprising an effective amount of a compound of formula (I) or pharmaceutically acceptable salts, esters, or prodrugs thereof.

Also provided are methods of inhibiting an activity of a monoamine receptor comprising contacting the monoamine receptor or a system containing the monoamine receptor with an effective amount of a compound of formula (I), as well as kits for performing the same. Preferably, the receptor is a serotonin receptor of the 5-HT2A subclass. The receptor may be located in either the central or peripheral nervous system, blood cells or platelets, and may be mutated or modified. In a preferred embodiment, the receptor is constitutively active.

Furthermore, the present invention relates to a method of inhibiting an activation of a monoamine receptor comprising contacting the monoamine receptor or a system containing the monoamine receptor with an effective amount of compound of formula (I), as well as kits for performing the same. In a preferred embodiment, the compound is selective for the 5-HT2A serotonin receptor. In another preferred embodiment, the compound has little or substantially no anti-dopaminergic activity. The receptor may be constitutively active or may be activated by an endogenous or exogenous agonistic agent.

Another aspect of the present invention relates to a method of treating a disease condition associated with a monoamine receptor comprising administering to a mammal in need of such treatment an effective amount of a compound of formula (I), and kits for performing the same. Examples of disease conditions for which such treatment using the compounds of the invention, or pharmaceutical compositions comprising them, is useful include, but are not limited to, neuropsychiatric diseases such as schizophrenia and related idiopathic psychoses, depression, anxiety, sleep disorders, appetite disorders, affective disorders such as major depression, bipolar disorder, and depression with psychotic features, and Tourette's Syndrome. Said compounds may also be beneficial for the treatment of drug-induced psychoses as well as psychoses secondary to neurodegenerative disorders such as Alzheimer's or Huntington's Disease. The compounds of the invention may also be useful in treating hypertension, migraine, vasospasm, ischemia and the primary treatment and secondary prevention of various thrombotic conditions including myocardial infarction, thrombotic or ischemic stroke, idiopathic and thrombotic thrombocytopenic purpura, and peripheral vascular disease.

Further provided is a method for identifying a genetic polymorphism predisposing a subject to being responsive to a compound of formula (I), comprising administering to a subject an effective amount of the compound; identifying a responsive subject having an ameliorated disease condition associated with a monoamine receptor; and identifying a genetic polymorphism in the responsive subject, wherein the genetic polymorphism predisposes a subject to being responsive to the compound. Also provided are kits for performing the same.

A method for identifying a subject suitable for treatment with the compound of formula (I) and kits for identifying the same, is also provided. According to the method, the presence of a polymorphism that predisposes the subject to being responsive to the compound is detected, wherein the presence of the polymorphism indicates that the subject is suitable for treatment.

BRIEF DESCRIPTION OF THE DRAWINGS

FIG. 2 shows the effects of this novel antipsychotic agent compound in a head twitch behavioral model; FIG. 3 shows the results of locomotor experiments; and in FIG. 4 pre-pulse inhibition study results are shown.

DETAILED DESCRIPTION OF THE INVENTION

Definitions

Figure 1:
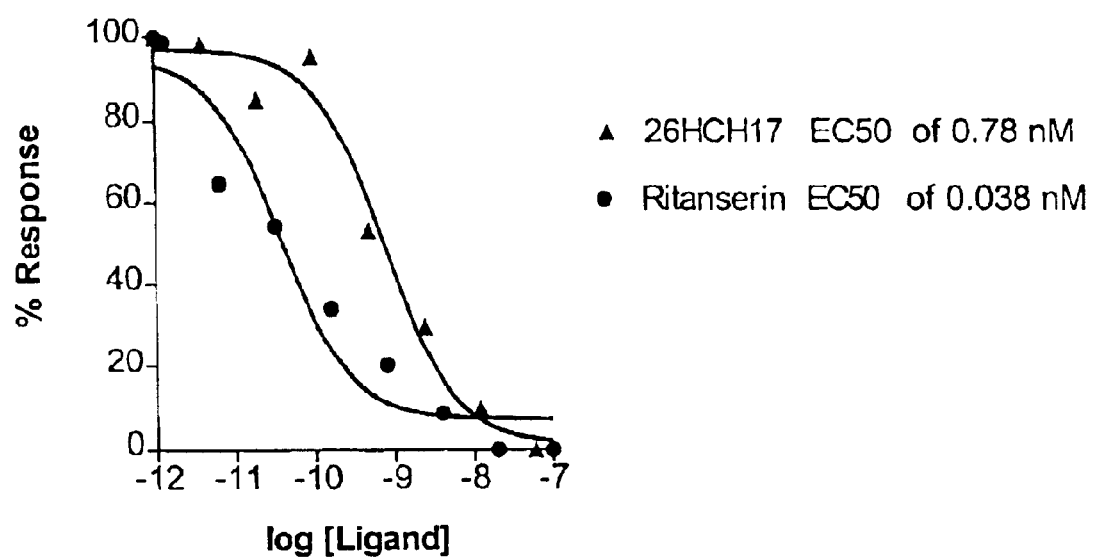
FIG. 1 is a graph showing data obtained from a dose response analysis of 26HCH17 and ritanserin as 5-HT2A receptor inverse agonists.

For the purpose of the current disclosure, the following definitions shall in their entireties be used to define technical terms, and shall also, in their entireties, be used to define the scope of the composition of matter for which protection is sought in the claims.

"Constitutive activity" is defined as the elevated basal activity of a receptor which is independent of the presence of an agonist. Constitutive activity of a receptor may be measured using a number of different methods, including cellular (e.g., membrane) preparations (see, e.g., Barr &. Manning, *J. Biol. Chem.* 272:32979–87 (1997)), purified reconstituted receptors with or without the associated G-protein in phospholipid vesicles (Cerione et al., *Biochemistry* 23:4519–25 (1984)), and functional cellular assays (U.S. patent application Ser. No. 60/103,317).

"Agonist" is defined as a compound that increases the activity of a receptor when it contacts the receptor.

An "antagonist" is defined as a compound that competes with an agonist or inverse agonist for binding to a receptor, thereby blocking the action of an agonist or inverse agonist on the receptor. However, an antagonist (also known as a "neutral" antagonist) has no effect on constitutive receptor activity.

An "inverse agonist" is defined as a compound that decreases the basal activity of a receptor (i.e., signalling mediated by the receptor). Such compounds are also known as negative antagonists. An inverse agonist is a ligand for a receptor that causes the receptor to adopt an inactive state relative to a basal state occurring in the absence of any ligand. Thus, while an antagonist can inhibit the activity of an agonist, an inverse agonist is a ligand that can alter the conformation of the receptor in the absence of an agonist. The concept of an inverse agonist has been explored by Bond et al. in *Nature* 374:272 (1995). More specifically, Bond et al. have proposed that unliganded $\beta_2$-adrenoceptor exists in an equilibrium between an inactive conformation and a spontaneously active conformation. Agonists are proposed to stabilize the receptor in an active conformation. Conversely, inverse agonists are believed to stabilize an inactive receptor conformation. Thus, while an antagonist manifests its activity by virtue of inhibiting an agonist, an inverse agonist can additionally manifest its activity in the absence of an agonist by inhibiting the spontaneous conversion of an unliganded receptor to an active conformation.

The "5-HT2A receptor" is defined as a receptor, having an activity corresponding to the activity of the human serotonin receptor subtype, which was characterized through molecular cloning and pharmacology as detailed in Saltzman et al., *Biochem. Biophys. Res. Comm.* 181:1469–78; and Julius et al., *Proc. Natl. Acad. Sci. USA* 87:928–932.

The term "subject" refers to an animal, preferably a mammal, most preferably a human, who is the object of treatment, observation or experiment.

"Selective" is defined as a property of a compound whereby an amount of the compound sufficient to effect a desired response from a particular receptor type, subtype, class or subclass with substantially little or no effect upon the activity other receptor types. "Selectivity" or "selective," as an inverse agonist is understood as a property of a compound of the invention whereby an amount of compound that effectively inversely agonises the 5-HT2A receptor, and thereby decreases its activity, causes little or no inverse agonistic or antagonistic activity at other, related or unrelated, receptors. In particular, the compounds of the invention have surprisingly been found not to interact strongly with other serotonin receptors (5-HT 1A, 1B, 1D, 1E, 1F, 2B, 2C, 4A, 6, and 7) at concentrations where the signalling of the 5-HT2A receptor is strongly or completely inhibited. Preferably, the compounds of the invention are also selective with respect to other monoamine-binding receptors, such as the dopaminergic, histaminergic, adrenergic and muscarinic receptors. Compounds that are highly selective for 5-HT2A receptors may have a beneficial effect in the treatment of psychosis, schizophrenia or similar neuropsychiatric disorders, while avoiding adverse effects associated with drugs hitherto suggested for this purpose.

EC50 for an agonist is intended to denote the concentration of a compound needed to achieve 50% of a maximal response seen in R-SAT. For inverse agonists, EC50 is intended to denote the concentration of a compound needed to achieve 50% inhibition of an R-SAT response from basal, no compound, levels.

As used herein, "coadministration" of pharmacologically active compounds refers to the delivery of two or more separate chemical entities, whether in vitro or in vivo. Coadministration refers to the simultaneous delivery of separate agents; to the simultaneous delivery of a mixture of agents; as well as to the delivery of one agent followed by delivery of a second agent or additional agents. In all cases, agents that are coadministered are intended to work in conjunction with each other.

"Cyclic organyl groups" are aliphatic, alicyclic groups in which carbon atoms form a ring. In preferred embodiments containing four, five, six or seven carbon atoms, the ring, as a substituent, is connected either directly via one of the ring atoms or via one or more appended carbon atoms. Particular examples of such groups include cyclopentyl, cyclohexyl, cycloheptyl, cyclopentylmethyl, cyclohexylmethyl, cyclohexylethyl groups, and the like.

"Straight-chained acyclic organyl groups" are substituent groups consisting of a linear arrangement of carbon atoms, where accordingly each carbon atom binds a maximum of two other carbon atoms, connected through single, double, or triple bonds. The straight-chained organyl groups may contain none, one, or several multiple bonds, and are, for example, commonly referred to as alkyl, alkenyl or alkynyl, or alkadienyl groups, respectively. Examples of straight-chained organyl groups include methyl, ethyl, propyl, butyl, pentyl, hexyl, propenyl, butenyl, pentadienyl, propargyl, butynyl.

"Branched acyclic organyl groups" are substituent groups consisting of a branched arrangement of carbon atoms, where accordingly one or more carbon atoms may bind more than two other carbon atoms, connected through single, double, or triple bonds. The branched organyl groups may contain none, one, or several multiple bonds. Examples of branched organyl groups include iso-propyl, iso-butyl, tert-butyl, methylbutyl, methylbutenyl, methylbutynyl.

"Lower alkoxy groups" are $C_{1-6}$ cyclic or acyclic organyl groups connected, as substituents, via an oxygen atom. Examples of lower alkoxy groups include methoxy, ethoxy, iso-propoxy, butoxy, tert-butoxy.

"Lower alkyl groups" are $C_{1-6}$ cyclic, straight-chained or branched aliphatic substituent groups connected via a carbon atom. Examples include methyl, ethyl, propyl, butyl, methylbutyl, cyclopropyl, cyclohexyl, iso-propyl, tert-butyl.

"Lower alkylamino groups" are understood as lower alkyl groups connected, as substituents, via a nitrogen atom, which may carry one or two lower alkyl groups. Particular examples include methylamino, dimethylamino, iso-propylamino. Optionally, lower aminoalkyl groups may consist of 4–6 membered nitrogen-containing rings, such as pyrrolidino.

"Lower aminoalkyl groups" are lower alkyl groups carrying, as a substituent, an additional amino group. Examples include aminomethyl and aminoethyl.

"Lower hydroxyalkyl groups" are understood as lower alkyl groups carrying, as a substituent, an additional hydroxy group. Examples include hydroxymethyl, hydroxyethyl, 2-hydroxy-2-propyl, hydroxypentyl.

"Acyl groups" are hydrogen or lower alkyl groups connected, as substituents, via a carbonyl group. Examples include formyl, acetyl, propanoyl.

"Halo groups" are understood to be fluoro, chloro, bromo, or iodo substituents, with fluoro and chloro being generally preferred.

"Lower alkylene groups" are straight-chained tethering groups, forming bonds to connect molecular fragments via their terminal carbon atoms. Examples include methylene ($-CH_2-$), ethylene ($-CH_2CH_2-$), propylene ($-CH_2CH_2CH_2-$) or butylene ($-(CH_2)_4-$) groups.

"Vinylene groups" are ethene-1,2-diyl groups ($-CHCH-$) having (E) or (Z) configuration.

"Aralkyl groups" are aryl groups connected, as substituents, via a lower alkylene group. The aryl groups of aralkyl groups may be substituted or unsubstituted. Examples include benzyl, substituted benzyl, 2-phenylethyl, 3-phenylpropyl, naphthylalkyl.

'Heteroaralkyl groups' are understood as heteroaryl groups connected, as substituents, via a lower alkylene group. The heteroaryl groups of heteroaralkyl groups may be substituted or unsubstituted. Examples include 2-thienylmethyl, 3-thienylmethyl, furylmethyl, thienylethyl, pyrrolylalkyl, pyridylalkyl, isoxazolylalkyl, imidazolylalkyl, and their substituted as well as benzo-fused analogs.

"Aryl groups" are aromatic, preferably benzenoid or naphthoid, groups connected via one of the ring-forming carbon atoms, and optionally carrying one or more substituents selected from halo, hydroxy, amino, cyano, nitro, alkylamido, acyl, lower alkoxy, lower alkyl, lower hydroxyalkyl, lower aminoalkyl, lower alkylamino, alkylsulfenyl, alkylsulfinyl, alkylsulfonyl, sulfamoyl, or trifluoromethyl. Preferred aryl groups are phenyl, and, most suitably, substituted phenyl groups, carrying one or two, same or different, of the substituents listed above. The preferred pattern of substitution is para and/or meta. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 3-cyanophenyl, 4-cyanophenyl, dimethylphenyl, naphthyl, hydroxynaphthyl, hydroxymethylphenyl, trifluoromethylphenyl.

"Heteroaryl groups" are understood as aromatic, $C_{2-6}$ cyclic groups containing one O or S atom or up to four N atoms, or a combination of one O or S atom with up to two N atoms, and their substituted as well as benzo- and pyrido-fused derivatives, preferably connected via one of the ring-forming carbon atoms. Heteroaryl groups may carry one or more substituents, selected from halo, hydroxy, amino, cyano, nitro, alkylamido, acyl, lower alkoxy, lower alkyl, lower hydroxyalkyl, lower aminoalkyl, lower alkylamino, alkylsulfenyl, alkylsulfinyl, alkylsulfonyl, sulfamoyl, or trifluoromethyl. Preferred heteroaryl groups are five- and six-membered aromatic heterocyclic systems carrying 0, 1, or 2 substituents, which may be the same as or different from one another, selected from the list above. Representative examples of heteroaryl groups include, but are not limited to, unsubstituted and mono- or di-substituted derivatives of furan, benzofuran, thiophene, benzothiophene, pyrrole, indole, oxazole, benzoxazole, isoxazole, benzisoxazole, thiazole, benzothiazole, isothiazole, imidazole, benzimidazole, pyrazole, indazole, and tetrazole, which are all preferred, as well as furazan, 1,2,3-oxadiazole, 1,2,3-thiadiazole, 1,2,4-thiadiazole, triazole, benzotriazole, pyridine, quionoline, isoquinoline, pyridazine, pyrimidine, purine, pyrazine, pteridine, and triazine. The most preferred substituents are halo, hydroxy, cyano, lower alkoxy, lower alkyl, lower hydroxyalkyl, lower alkylamino, and lower aminoalkyl.

The present invention provides compounds preferably showing a realtively high selectivity toward serotonin receptors, particularly, 5-HT2A receptors, which may have a beneficial effect in the treatment of neuropsychiatric disorders.

According to one embodiment, the present invention provides compounds of the general formula (I):

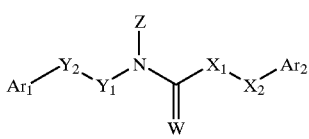

wherein

Z is

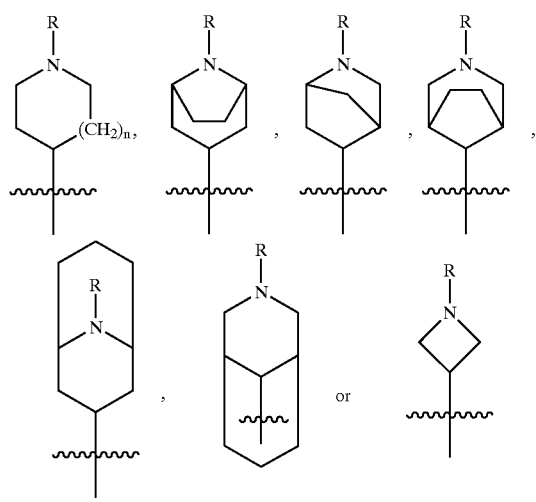

in which

R is a hydrogen, a cyclic or straight-chained or branched acyclic organyl group, a lower hydroxyalkyl group, a lower aminoalkyl group, or an aralkyl or heteroaralkyl group;

n is 0, 1, or 2;

$X_1$ is methylene, vinylene, or an NH or N (lower alkyl) group; and $X_2$ is methylene, or, when $X_1$ is methylene or vinylene, $X_2$ is methylene or a bond; or when $X_1$ is methylene, $X_2$ is O, S, NH, or N(lower alkyl) or a bond;

X $Y_1$ is methylene and $Y_2$ is methylene, vinylene, ethylene, propylene, or a bond; or $Y_1$ is a bond and $Y_2$ is vinylene; or $Y_1$ is ethylene and $Y_2$ is O, S, NH, or N(lower alkyl);

$Ar_1$ and $Ar_2$ independently are unsubstituted or substituted aryl or heteroaryl groups; and W is oxygen or sulfur;

or a pharmacologically acceptable salt, ester, or prodrug thereof.

In general, compounds of formula (I) are active at monoamine receptors, specifically serotonin receptors. Preferred compounds share the common property of acting as inverse agonists at the 5-HT2A receptor. Thus, experiments performed on cells transiently expressing the human phenotype of said receptor have shown that the compounds of general formula (I) attenuate the signalling of such receptors in the absence of additional ligands acting upon the receptor. The compounds have thus been found to possess intrinsic activity at this receptor and are able to attenuate the basal, non-agonist-stimulated, constitutive signalling responses that the 5-HT2A receptor displays. The observation that the compounds of general formula (I) are inverse agonists also indicates that these compounds have the ability to antagonize the activation of 5-HT2A receptors that is mediated by endogenous agonists or exogenous synthetic agonist ligands.

In a preferred embodiment, the present invention provides compounds that preferably show a relatively high degree of selectivity towards the 5-HT2A subtype of serotonin receptors relative to other subtypes of the serotonin (5-HT) family of receptors as well as to other receptors, most particularly the monoaminergic G-protein coupled receptors, such as dopamine receptors. In another preferred embodiment, the compounds of the present invention act as inverse agonists at the 5-HT2A subtype of serotonin receptors.

The compounds of general formula (I) may therefore be useful for treating or alleviating symptoms of disease conditions associated with impaired function, in particular elevated levels of activity, of especially 5-HT2A receptors, whether this impaired function is associated with improper levels of receptor stimulation or phenotypical aberrations.

Others have previously hypothesised that certain neuropsychological diseases might be caused by altered levels of constitutive activity of monoamine receptors. Such constitutive activity might be modified via contacting the relevant receptor with a synthetic inverse agonist. By directly testing a large number of centrally acting medicinal compounds with known clinical activity in neuropsychiatric disease, we determined that compounds with antipsychotic efficacy all shared a common molecular property. Nearly all of these compounds that are used by psychiatrists to treat psychosis were found to be potent 5-HT2A inverse agonists. This correlation is compelling evidence that 5-HT2A receptor inverse agonism is a molecular mechanism of antipsychotic efficacy in humans.

Detailed pharmacological characterization of a large number of antipsychotic compounds in our laboratory revealed that they possess broad activity at multiple related receptor subtypes. Most of these compounds display either agonist, competitive antagonist, or inverse agonist activity at multiple monoaminergic receptor subtypes including serotoninergic, dopaminergic, adrenergic, muscarinic and histaminergic receptors. This broad activity is likely responsible for the sedating, hypotensive, and motor side effects of these compounds. It follows that the compounds disclosed herein will possess efficacy as, for example, novel antipsychotics, but will have fewer or less severe side effects than existing compounds.

The present invention also provides pharmaceutical compositions comprising an effective amount of a compound of general formula (I).

In a preferred embodiment of the compounds of formula (I), $Y_1$ is methylene and $Y_2$ is a bond, methylene, ethylene, or vinylene, or $Y_1$ is ethylene and $Y_2$ is O or S, and $X_1$ is methylene and $X_2$ is a bond, methylene, O, or S, or $X_1$ is NH or N(lower alkyl).

In a further preferred embodiment of the compounds of formula (I), Z is

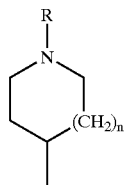

and W is oxygen.

In a more preferred embodiment of the compounds of formula (I), n is 1, $Y_1$ is methylene, $Y_2$ is a bond, methylene, ethylene, or vinylene, $X_1$ is methylene and $X_2$ is a bond, or $X_1$ is NH or N(lower alkyl) and $X_2$ is methylene. In a further preferred embodiment of the compounds of formula (I), W is oxygen and $Ar_1$ and $Ar_2$ are different aryl or heteroaryl groups, with different mono-substituted phenyl groups being particularly preferred. Preferably, $Ar_1$ and $Ar_2$ are not simultaneously phenyl.

Also preferred compounds of formula (I) are those where Z is 1-(organyl or aralkyl)-4-piperidinyl.

In another embodiment, the invention provides preferred compounds ot the formula (II):

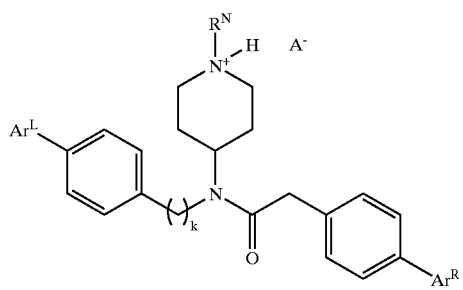

in which $R^N$ is hydrogen, lower alkyl, aralkyl, or heteroaralkyl;

$Ar^L$ is selected from lower alkyl, lower alkoxy and halogen $Ar^R$ is selected from lower alkyl, lower alkoxy and halogen;

k is 1 or 2 and A is a suitable anion.

According to the invention, a suitable anion may be any anion capable of forming a pharmaceutically acceptable salt of the compound, as described in further detail below.

The present invention also provides a method of inhibiting an activity of a monoamine receptor. This method comprises contacting a monoamine receptor or a system containg the monamine receptor, with an effective amount of a compound of formula (I). Accoding to one embodiment, the monamine receptor is a serotonin receptor. In a preferred embodiment, the compound is selective for the 5-HT2A receptor subclass. In another preferred embodiment, the compound has little or substantially no activity to other types of receptors, including other serotonergic receptors and most particularly, monoaminergic G-protein coupled receptors, such as dopaminergic receptors.

The system containing the monoamine receptor may, for example, be a subject such as a mammal, non-human primate or a human. The receptor may be located in the central or peripheral nervous system, blood cells or platelets.

The system may also be an in vivo or in vitro experimental model, such as a cell culture model system that expresses a monoamine receptor, a cell-free extract thereof that contains a monoamine receptor, or a purified receptor. Non-limiting examples of such systems are tissue culture cells expressing the receptor or extracts or lysates thereof. Cells that may be used in the present method include any cells capable of mediating signal transduction via monoamine receptors, expecially the 5-HT2A receptor, either via endogenous expression of this receptor (e.g., certain types of neuronal cells lines, for example, natively express the 5-HT2A receptor), or following transfection of cells with plasmids containing the receptor gene. Such cells are typically mammalian cells (or other eukaryotic cells, such as insect cells or Xenopus oocytes), because cells of lower organisms generally lack the appropriate signal transduction pathways for the present purpose. Examples of suitable cells include: the mouse fibroblast cell line NIH 3T3 (ATCC CRL 1658), which responds to transfected 5-HT2A receptors by stimulating growth; RAT 1 cells (Pace et al., *Proc. Natl. Acad. Sci. USA* 88:7031–35 (1991)); and pituitary cells (Vallar et al., *Nature* 330:556–58 (1987)). Other useful mammalian cells for the present method include HEK 293 cells, CHO cells and COS cells.

The invention specifically provides methods of inhibiting an activity of a native, mutated or modified monoamine receptor. Also provided are kits for performing the same. In a preferred embodiment, the activity of the receptor is a signalling activity. In another preferred embodiment, the activitiy of the receptor is the constitutive basal activity of the receptor. Preferably, the compound is an inverse agonist selective for the 5-HT2A receptor. Most preferably, the compound has little or substantially no activity toward other serotonergic or other monoaminergic receptors, such as dopaminergic receptors.

In one embodiment, the activity of the receptor is a response, such as a signalling response, to an endogenous agonist, such as 5-HT, or an exogenous agonistic agent, such as a drug or other synthetic ligand. The compound of formula (I) preferably acts by inversely agonising or antagonising the receptor.

Furthermore, the present invention relates to a method of inhibiting an activation of a monoamine receptor comprising contacting the monoamine receptor, or a system containing the monoamine receptor, with one or more compounds of the invention. The activation of the receptor may be due to an exogenous or endogenous agonist agent, or may be the constitutive activation associated with a native, mutated or modified receptor. The receptor may purified or present in an in vitro or in vivo system. The receptor may also be present in the central or peripheral nervous system, blood cells or platelets of a nonhuman or human subject. Also provided are kits for performing the same.

In a preferred embodiment, the compound is selective for 5-HT class serotonin receptors, more preferably, the 5-HT2A sublass of serotonin receptors. In another preferred embodiment, the compound has little or substantially no anti-dopaminergic activity.

The present invention provides methods of treating a disease condition associated with a monoamine receptor comprising administering to a mammal in need of such treatment an effective amount of a compound of formula (I). The invention specifically provides methods for treating or alleviating disease conditions associated with improper function or stimulation of native, as well as mutated or otherwise modified, forms of central serotonin receptors, particularly the 5-HT class of such receptors, comprising administration of an effective amount of a selective inverse agonist of the general formula (I) to a host in need of such treatment. Also provided are kits for performing the same.

In a preferred embodiment, the receptor is the 5-HT2A subclass. In one embodiment, the disease condition is associated with dysfunction of the serotonin receptor. In another embodiment, the disease condition is associated with activation of the serotonin receptor, preferably inappropriately elevated or constitutive activation, elevated serotonergic tone, as well as disease conditions associated with secondary cellular functions imparied by such pathologies.

Examples of diseases for which such treatment using the compounds of the invention, or pharmaceutical compositions comprising such compounds, is useful include, but are not limited to, neuropsychiatric diseases such schizophrenia and related idiopathic. psychoses, anxiety, sleep disorders, appetite disorders, affective disorders such as major depression, bipolar disorder, and depression with psychotic features, and Tourette's Syndrome, drug-induced psychoses, psychoses secondary to neurodegenerative disorders such as Alzheimer's or Huntington's Disease. It is anticipated that the compounds of this invention, particularly selective inverse agonists of 5-HT2A that show little or no activity on dopaminergic receptors, may be especially useful for treating schizophrenia. Treament using the compounds of the invention may also be useful in treating migraine, vasospasm, hypertension, various thrombotic conditions including myocardial infarction, thrombotic or ischemic stroke, idiopathic and thrombotic thrombocytopenic purpura, and peripheral vascular disease.

In a further embodiment the present invention provides methods for treating or alleviating a disease condition associated with improper function, dysfunction, or stimulation of native, as well as mutated or otherwise modified, forms of central or peripheral monoamine receptors, such methods comprising administration of an effective amount of a compound of the general formula (I) to a host in need of such treatment. Preferably the monamine receptor is serotonin receptor in the peripheral nervous system, blood or platelets; more preferably a 5-HT2A subclass receptor. In additional embodiments, the disease condition is associated with increased activity or activation of a serotonin receptor. Also provided are kits for performing the same.

The present invention also pertains to the field of predictive medicine in which pharmacogenomics is used for prognostic (predictive) purposes. Pharmacogenomics deals with clinically significant hereditary variations in the response to drugs due to altered drug disposition and abnormal action in affected persons. See e.g., Eichelbaum, *Clin Exp Pharmacol. Physiol.*, 23:983–985 (1996), and Linder, *Clin. Chem.* 43:254–66 (1997). In general, two types of pharmacogenetic conditions can be differentiated: genetic conditions transmitted as a single factor altering the way drugs act on the body (altered drug action), and genetic conditions transmitted as single factors altering the way the body acts on drugs (altered drug metabolism). These pharmacogenetic conditions can occur as naturally occurring polymorphisms.

One pharmacogenomics approach to identifying genes that predict drug response, known as "a genome-wide association," relies primarily on a high-resolution map of the human genome consisting of already known gene-related markers (e.g., a "bi-allelic" gene marker map that consists of 60,000–100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high-resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1,000 bases of DNA. A SNP may be involved in a disease process; however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach" can be utilized to identify genes that predict drug response. According to this method, if a gene that encodes a drug's target is known (e.g., a protein or a receptor of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a molecule or modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a molecule or modulator of the invention, such as a modulator identified by one of the exemplary screening assays described herein. As we have described previously, this approach can also be used to identify novel candidate receptor or other genes suitable for further pharmacological characterization in vitro and in vivo.

Accordingly, the present invention also provides methods and kits for identifying a genetic polymorphism predisposing a subject to being responsive to a compound described herein. The method comprises administering to a subject an effective amount of a compound; identifying a responsive subject having an ameliorated disease condition associated with a monamine receptor; and identifying a genetic polymorphism in the responsive subject, wherein the genetic polymorphism predisposes a subject to being responsive to the compound. It is anticipated that this method may be useful both for predicting which individuals are responsive to therapeutic effects of a compound and also for predicting those likely to experience adverse side effect responses. This approach may be useful for identifying, for example, polymorphisms in a serotonin receptor that lead to constitutive activation and are thus amenable to inverse agonist therapy. In addition, this method may be useful for identifying polymorphisms that lead to altered drug metabolism whereby toxic byproducts are generated in the body. Such a mechanism has been implicated in the rare, but potentially life threatening side effects of the atypical antipsychotic, clozapine.

In a related embodiment, a method for identifying a subject suitable for treatment with a compound of the present invention is provided. According to the method, the presence of a polymorphism that predisposes the subject to being responsive to the compound is detected, the presence of the polymorphism indicating that the subject is suitable for treatment. Also provided are kits for performing the same.

The compounds of this invention preferably show selective inverse agonist activity towards the 5-HT2A receptor. Such activity is defined by an ability of the ligand to attenuate or abolish the constitutive signaling activity of this receptor. Selectivity in the present context is understood as a property of a compound of the invention whereby an amount of compound that effectively inversely agonizes the 5-HT2A receptor and thereby decreases its activity causes little or no inverse agonistic or antagonistic activity at other, related or unrelated, receptors. In particular, the compounds of the invention have surprisingly been found not to interact strongly with other serotonin receptors (5-HT 1A, 1B, 1D, 1E, 1F, 2B, 2C, 4A, 6, and 7) at concentrations where the signaling of the 5-HT2A receptor is strongly or completely inhibited. Preferably, the compounds of the invention are also selective with respect to other monoamine-binding receptors, such as the dopaminergic, histaminergic, adrenergic and muscarinic receptors.

A particularly preferred embodiment of this invention includes:

N-(1-(1-methylethyl)piperidin-4-yl)-N-((4-methylphenyl)methyl)-4-methoxyphenylacetamide;
N-(1-(2,2-dimethylethyl)piperidin-4-yl)-N-((4-methylphenyl)methyl)-4-methoxyphenylacetamide;
N-(1-pentylpiperidin-4-yl)-N-((4-methylphenyl)methyl)-4-methoxyphenylacetamide;
N-(1-hexylpiperidin-4-yl)-N-((4-methylphenyl)methyl)-4-methoxyphenylacetamide;
N-(1-cyclohexylpiperidin-4-yl)-N-((4-methylphenyl)methyl)-4-methoxyphenylacetamide;
N-(1-cyclopentylpiperidin-4-yl)-N-((4-methylphenyl)methyl)-4-methoxyphenylacetamide;
N-(1-cyclobutylpiperidin-4-yl)-N-((4-methylphenyl)methyl)-4-methoxyphenylacetamide;
N-(1-cyclopropylpiperidin-4-yl)-N-((4-methylphenyl)methyl)-4-methoxyphenylacetamide;
N-(1-(cyclopentylmethyl)piperidin-4-yl)-N-((4-methylphenyl)methyl)-4-methoxyphenylacetamide;
N-(1-(cyclobutylmethyl)piperidin-4-yl)-N-((4-methylphenyl)methyl)-4-methoxyphenylacetamide;
N-(1-(cyclopropylmethyl)piperidin-4-yl)-N-((4-methylphenyl)methyl)-4-methoxyphenylacetamide;
N-(1-(2-hydroxyethyl)piperidin-4-yl)-N-((4-methylphenyl)methyl)-4-methoxyphenylacetamide;
N-(1-(3-hydroxypropyl)piperidin-4-yl)-N-((4-methylphenyl)methyl)-4-methoxyphenylacetamide;
N-((4-Methylphenyl)methyl)-N-(piperidin-4-yl)-N'-phenylmethylcarbamide;
N-((4-Methylphenyl)methyl)-N-(1-(2-methylpropyl)piperidin-4-yl)-N'-phenylmethylcarbamide;
N-(1-((2-Bromophenyl)methyl)piperidin-4-yl)-N-((4-methylphenyl)methyl)-N'-phenylmethylcarbamide;
N-(1-((4-Hydroxy-3-methoxyphenyl)methyl)piperidin-4-yl)-N-((4-methylphenyl)methyl)-N'-phenylmethylcarbamide;
N-(1-((5-Ethylthien-2-yl)methyl)piperidin-4-yl)-N-((4-methylphenyl)methyl)-N'-phenylmethylcarbamide;
N-(1-(Imidazol-2-ylmethyl)piperidin-4-yl)-N-((4-methylphenyl)methyl)-N'-phenylmethylcarbamide;
N-(1-(Cyclohexylmethyl)piperidin-4-yl)-N-((4-methylphenyl)methyl)-N'-phenylmethylcarbamide;
N-(1-((4-Fluorophenyl)methyl)piperidin-4-yl)-N-((4-methylphenyl)methyl)-N'-phenylmethylcarbamide;
N-((4-Methylphenyl)methyl)-N-(piperidin-4-yl)-4-methoxyphenylacetamide;
N-((4-Methylphenyl)methyl)-N-(1-methylpiperidin-4-yl)-4-methoxyphenylacetamide;
N-(1-Ethylpiperidin-4-yl)-N-((4-methylphenyl)methyl)-4-methoxyphenylacetamide;
N-((4-Methylphenyl)methyl)-N-(1-propylpiperidin-4-yl)-4-methoxyphenylacetamide;
N-(1-Butylpiperidin-4-yl)-N-((4-methylphenyl)methyl)-4-methoxyphenylacetamide;
N-(1-(3,3-Dimethylbutyl)piperidin-4-yl)-N-((4-methylphenyl)methyl)-4-methoxyphenylacetamide;
N-(1-(Cyclohexylmethyl)piperidin-4-yl)-N-((4-methylphenyl)methyl)-4-methoxyphenylacetamide;
N-((4-Methylphenyl)methyl)-N-(1-(2-methylpropyl)piperidin-4-yl)-4-methoxyphenylacetamide;
N-((4-Methylphenyl)methyl)-N-(1-((4-methylphenyl)methyl)piperidin-4-yl)-4-methoxyphenylacetamide;
N-(1-((4-Hydroxyphenyl)methyl)piperidin-4-yl)-N-((4-methylphenyl)methyl)-4-methoxyphenylacetamide;
N-(1-((2-Hydroxyphenyl)methyl)piperidin-4-yl)-N-((4-methylphenyl)methyl)-4-methoxyphenylacetamide;
N-(3-Phenylpropyl)-N-(piperidin-4-yl)-4-methoxyphenylacetamide;
N-(2-Phenylethyl)-N-(piperidin-4-yl)-4-methoxyphenylacetamide;
N-((2-Methoxyphenyl)methyl)-N-(piperidin-4-yl)-4-methoxyphenylacetamide;
N-((2-Chlorophenyl)methyl)-N-(piperidin-4-yl)-4-methoxyphenylacetamide;
N-((3,4-Di-methoxyphenyl)methyl)-N-(piperidin-4-yl)-4-methoxyphenylacetamide;
N-((4-Fluorophenyl)methyl)-N-(piperidin-4-yl)-4-methoxyphenylacetamide;
N-((2,4-Di-chlorophenyl)methyl)-N-(piperidin-4-yl)-4-methoxyphenylacetamide;
N-((3-Methylphenyl)methyl)-N-(piperidin-4-yl)-4-methoxyphenylacetamide;
N-((3-Bromophenyl)methyl)-N-(piperidin-4-yl)-4-methoxyphenylacetamide;
N-(1-(Phenylmethyl)piperidin-4-yl)-N-(3-phenyl-2-propen-1-yl)-4-methoxyphenylacetamide;
N-((4-Methylphenyl)methyl)-N-(1-piperidin-4-yl)-phenylacetamide;
N-((4-Methylphenyl)methyl)-N-(1-piperidin-4-yl)-3-phenylpropionamide;
N-((4-Methylphenyl)methyl)-N-(1-piperidin-4-yl)-(phenylthio)acetamide;
N-((4-Methylphenyl)methyl)-N-(1-piperidin-4-yl)-phenoxyacetamide;
N-((4-Methylphenyl)methyl)-N-(1-piperidin-4-yl)-(4-chlorophenoxy)acetamide;
N-((4-Methylphenyl)methyl)-N-(1-piperidin-4-yl)-3-methoxyphenylacetamide;
N-((4-Methylphenyl)methyl)-N-(1-piperidin-4-yl)-4-fluorophenylacetamide;

N-((4-Methylphenyl)methyl)-N-(1-piperidin-4-yl)-2,5-di-methoxyphenylacetamide;

N-((4-Methylphenyl)methyl)-N-(1-piperidin-4-yl)-4-chlorophenylacetamide;

N-((4-Methylphenyl)methyl)-N-(1-(phenylmethyl)pyrrolidin-3-yl)-N'-phenylmethylcarbamide;

N-((4-Methylphenyl)methyl)-N-(1-(phenylmethyl)pyrrolidin-3-yl)-4-methoxyphenylacetamide;

2-(4-methoxyphenyl)-N-(4-methylbenzyl)-N-(piperidin-4-yl)acetamide;

2-(4-methoxyphenyl)-N-(4-methylbenzyl)-N-(1-methylpiperidin-4-yl)acetamide;

2-(4-methoxyphenyl)-N-(4-methylbenzyl)-N-(1-ethylpiperidin-4-yl)acetamide;

2-(4-methoxyphenyl)-N-(4-chlorbenzyl)-N-(1-ethylpiperidin-4-yl)acetamide;

2-(4-methoxyphenyl)-N-(4-chlorbenzyl)-N-(1-isopropylpiperidin-4-yl)acetamide;

2-(4-methoxyphenyl)-N-(4-chlorobenzyl)-N-(piperidin-4-yl)acetamide;

2-(4-methoxyphenyl)-N-(4-chlorbenzyl)-N-(1-cyclopentylpiperidin-4-yl)acetamide;

2-(4-methoxyphenyl)-N-(4-chlorbenzyl)-N-(1-isopropylpiperidin-4-yl)acetamide;

2-(phenyl)-N-(4-trifluoromethylbenzyl)-N-(1-methylpiperidin-4-yl)acetamide;

2-(4-fluorophenyl)-N-(4-trifluoromethylbenzyl)-N-(1-methylpiperidin-4-yl)acetamide;

2-(4-Methoxyphenyl)-N-(4-trifluoromethylbenzyl)-N-(1-methylpiperidin-4-yl)acetamide;

2-(4-Trifluoromethylphenyl)-N-(4-trifluoromethylbenzyl)-N-(1-methylpiperidin-4-yl)acetamide;

2-(4-Fluorophenyl)-N-(4-fluorobenzyl)-N-(1-methylpiperidin-4-yl)acetamide;

2-(4-Methoxyphenyl)-N-(4-fluorobenzyl)-N-(1-methylpiperidin-4-yl)acetamide;

2-(phenyl)-N-(4-fluorobenzyl)-N-(1-methylpiperidin-4-yl)acetamide;

2-(4-Trifluoromethylphenyl)-N-(4-fluorobenzyl)-N-(1-methylpiperidin-4-yl)acetamide;

2-(4-trifluoromethylphenyl)-N-[4-(methoxycarbonyl)benzyl]-N-(1-methylpiperidin-4-yl)acetamide;

2-Phenyl-N-[4-(methoxycarbonyl)benzyl]-N-(1-methylpiperidin-4-yl)acetamide;

2-(4-Chlorophenyl)-N-[4-(methoxycarbonyl)benzyl]-N-(1-methylpiperidin-4-yl)acetamide;

2-(4-Methoxyphenyl)-N-[4-(methoxycarbonyl)benzyl]-N-(1-methylpiperidin-4-yl)acetamide;

2-(4-trifluoromethylphenyl)-N-[4-(methoxycarbonyl)benzyl]-N-(1-methylpiperidin-4-yl)acetamide;

2-Phenyl-N-[4-(methoxycarbonyl)benzyl]-N-(1-methylpiperidin-4-yl)acetamide;

2-(4-Chlorophenyl)-N-[4-(methoxycarbonyl)benzyl]-N-(1-methylpiperidin-4-yl)acetamide;

2-(4-Methoxyphenyl)-N-[4-(methoxycarbonyl)benzyl]-N-(1-methylpiperidin-4-yl)acetamide;

2-(4methoxyphenyl)-N-(4-methylbenzyl)-N-[1-(4-chloromethyl-2-thiazolylmethyl)piperidin-4-yl]acetamide;

2-(4 methoxyphenyl)-N-(4-methylbenzyl)-N-{1-[3-(1,3 dihydro-2H-benzimidazol-2-on-1-yl)propyl]piperidin-4-yl}acetamide;

2-(4-methoxyphenyl)-N-(2-4(fluorophenyl)ethyl)-N-(1-methylpiperidin-4-yl)acetamide;

2-(4-methoxyphenyl)-N-[2-(2,5-dimethoxyphenyl)ethyl]-N-(1-methylpiperidin-4-yl)acetamide;

2-(4-methoxyphenyl)-N-[2-(2,4-dichlorophenyl)ethyl]-N-(1-methylpiperidin-4-yl)acetamide;

2-(4-methoxyphenyl)-N-[2-(3-chlorophenyl)ethyl]-N-(1-methylpiperidin-4-yl)acetamide;

2-(4-methoxyphenyl)-N-[2-(4-methoxyphenyl)ethyl]-N-(1-methylpiperidin-4-yl)acetamide;

2-(4-methoxyphenyl)-N-[2-(3-fluorophenyl)ethyl]-N-(1-methylpiperidin-4-yl)acetamide;

2-(4-ethoxyphenyl)-N-[2-(4-fluorophenethyl]-N-(1-methylpiperidin-4-yl)acetamide;

2-(4-ethoxyphenyl)-N-(4-fluorobenzyl)-N-(1-methylpiperidin-4-yl)acetamide;

2-(4-methoxyphenyl)-N-(4-methylbenzyl)-N-{1-[2-(2-hydroxyethoxy)ethyl]piperidin-4-yl}acetamide;

2-(4-methoxyphenyl)-N-(4-methylbenzyl)-N-[1-((2-chloro-5-thienyl)methyl) piperidin-4-yl]acetamide;

2-(4-methoxyphenyl)-N-(4-methylbenzyl)-N-[1-(2-(imidazolidinon-1-yl)ethyl)piperidin-4-yl]acetamide;

2-(4-methoxyphenyl)-N-(4-methylbenzyl)-N-{1-[2-(2,4(1H,3H)quinazolinedion-3-yl)ethyl]piperidin-4-yl}acetamide;

2-(4-methoxyphenyl)-N-(4-methylbenzyl)-N-{1-[2-(1,3-dioxolan-2-yl)ethyl]piperidin-4-yl}acetamide;

2-(4-methoxyphenyl)-N-(4-methylbenzyl)-N-{1-[2-(3-indolyl)ethyl]piperidin-4-yl}acetamide;

2-(4-methoxyphenyl)-N-(4-methylbenzyl)-N-{1-[3-(1,2,4-triazol-1-yl)propyl]piperidin-4-yl}acetamide;

2-(4-methoxyphenyl)-N-(4-methylbenzyl)-N-[1-(5-benzofurazanylmethyl)piperidin-4-yl]acetamide;

2-(4-methoxyphenyl)-N-(4-methylbenzyl)-N-[1-(5-chlorobenzo[b]thien-3-ylmethyl)piperidin-4-yl]acetamide;

2-(4-methoxyphenyl)-N-(4-methylbenzyl)-N-[1-(5-phenyl-1,2,4-oxadiazol-3-ylmethyl)piperidin-4-yl]acetamide;

2-(4-Chlorophenyl)-N-(4-methylbenzyl)-N-(1-isopropylpiperidin-4-yl)-acetamide;

2-(4-Chlorophenyl)-N-(4-methylbenzyl)-N-(1-ethylpiperidin-4-yl)-acetamide;

2-Phenyl-N-(4-methylbenzyl)-N-(1-methylpiperidin-4-yl)-acetamide,2-(4-Chlorophenyl)-N-(4-methylbenzyl)-N-(1-methylpiperidin-4-yl)-acetamide;

2-(4-Chlorophenyl)-N-(4-methylbenzyl)-N-(1-cyclopentylpiperidin-4-yl)-acetamide;

2-(4-Fluorophenyl)-N-(4-methylbenzyl)-N-(1-methylpiperidin-4-yl)-acetamide; 2-(4-Chlorophenyl)-N-(4-methylbenzyl)-N-(1-(2-hydroxyethyl)-piperidin-4-yl)-acetamide;

2-(4-Chlorophenyl)-N-(4-methylbenzyl)-N-(1-cyclobutylpiperidin-4-yl)-acetamide;

2-(4-Methoxyphenyl)-N-(4-methylbenzyl)-N-(1-cyclobutylpiperidin-4-yl)-acetamide;

2-(4-Methoxyphenyl)-N-(4-methylbenzyl)-N-(tropin-4-yl)-acetamide;

N-(4-Methylbenzyl)-N-(1-methylpiperidin-4-yl)-N'-benzyl-carbamide;

N-(4-Methylbenzyl)-N-(1-methylpiperidin-4-yl)-N'-phenyl-carbamide;

N-Phenethyl-N-(1-methylpiperidin-4-yl)-N'-benzyl-carbamide;
2-Phenyl-N-(4-methoxybenzyl)-N-(1-methylpiperidin-4-yl)-acetamide;
2-(4-Trifluoromethylphenyl)-N-(4-methoxybenzyl)-N-(1-methylpiperidin-4-yl)-acetamide;
2-(4-Fluorophenyl)-N-(4-methoxybenzyl)-N-(1-methylpiperidin-4-yl)-acetamide;
2-(4-Methoxyphenyl)-N-(4-methoxybenzyl)-N-(1-methylpiperidin-4-yl)-acetamide;
2-(4-Methylphenyl)-N-(4-chlorobenzyl)-N-(1-methylpiperidin-4-yl)-acetamide;
2-(4-Hydroxyphenyl)-N-(4-methylbenzyl)-N-(1-methylpiperidin-4-yl)-acetamide;
N-Phenethyl-N-(1-methylpiperidin-4-yl)-N'-phenyl-carbamide;
N-(3-Phenylpropyl)-N-(1-methylpiperidin-4-yl)-N'-benzyl-carbamide;
N-(3-Phenylpropyl)-N-(1-methylpiperidin-4-yl)-N'-phenyl-carbamide;
2-(4-Methoxyphenyl)-2,2-ethylene-N-(4-methylbenzyl)-N-(1-methylpiperidin-4-yl)acetamide;
2-(4-Methoxyphenyl)-N-alpha-methylbenzyl-N-(1-methylpiperidin-4-yl)acetamide;
2-(4-Methoxyphenyl)-N-(4-methylbenzyl)-N-(3-tropen-4-yl)acetamide;
2-Phenyl-2-ethyl-N-(4-methylbenzyl)-N-(1-methylpiperidin-4-yl)acetamide;
N-Phenethyl-N-(4-methylbenzyl)-N-(1-methylpiperidin-4-yl)-amine;
2-(4-Methoxyphenyl)-N-(1-indanyl)-N-(1-methylpiperidin-4-yl)acetamide;
N-(4-Methylbenzyl)-N-(1-methylpiperidin-4-yl)-N'-(4-methoxybenzyl)-carbamide;
2-(3,4-dimethoxyphenyl)-N-(4-methylbenzyl)-N-(1-methylpiperidin-4-yl)acetamide;
2-(3,4-Methylenedioxyphenyl)-N-(4-methylbenzyl)-N-(1-methylpiperidin-4-yl)acetamide;
2-(4-Methoxyphenyl)-N-(4-methylbenzyl)-N-(1-t-butylpiperidin-4-yl)-acetamide;
N-(4-Methylbenzyl)-N-(1-methylpiperidin-4-yl)-N'-phenethyl-carbamide;
N-Phenethyl-N-(1-methylpiperidin-4-yl)-N'-phenethyl-carbamide;
N-(4-Methylbenzyl)-N-(1-t-butylpiperidin-4-yl)-N'-(4-methoxybenzyl)-carbamide;
2-(4-Ethoxyphenyl)-N-(4-methylbenzyl)-N-(1-methylpiperidin-4-yl)acetamide;
2-(4-Butoxyphenyl)-N-(4-methylbenzyl)-N-(1-methylpiperidin-4-yl)acetamide;
2-(4-i-Propoxyphenyl)-N-(4-methylbenzyl)-N-(1-methylpiperidin-4-yl)acetamide;
2-(4-t-Butoxyphenyl)-N-(4-methylbenzyl)-N-(1-methylpiperidin-4-yl)acetamide;
2-(4-Butoxyphenyl)-N-(4-fluorobenzyl)-N-(1-methylpiperidin-4-yl)acetamide;
2-(4-Propoxyphenyl)-N-(4-flourobenzyl)-N-(1-methylpiperidin-4-yl)acetamide;
2-(4-i-Propoxyphenyl)-N-(4-fluorobenzyl)-N-(1-methylpiperidin-4-yl)acetamide;
and, 2-(4-t-Butoxyphenyl)-N-(4-fluorobenzyl)-N-(1-methylpiperidin-4-yl)acetamide.

Suitable pharmaceutically acceptable salts of the compounds of this invention include acid addition salts that may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Examples of pharmaceutically acceptable salts include the acetate, benzenesulfonate, benzoate, bicarbonate, bisulfate, bitartrate, borate, bromide, calcium, carbonate, chloride, clavulanate, citrate, dihydrochloride, fumarate, gluconate, glutamate, hydrobromide, hydrochloride, hydroxynaphthoate, iodide, isothionate, lactate, lactobionate, laurate, maleate, mandelate, mesylate, methylbromide, methylnitrate, methylsulfate, nitrate, N-methylglucamine ammonium salt, oleate, oxalate, phosphate/diphosphate, salicylate, stearate, sulfate, succinate, tannate, tartrate, tosylate, triethiodide and valerate salt.

The present invention includes within its scope prodrugs of the compounds of this invention. In general, such prodrugs are inactive derivatives of the compounds of this invention that are readily convertible in vivo into the required compound. Conventional procedures for the selection and preparation of suitable prodrug derivatives are described, for example, in *Design of Prodrugs*, (ed. H. Bundgaard, Elsevier, 1985). Metabolites of these compounds include active species that are produced upon introduction of compounds of this invention into the biological milieu.

Where the compounds according to the invention have at least one chiral center, they may exist as a racemate or as enantiomers. It should be noted that all such isomers and mixtures thereof are included in the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also included in the scope of this invention.

Where the processes for the preparation of the compounds according to the invention give rise to mixtures of stereoisomers, such isomers may be separated by conventional techniques such as preparative chiral chromatography. The compounds may be prepared in racemic form or individual enantiomers may be prepared by stereoselective synthesis or by resolution. The compounds may be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides followed by chromatographic separation and removal of the chiral auxiliary.

Compounds of the present invention may be administered in any of the foregoing compositions and according to dosage regimens established in the art whenever specific pharmacological modification of the activity of monoamine receptors is required.

The present invention also provides pharmaceutical compositions comprising one or more compounds of the invention together with a pharmaceutically acceptable diluent or excipient. Preferably such compositions are in unit dosage forms such as tablets, pills, capsules (including sustained-release or delayed-release formulations), powders, granules, elixirs, tinctures, syrups and emulsions, sterile parenteral solutions or suspensions, aerosol or liquid sprays, drops, ampoules, auto-injector devices or suppositories; for oral, parenteral (e.g., intravenous, intramuscular or subcutaneous), intranasal, sublingual or rectal administration, or for administration by inhalation or insufflation, and may be formulated in an appropriate manner and in accordance with accepted practices such as those disclosed in *Remington's Pharmaceutical Sciences*, (Gennaro, ed., Mack Publishing Co., Easton Pa., 1990, herein incorportated by reference). Alternatively, the compositions may be in sustained-release form suitable. for once-weekly or once-monthly administration; for example, an insoluble salt of the active compound, such as the decanoate salt, may be adapted to provide a depot preparation for intramuscular injection. The present invention also contemplates providing suitable topical formulations for administration to, e.g., eye or skin or mucosa.

For instance, for oral administration in the form of a tablet or capsule, the active drug component can be combined with an oral, non-toxic, pharmaceutically acceptable inert carrier such as ethanol, glycerol, water and the like. Moreover, when desired or necessary, suitable binders, lubricants, disintegrating agents, flavoring agents and coloring agents can also be incorporated into the mixture. Suitable binders include, without limitation, starch, gelatin, natural sugars such as glucose or beta-lactose, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For preparing solid compositions such as tablets, the active ingredient is mixed with a suitable pharmaceutical excipient such as the ones described above and other pharmaceutical diluents, e.g., water, to form a solid preformulation composition containing a homogeneous mixture of a compound of the present invention or a pharmaceutically acceptable salt thereof. By the term "homogeneous" is meant that the active ingredient is dispersed evenly throughout the composition so that the composition may be readily subdivided into equally effective unit dosage forms such as tablets, pills and capsules. The solid preformulation composition may then be subdivided into unit dosage forms of the type described above containing from 0.1 to about 50 mg of the active ingredient of the present invention. The tablets or pills of the present composition may be coated or otherwise compounded to provide a dosage form affording the advantage of prolonged action. For example, the tablet or pill can comprise an inner core containing the active compound and an outer layer as a coating surrounding the core. The outer coating may be an enteric layer that serves to resist disintegration in the stomach and permits the inner core to pass intact into the duodenum or to be delayed in release. A variety of materials can be used for such enteric layers or coatings including a number of polymeric acids and mixtures of polymeric acids with conventional materials such as shellac, cetyl alcohol and cellulose acetate.

The liquid forms in which the present compositions may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical carriers. Suitable dispersing or suspending agents for aqueous suspensions include synthetic and natural gums such as tragacanth, acacia, alginate, dextran, sodium carboxymethylcellulose, gelatin, methylcellulose or polyvinylpyrrolidone. Other dispersing agents that may be employed include glycerin and the like. For parenteral administration, sterile suspensions and solutions are desired. Isotonic preparations that generally contain suitable preservatives are employed when intravenous administration is desired. The compositions can also be formulated as an ophthalmic solution or suspension formation, i.e., eye drops, for ocular administration.

Consequently, the present invention also relates to a method of alleviating or treating a disease condition in which modification of monoamine receptor activity, in particular 5-HT2A serotonergic receptor activity, has a beneficial effect by administering a therapeutically effective amount of a compound of the present invention to a subject in need of such treatment. Such diseases or conditions may, for instance arise from inappropriate stimulation or activation of serotonergic receptors. It is anticipated that by using compounds that are selective for a particular serotonin receptor subtype, in particular 5-HT2A, the problems with adverse side effects observed with the known antipsychotic drugs, such as extrapyramidal effects, may be avoided substantially.

The term "therapeutically effective amount" as used herein means an amount of an active compound or pharmaceutical agent that elicits the biological or medicinal response in a tissue, system, animal or human that is being sought by a researcher, veterinarian, medical doctor or other clinician, which includes alleviation of the symptoms of the disease being treated.

Advantageously, compounds of the present invention may be administered in a single daily dose, or the total daily dosage may be administered in divided doses, for example, two, three or four times daily. Furthermore, compounds of the present invention may be administered in intranasal form via topical use of suitable intranasal vehicles, via transdermal routes, using those forms of transdermal skin patches well known to persons skilled in the art, by implantable pumps; or by any other suitable means of administration. To be administered in the form of a transdermal delivery system, for example, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound employed. A physician or veterinarian of ordinary skill can readily determine and prescribe the effective amount of the drug required to prevent, counter or arrest the progress of the disease or disorder that is being treated.

The daily dosage of the products may be varied over a wide range from about 0.01 mg to about 100 mg per adult human per day. For oral administration, the compositions are preferably provided in the form of tablets containing 0.01, 0.05, 0.1, 0.5, 1.0, 2.5, 5.0, 10.0, 15.0, 25.0 or 50.0 mg of the active ingredient for the symptomatic adjustment of the dosage to the patient to be treated. A unit dose typically contains from about 0.001 mg to about 50 mg of the active ingredient, preferably from about 1 mg to about 10 mg of active ingredient. An effective amount of the drug is ordinarily supplied at a dosage level of from about 0.0001 mg/kg to about 25 mg/kg of body weight per day. Preferably, the range is from about 0.001 to 10 mg/kg of body weight per day, and especially from about 0.001 mg/kg to 1 mg/kg of body weight per day.

Compounds according to the present invention may be used alone at appropriate dosages defined by routine testing in order to obtain optimal pharmacological effect on a monoaminergic receptor, in particular the 5-HT2A serotonergic receptor subtype, while minimizing any potential toxic or otherwise unwanted effects. In addition, co-administration or sequential administration of other agents that improve the effect of the compound may, in some cases, be desirable.

The pharmacological properties and the selectivity of the compounds of this invention for specific serotonergic receptor subtypes may be demonstrated by a number of different assay methods using recombinant receptor subtypes, preferably of the human receptors if these are available, e.g. conventional second messenger or binding assays. A particularly convenient functional assay system is the receptor selection and amplification assay disclosed in U.S. Pat. No. 5,707,798, which describes a method of screening for bioactive compounds by utilizing the ability of cells transfected with receptor DNA, e.g., coding for the different serotonergic subtypes, to amplify in the presence of a ligand of the receptor. Cell amplification is detected as increased levels of a marker also expressed by the cells.

Methods of Preparation

The compounds in accordance with the present invention may be synthesized by methods described below, or by modification of these methods. Ways of modifying the methodology include, among others, temperature, solvent, reagents etc, and will be obvious to those skilled in the art.

For instance, compounds of the formula C may be synthesized from the corresponding ketone A by reductive amination utilizing any primary amine. The reaction is conveniently carried out by stirring the reactants in an inert solvent such as methanol or ethanol containing acetic acid. As reducing agent $NaBH_4$, $NaCNBH_3$, $BH_3$.pyridine or any related reagent may be used including solid-supported reagents. The reaction is typically carried out at room temperature. The ketone A, as exemplified by the piperidone, may be chosen from a list of compounds corresponding to the Z-group listed in formula (I). The ketones can either be obtained commercially or synthesized by methodology disclosed in Lowe et al. *J. Med. Chem.* 37: 2831–40 (1994); Carroll et al. *J. Med. Chem.* 35:2184–91 (1992); or Rubiralta et al. *Piperidine—Structure, Perparation, Reactivity and Synthetic Applications of Piperidine and its Derivatives.* (*Studies in Organic Chemistry* 43, Elsevier, Amsterdam, 1991). The protecting group P includes groups such as those described in T. W. Greene and P. G. M. Wuts, *Protective Groups in Organic Chemistry*, 3. Ed. John Wiley & Sons, 1999, and they should be chosen in such a way, that they are stable to the reaction conditions applied and readily removed at a convenient stage using methodology known from the art. Typical protecting groups are N-Boc, N-Cbz, N-Bn.

Alternatively, the amine C can be synthesized from the primary amine B by reductive amination with any aldehyde. The reaction is conveniently carried out by stirring the reactants in an inert solvent such as methanol or ethanol containing acetic acid. As reducing agent $NaBH_4$, $NaCNBH_3$, $BH_3$.pyridine or any related reagent may be used including solid-supported reagents. The reaction is typically carried out at room temperature. The primary amine B, as exemplified by the 4-aminopiperidine, may be chosen from a list of compounds corresponding to the Z-groups listed in formula (I). The amines can either be obtained commercially or synthesized from the corresponding ketones. The protecting group P may be chosen as stated above.

Alternatively, the amine C can be synthesized from the primary amine B by alkylation with any alkylating agent (R—$L_1$). The leaving group $L_1$ is suitably a halogen atom, e.g., bromine or iodine, or a sulfonate, e.g. tosylate or mesylate, or another leaving group favoring the reaction. The reaction is conveniently carried out by stirring the reagents under basic conditions in an inert solvent, e.g., diisopropylethylamine in acetonitrile, or $K_2CO_3$ in N,N-dimethylformamide. The reaction is typically carried out at temperatures between room temperature and 80° C. The primary amine B, as exemplified by the 4-aminopiperidine, may be chosen from a list of compounds corresponding to the Z-groups listed in formula (I). The amines can either be obtained commercially or synthesized from the corresponding ketones. The protecting group P may be chosen as stated above.

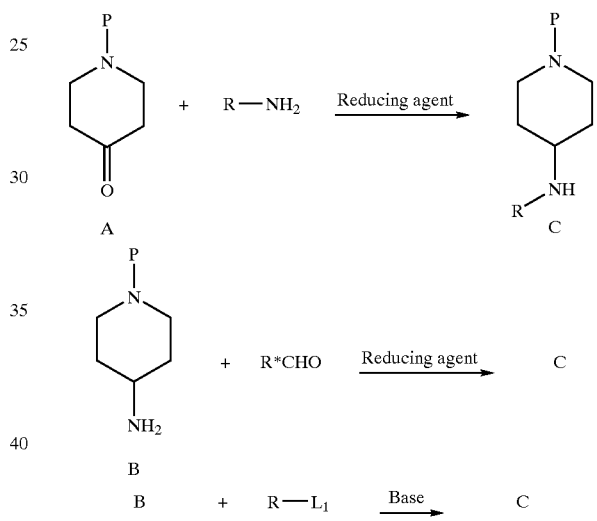

Wherein R and R* are defined in agreement with formula (I), and P represents a suitable protecting group, and $L_1$ represents a suitable leaving group.

The secondary amine C may be acylated using any isocyanate or isothiocyanate ($Q_1$—N=C=W) to give the corresponding ureas or thioureas D. The reaction is typically carried out by stirring the reactants, using an excess of isocyanate or isothiocyanate in an inert solvent, e.g., dichloromethane at a temperature between 0° C. and room temperature and under dry conditions. The amine C may also be acylated using any carboxylic acid halide ($Q_2$COX), e.g., chloride, or carboxylic anhydride (($Q_2$C=O)$_2$O) to give amides of the general structure E. The reaction is typically carried out using an excess of the acylating agent and a suitable base, e.g., triethylamine or diisopropylethylamine in an inert solvent, e.g., dichloromethane, at a temperature between 0° C. and room temperature and under dry conditions. As an alternative to the carboxylic acid halides and carboxylic acid anhydrides, the amine C may be acylated using a carboxylic acid ($Q_2$COOH) and a suitable coupling reagent e.g. DCC or EDCI. The reaction is typically carried out using an excess of the acylating agent and the coupling reagent in an inert solvent, e.g., dichloromethane at a temperature between 0° C. and room temperature and under dry conditions. The compounds of the general structure (E) may be converted into the corresponding thioamides using methodology disclosed in Varma et al., *Org. Lett.* 1: 697–700 (1999); Cherkasov et al. *Tetrahedron* 41:2567 (1985); or Scheibye et al, *Bull. Soc. Chim. Belg.* 87:229 (1978).

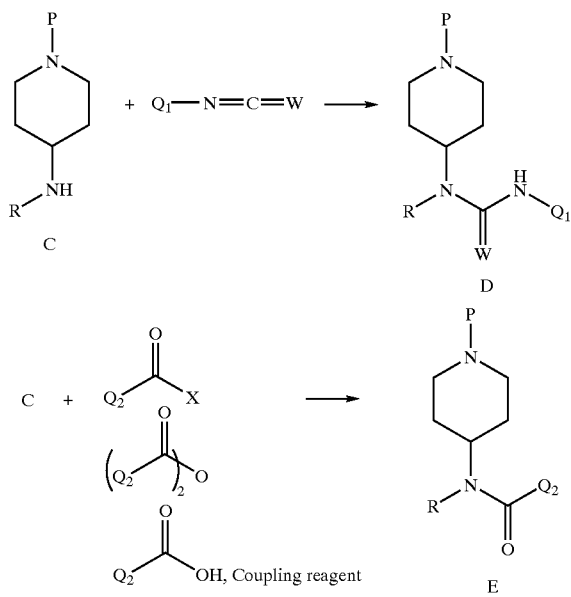

Wherein R, $Q_1$, $Q_2$, and W are defined in agreement with formula (I), P represents a suitable protecting group, and X represents a halide.

The substituent G on the ring nitrogen can be introduced by a two step procedure. First, the protecting group on the urea D or the amide E is removed using well-known methods. For example, the N-Boc group is removed by treating the protected compound with 4 M HCl in dioxane or trifluoroacetic acid in dichloromethane. Second, the secondary amines obtained from D and E can be alkylated by reductive amination using any aldehyde (T—CHO). The reaction is conveniently carried out by stirring the reactants in an inert solvent such as methanol or ethanol. As a reducing agent, solid-supported borohydride, $NaBH_4$, $NaCNBH_3$, $BH_3$·pyridine or any related reagent may be used, including solid-supported reagents. The reaction is typically carried out at room temperature.

Alternatively, the compounds F and G can be synthesized from the secondary amine obtained from D or E as described above by alkylation with any alkylating agent (T—$L_1$). The leaving group $L_1$ is suitably a halogen atom, e.g., bromine or iodine, or a sulfonate, e.g., tosylate or mesylate, or another leaving group favoring the reaction. The reaction is conveniently carried out by stirring the reagents under basic conditions in an inert solvent, for example diisopropylethylamine in acetonitrile, or $K_2CO_3$ in N,N-dimethylformamide. The reaction is typically carried out at temperatures between room temperature and 80° C.

Alternatively, the T-group can be introduced in the first step of the synthetic sequence leading to the compounds in accordance with the present invention by N-alkylation of compound H with any alkylating agent (T—$L_1$). The leaving group $L_1$ is suitably a halogen atom, e.g., bromine or iodine, or a sulfonate, e.g., tosylate or mesylate, or another leaving group favoring the reaction. The reaction is conveniently carried out by stirring the reagent under basic conditions in an inert solvent, e.g., diisopropylethylamine in acetonitrile, or $K_2CO_3$ in N,N-dimethylformamide. The reaction is typically carried out at temperatures between room temperature and 80° C. The secondary amine H, as exemplified by 4-piperidone, may be chosen from a list of compounds corresponding to the Z-groups listed in formula (I). The amines can either be obtained commercially or synthesized from methodology disclosed in Lowe et al., *J. Med. Chem.* 37:2831–40 (1994); and Carroll et al., *J. Med. Chem.* 35:2184–91 (1992).

Alternatively, compounds of the general structure J may be synthesized starting from K using the method disclosed in: Kuehne et al.,*J. Org. Chem.* 56:2701 (1991); and Kuehne et al., *J. Org. Chem.* (1991), 56:513.

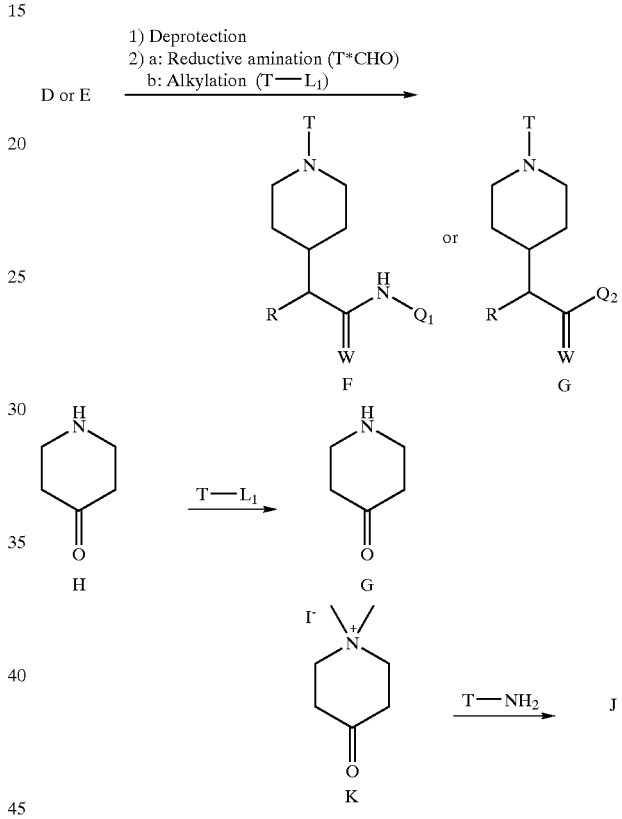

wherein R, $Q_1$, $Q_2$, W, and T are defined in agreement with formula (I), and $L_1$ is a suitable leaving group.

In general, during any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and Greene & Wuts, *Protective Groups in Organic Synthesis*, John Wiley & Sons, 1991. The protecting groups may be removed at a convenient subsequent stage using methods known from the art.

EXAMPLES

The invention is disclosed in further detail in the following examples that are not in any way intended to limit the scope of the invention as claimed.

General LC-MS procedure for Examples 1–41: All spectra were obtained using an HP1100 LC/MSD-instrument. A setup with a binary pump, autosampler, column oven, diode array detector, and electrospray ionization interface was used. A reversed phase column (C18 Luna 3 mm particle size, 7.5 cm×4.6 mm ID) with a guard cartridge system was used. The column was maintained at a temperature of 30° C. The mobile phase was acetonitrile/8 mM aqueous ammonium acetate. A 15 minute gradient program was used, starting at 70% acetonitrile, over 12 minutes to 95% acetonitrile, over 1 minute back to 70% acetonitrile, where it stayed for 2 minutes. The flow rate was 0.6 ml/min. The $t_r$ values reported in the specific examples below were obtained using this procedure.

Example 1

N-((4-Methylphenyl)methyl)-N-(piperidin-4-yl)-N'-phenylmethylcarbamide (26HCH65)

To a solution of commercially available tert-butyl 4-oxo-1-piperidine carboxylate (1.75 g, 8.8 mmol) and 4-methylbenzylamine (970 mg, 8.0 mmol) in methanol (7 ml) was added acetic acid in methanol (1 M, 6.7 ml) followed by NaCNBH$_3$ in methanol (0.3 M, 30 ml). The resulting solution was stirred at room temperature. After 20 h, water (5 ml) was added, and the mixture was stirred for 1 h before it was concentrated. Flash chromatography in dichloromethane:methanol 10:1 gave tert-butyl 4-(4-methylphenyl)methyl)amino-piperidine carboxylate. Yield: 2.4 g, 98%. To a solution of tert-butyl 4-(4-methylphenyl)methyl)amino-piperidine carboxylate (800 mg, 2.63 mmol) in dry dichloromethane (20 ml) was added benzylisocyanate (0.65 ml, 5.26 mmol). The solution was stirred at room temperature. After 48 h, an excess of 2-dimethylaminoethylamine was added. The mixture was stirred for another 24 h, before it was concentrated. The resulting solid was redissolved in dichloromethane (20 ml), sequentially washed with HCl (0.2 N, 3×30 ml), and water (20 ml), dried (Na$_2$SO$_4$), filtered and concentrated. Flash chromatography in dichloromethane:methanol 10:1 gave N-((4-methylphenyl)methyl)-N-(1-(tert-butyloxycarbonyl)piperidin-4-yl)-N'-phenylmethylcarbamide (760 mg, 66%), which was dissolved in diethyl ether (5 ml). HCl (4 M) in dioxane (3 ml) was added, and the solution was stirred at room temperature for 60 min, then concentrated. The resulting oil was redissolved in a mixture of dichloromethane and diethyl ether (4:1). The organic layer was extracted with HCl (0.2 M, 3×20 ml). The combined aqueous layers were treated with NaOH (0.2 M) until basic (pH>8), then extracted with dichloromethane (3×20 ml). The combined organic layers were dried (Na$_2$SO$_4$), filtered, and concentrated to give the title compound. Yield: 406 mg, 70%; $^{13}$C-NMR (CDCl$_3$): δ 21.3, 31.6, 45.0, 45.9, 46.4, 53.0, 126.3, 127.2, 127.4, 128.6, 129.8, 135.3, 137.4, 139.7, 158.5.

Example 2

N-((4-Methylphenyl)methyl)-N-(1-(2-methylpropyl)piperidin-4-yl)-N'-phenylmethylcarbamide (26HCH66-02)

The product from example 1 above (20 mg, 0.06 mmol) was dissolved in abs. ethanol (2 ml). 2-Methylpropionaldehyde (0.08 ml, 0.6 mmol) was added followed by solid-supported borohydride (150 mg, 2.5 mmol/g resin; Aldrich 32,864-2). The mixture was shaken at room temperature. After 48 h, the resin was filtered off and acetic anhydride (0.02 ml, 0.2 mmol) was added to the organic solution. After 24 h, the mixture was concentrated and redissolved in methanol (2 ml). The solution was added on to a column carrying strongly acidic cation exchange resin (0.3 mmol/g resin), which was washed with methanol (3×6 ml), and eluted with 10% NH$_3$ in methanol, and concentrated to give the title compound. IR: 1640, 1185, 1110 cm$^{-1}$; LC-MS: (M+H)$^+$ 394.2, $t_r$ 5.60 min.

Example 3

N-(1-((2-Bromophenyl)methyl)piperidin-4-yl)-N-((4-methylphenyl)methyl)-N'-phenylmethylcarbamide (26HCH66-03)

The product from example 1 above (20 mg, 0.06 mmol) was dissolved in abs. ethanol (2 ml). 2-Bromobenzaldehyde (0.07 ml, 0.6 mmol) was added followed by solid-supported borohydride (150 mg, 2.5 mmol/g resin; Aldrich 32,864-2). The mixture was shaken at room temperature. After 48 h, the resin was filtered off and acetic anhydride (0.02 ml, 0.2 mmol) was added to the organic solution. After 24 h, the mixture was concentrated and redissolved in methanol (2 ml). The solution was added on to a column carrying strongly acidic cation exchange resin (0:3 mmol/g resin), which was washed with methanol (3×6 ml), and eluted with 10% NH$_3$ in methanol, and concentrated to give the title compound. IR: 1635, 1180, 1110 cm$^{-1}$; LC-MS: (M+H)$^+$ 506.1, $t_r$ 8.37 min.

Example 4

N-(1-((4-Hydroxy-3-methoxyphenyl)methyl)piperidin-4-yl)-N-((4-methylphenyl)methyl)-N'-phenylmethylcarbamide (26HCH66-04)

The product from example 1 above (20 mg, 0.06 mmol) was dissolved in abs. ethanol (2 ml). 4-Hydroxy-3-methoxybenzaldehyde (91 mg, 0.6 mmol) was added followed by solid-supported borohydride (150 mg, 2.5 mmol/g resin; Aldrich 32,864-2). The mixture was shaken at room temperature. After 48 h, the resin was filtered off and acetic anhydride (0.02 ml, 0.2 mmol) was added to the organic solution. After 24 h, the mixture was concentrated and redissolved in methanol (2 ml). The solution was added on to a column carrying strongly acidic cation exchange resin (0.3 mmol/g resin), which was washed with methanol (3×6 ml), and eluted with 10% NH$_3$ in methanol, and concentrated to give the title compound. $^{13}$C-NMR (CD$_3$OD, selected): δ 19.9, 55.4, 126.5, 127.0, 128.1, 129.0, 140.3, 148.0, 148.1, 158.8.

Example 5

N-(1-((5-Ethylthien-2-yl)methyl)piperidin-4-yl)-N-((4-methylphenyl)methyl)-N'-phenylmethylcarbamide (26HCH66-05)

The product from example 1 above (20 mg, 0.06 mmol) was dissolved in abs. ethanol (2 ml). 5-Ethyl-2-thiophencarboxaldehyde (84 mg, 0.6 mmol) was added followed by solid-supported borohydride (150 mg, 2.5 mmol/g resin; Aldrich 32,864-2). The mixture was shaken at room temperature. After 48 h, the resin was filtered off and acetic anhydride (0.02 ml, 0.2 mmol) was added to the organic solution. After 24 h, the mixture was concentrated and redissolved in methanol (2 ml). The solution was added on to a column carrying strongly acidic cation exchange resin (0.3 mmol/g resin), which was washed with methanol (3×6 ml), and eluted with 10% NH$_3$ in methanol, and concentrated to give the title compound. IR: 1640, 1185, 1110, 805, 700, 620 cm$^{-1}$; LC-MS: (M+H)$^+$ 462.3, $t_r$ 7.52 min.

Example 6

N-(1-(Imidazol-2-ylmethyl)piperidin-4-yl)-N-((4-methylphenyl)methyl)-N'-phenylmethylcarbamide (26HCH66-06)

The product from example 1 above (20 mg, 0.06 mmol) was dissolved in abs. ethanol (2 ml). Imidazole-2-carboxaldehyde (58 mg, 0.6 mmol) was added followed by solid-supported borohydride (150 mg, 2.5 mmol/g resin; Aldrich 32,864-2). The mixture was shaken at room temperature. After 48 h, the resin was filtered off and acetic anhydride (0.02 ml, 0.2 mmol) was added to the organic solution. After 24 h, the mixture was concentrated and redissolved in methanol (2 ml). The solution was added on to a column carrying strongly acidic cation exchange resin (0.3 mmol/g resin), which was washed with methanol (3×6 ml), and eluted with 10% $NH_3$ in methanol, and concentrated to give the title compound. IR: 1620, 1190, 1100, 805, 700, 620 $cm^{-1}$; LC-MS: $(M+H)^+$ 418.2, $t_r$ 2.05 min.

Example 7

N-(1-(Cyclohexylmethyl)piperidin-4-yl)-N-((4-methylphenyl)methyl)-N'-phenylmethylcarbamide (26HCH66-09)

The product from example 1 above (20 mg, 0.06 mmol) was dissolved in abs. ethanol (2 ml). Cyclohexanecarboxaldehyde (67 mg, 0.6 mmol) was added followed by solid-supported borohydride (150 mg, 2.5 mmol/g resin; Aldrich 32,864-2). The mixture was shaken at room temperature. After 48 h, the resin was filtered off and acetic anhydride (0.02 ml, 0.2 mmol) was added to the organic solution. After 24 h, the mixture was concentrated and redissolved in methanol (2 ml). The solution was added on to a column carrying strongly acidic cation exchange resin (0.3 mmol/g resin), which was washed with methanol (3×6 ml), and eluted with 10% $NH_3$ in methanol, and concentrated to give the title compound. IR: 1635, 1175, 1100, 805, 695, 620 $cm^{-1}$; LC-MS: $(M+H)^+$ 434.4, $t_r$ 7.44 min.

Example 8

N-(1-((4-Fluorophenyl)methyl)piperidin-4-yl)-N-((4-methylphenyl)methyl)-N'-phenylmethylcarbamide (26HCH66-10)

The product from example 1 above (20 mg, 0.06 mmol) was dissolved in abs. ethanol (2 ml). 4-Fluorobenzaldehyde (0.08 ml, 0.6 mmol) was added followed by solid-supported borohydride (150 mg, 2.5 mmol/g resin; Aldrich 32,864-2). The mixture was shaken at room temperature. After 48 h, the resin was filtered off and acetic anhydride (0.02 ml, 0.2 mmol) was added to the organic solution. After 24 h, the mixture was concentrated and redissolved in methanol (2 ml). The solution was added on to a column carrying strongly acidic cation exchange resin (0.3 mmol/g resin), which was washed with methanol (3×6 ml), and eluted with 10% $NH_3$ in methanol, and concentrated to give the title compound. IR: 1640, 1175, 1110, 805, 700, 620 $cm^{-1}$; LC-MS: $(M+H)^+$ 446.3, $t_r$ 5.62 min.

Example 9

N-((4-Methylphenyl)methyl)-N-(1-(phenylmethyl)piperidin-4-yl)-N'-phenylmethylcarbamide hydrochloride (26HCH16D)

To a solution of 1-benzyl-4-piperidone (1.74 g, 9.2 mmol) and 4-methylbenzylamine (0.97 g, 8 mmol) in methanol (30 ml) was added sodium borohydride (525 mg) in small portions over 30 min. The reaction mixture was stirred at room temperature. After 16 h, the mixture was concentrated. Water (30 ml) was added, and the mixture was extracted with dichloromethane (2×20 ml). The combined organic layers were dried ($Na_2SO_4$), filtered, and concentrated to give 4-((4-methylphenyl)methyl)amino-1-phenylmethylpiperidine. The crude product was used without further purification.

4-((4-Methylphenyl)methyl)amino-1-phenylmethylpiperidine (800 mg, 2.7 mmol) was dissolved in dry dichloromethane (30 ml). Benzylisocyanate (543 mg, 4.1 mmol) was added. The reaction mixture was stirred at room temperature. After 16 h, water (10 ml) was added followed by NaOH (6 N, 2 ml). After additional 30 minutes of stirring the white crystals were filtered off. The organic layer was isolated and dried ($Na_2SO_4$), filtered, and concentrated. Flash chromatography in dichloromethane/methanol 10/1 left N-((4-Methylphenyl)methyl)-N-(1-(phenylmethyl)piperidin-4-yl)-N'-phenylmethylcarbamide Yield: 820 mg, 71%; A sample was concentrated with HCl (4 M in dioxane) followed by recrystallization from dichloromethane/diethyl ether leaving the title compound. $^1$H-NMR ($CDCl_3$): δ 1.87 (brd, 2 H), 2.30 (s, 3 H), 2.59 (dq, 2 H), 2.76 (br q, 2 H), 3.44 (br d, 2 H), 4.09 (d, 2 H), 4.30 (d, 2 H), 4.40 (s, 2 H), 4.64–4.76 (m, 2 H), 6.98–7.64 (Aromatic protons, 14 H); $^{13}$C-NMR ($CDCl_3$): δ 21.2, 26.7, 45.0, 46.0, 49.7, 52.2, 61.0, 126.2, 127.26, 126.31, 128.2, 128.6, 129.6, 129.9, 130.4, 131.6, 134.4, 137.6, 139.3, 158.5; $^{13}$C-NMR ($CD_3OD$, rotamers): δ 19.8, 26.4, 27.8, 40.3, 44.3, 51.6, 51.9, 54.5, 60.5, 110.0, 112.1, 114.0, 114.2, 117.5, 125.9, 126.2, 126.7, 126.8, 128.9, 129.1, 129.2, 129.4, 129.7, 130.1, 131.2, 134.5, 137.4, 159.1, 173.8, 175.0; Mp. 109–112° C.; Elemental analysis: Found C, 70.06; H, 7.62; N, 8.60; calcd for monohydrate: C, 69.76; H, 7.53; N, 8.72.

Example 10

N-((4-Methylphenyl)methyl)-N-(1-(phenylmethyl)piperidin-4-yl)-N'-phenylmethylcarbamide oxalate (34JJ59oxal)

N-((4-Methylphenyl)methyl)-N-(1-(phenylmethyl)piperidin-4-yl)-N'-phenylmethylcarbamide was prepared as described in example 9 above. A sample was precipitated as the oxalate and recrystallized from ethyl acetate to give the title compound. $^{13}$C-NMR ($CDCl_3$): δ 21.2, 27.0, 45.0, 45.9, 49.9, 52.1, 60.6, 126.1, 127.3, 127.4, 128.5, 128.7, 129.6, 130.0, 130.4, 131.2, 134.3, 137.7, 139.3, 158.4, 163.4; Mp. 180–182° C.; Elemental analysis: Found C, 69.54; H, 6.73; N, 7.96; calcd for monooxalate: C, 69.61; H, 6.82; N, 8.12.

Example 11

N-((4-Methylphenyl)methyl)-N-(1-(phenylmethyl)piperidin-4-yl)-4-methoxyphenylacetamide hydrochloride (26HCH17)

To a solution of 1-benzyl-4-piperidone (1.74 g, 9.2 mmol) and 4-methylbenzylamine (0.97 g, 8 mmol) in methanol (30 ml) was added sodium borohydride (525 mg) in small portions over 30 min. The reaction mixture was stirred at room temperature. After 16 h, the mixture was concentrated. Water (30 ml) was added, and the mixture was extracted with dichloromethane (2×20 ml). The combined organic layers were dried ($Na_2SO_4$), filtered, and concentrated to give 4-((4-methylphenyl)methyl)amino-1-phenylmethylpiperidine. The crude product was used without further purification.

To a solution of 4-((4-Methylphenyl)methyl)amino-1-phenylmethylpiperidine (800 mg, 2.7 mmol) in dry dichloromethane (30 ml) was added diisopropylethylamine (1.5 ml)followed by 4-methoxyphenylacetyl chloride (997 mg, 5.4 mmol). The reaction mixture was stirred at room temperature. After 16 h, the reaction mixture was concentrated, redissolved in diethyl ether, and extracted with HCl (0.6 N). The aqueous layer was isolated, treated with NaOH (1 N)until basic, and extracted with dichloromethane (20 ml). The organic layer was isolated and dried ($Na_2SO_4$), filtered, and concentrated, and redissolved in diethyl ether. The hydrochloride was formed by addition of HCl (4 M in dioxane), and recrystallized from diethyl ether to give the title compound. Yield: 600 mg, 50%; $^1$H-NMR ($CDCl_3$): δ 1.75 (d, 2 H), 2.32 (s, 3 H), 2.50 (q, 2 H), 2.70 (q, 2 H), 3.38 (d, 2 H), 3.54 (s, 2 H), 3.78 (s, 3 H), 4.06 (d, 2 H), 4.54 (s, 2 H), 4.82 (m, 1 H), 6.78–7.60 (aromatic protons, 13 H); $^{13}$C-NMR ($CDCl_3$): δ 21.0, 26.0, 40.3, 46.3, 49.0, 51.8, 55.3, 60.8, 114.2, 125.6, 126.6, 127.9, 129.4, 129.60, 129.62, 130.3, 131.4, 134.8, 137.1, 158.7, 172.9; Mp. 197–200° C.; Elemental analysis: Found C, 71.29; H, 7.25; N, 5.73; calcd for hydrate: C, 71.37; H, 7.43; N, 5.74.

Example 12

N-((4-Methylphenyl)methyl)-N-(1-(phenylmethyl)piperidin-4-yl)-4-methoxyphenylacetamide oxalate (34JJ61oxal)

N-((4-Methylphenyl)methyl)-N-(1-(phenylmethyl)piperidin-4-yl)-4-methoxyphenylacetamide was prepared as described in example 11 above. A sample was precipitated as the oxalate and recrystallized from tetrahydrofuran to give the title compound. $^{13}$C-NMR ($CDCl_3$): δ 21.2, 26.4, 40.6, 52.0, 55.5, 114.4, 125.9, 126.7, 128.4, 129.6, 129.8, 129.9, 130.4, 131.2, 134.6, 137.6, 158.9, 163.3, 172.9; Mp. 171–173° C.; Elemental analysis: Found C, 69.56; H, 6.74; N, 5.16; calcd for monooxalate: C, 69.48; H, 6.61; N, 5.40.

Example 13

N-((4-Methylphenyl)methyl)-N-(piperidin-4-yl)-4-methoxyphenylacetamide (26HCH71B)

To a solution of commercially available tert-butyl 4-oxo-1-piperidine carboxylate (1.75 g, 8.8 mmol) and 4-methylbenzylamine (970 mg, 8.0 mmol) in methanol (7 ml) was added acetic acid in methanol (1 M, 6.7 ml) followed by $NaCNBH_3$ in methanol (0.3 M, 30 ml). The resulting solution was stirred at room temperature. After 20 h, water (5 ml) was added, and the mixture was stirred for 1 h before it was concentrated. Flash chromatography in dichloromethane:methanol 10:1 gave tert-butyl 4-(4-methylphenyl)methyl)amino-piperidine carboxylate. Yield: 2.4 g, 98%. To a solution of tert-butyl 4-(4-methylphenyl)methyl)amino-piperidine carboxylate (862 mg, 2.83 mmol) in dry dichloromethane (10 ml) was added diisopropylethylamine (1.1 ml, 6.5 mmol) followed by 4-methoxyphenylacetyl chloride (0.66 ml, 4.3 mmol). The reaction mixture was stirred at room temperature. After 48 h, water (5 ml) was added, and the mixture was stirred for additional 2 h before extracted with NaOH (0.2 N, 2×15 ml), HCl (0.2 N, 2×15 ml), and water (15 ml). The organic layer was dried ($Na_2SO_4$) and concentrated to give N-((4-methylphenyl)methyl)-N-(1-(tert-butyloxycarbonyl)piperidin-4-yl)-4-methoxyphenylacetamide. The crude product was used without any further purification. N-((4-Methylphenyl)methyl)-N-(1-(tert-butyloxycarbonyl)piperidin-4-yl)-4-methoxyphenylacetamide was dissolved in ether (2 ml) and HCl (3 ml, 4 M in dioxane) was added. The reaction mixture was stirred at room temperature. After 2 h, water (5 ml) was added, and the mixture was extracted with HCl (0.1 N, 3×30 ml). The combined aqueous layers were treated with NaOH (0.2 N) until basic (pH >8). The aqueous layer was extracted with diethyl ether (2×20 ml). The combined organic layers were dried ($Na_2SO_4$) and concentrated, before dissolved in methanol (2 ml). The solution was added on to a column carrying strongly acidic cation exchange resin (0.3 mmol/g resin), which was washed with methanol (3×6 ml), and eluted with 10% $NH_3$ in methanol, and concentrated. Additional flash chromatography in dichloromethane/methanol 1/1→methanol containing 2% NH3 gave the title compound. Yield: 466 mg, 47%; $^{13}$C-NMR ($CD_3OD$, rotamers): δ 19.9, 27.8, 29.7, 40.2, 40.3, 44.4, 44.45, 44.50, 52.4, 54.5, 55.5, 114.0, 114.1, 126.0, 126.7, 126.9, 127.3, 128.7, 129.3, 129.6, 129.7, 135.1, 136.1, 136.2, 137.1, 159.0, 159.1, 173.1, 173.7.

Example 14

N-(1-(3,3-Dimethylbutyl)piperidin-4-yl)-N-((4-methylphenyl)methyl)-4-methoxyphenylacetamide (26HCH79-5)

The product from example 13 above (20 mg, 0.06 mmol) was dissolved in abs. ethanol (2 ml). 3,3-Dimethylbutyraldehyde (0.143 ml, 1.1 mmol) was added followed by solid-supported borohydride (150 mg, 2.5 mmol/g resin; Aldrich 32,864-2). The mixture was shaken at room temperature. After 48 h, the resin was filtered off and acetic anhydride (0.02 ml, 0.2 mmol) was added to the organic solution. After 24 h, the mixture was concentrated and redissolved in methanol (2 ml). The solution was added on to a column carrying strongly acidic cation exchange resin (0.3 mmol/g resin), which was washed with methanol (3×6 ml), and eluted with 10% $NH_3$ in methanol, and concentrated to give the title compound. Yield: 26 mg; $^{13}$C-NMR ($CD_3OD$, rotamers): δ 19.9, 27.4, 28.4, 28.8, 29.2, 29.3, 38.3, 38.4, 40.2, 40.3, 44.3, 52.0, 52.3, 52.4, 53.9, 54.6, 54.9, 114.0, 114.1, 126.0, 126.8, 127.0, 127.3, 128.8, 129.4, 129.8, 129.9, 135.0, 136.1, 136.3, 137.1, 158.96, 159.05, 173.2, 173.8.

Example 15

N-(1-(Cyclohexylmethyl)piperidin-4-yl)-N-((4-methylphenyl)methyl)-4-methoxyphenylacetamide (26HCH79-6)

The product from example 13 above (20 mg, 0.06 mmol) was dissolved in abs. ethanol (2 ml). Cyclohexanecarboxaldehyde (0.138 ml, 1.1 mmol) was added followed by solid-supported borohydride (150 mg, 2.5 mmol/g resin; Aldrich 32,864-2). The mixture was shaken at room temperature. After 48 h, the resin was filtered off and acetic anhydride (0.02 ml, 0.2 mmol) was added to the organic solution. After 24 h, the mixture was concentrated and redissolved in methanol (2 ml). The solution was added on to a column carrying strongly acidic cation exchange resin (0.3 mmol/g resin), which was washed with methanol (3×6 ml), and eluted with 10% $NH_3$ in methanol, and concentrated to give the title compound. Yield: 17 mg; HRMS ($FAB^+$, NBA) $(M+H)^+$ 449.3163, $C_{29}H_{41}N_2O_2$ requires 449.3168; LC-MS: $(M+H)^+$ 449.2, $t_r$ 7.92 min.

Example 16

N-((4-Methylphenyl)methyl)-N-(1-(2-methylpropyl)piperidin-4-yl)-4-methoxyphenylacetamide (26HCH79-7)

The product from example 13 above (20 mg, 0.06 mmol) was dissolved in abs. ethanol (2 ml).).

2-Methylpropionaldehyde (0.104 ml, 1.1 mmol) was added followed by solid-supported borohydride (150 mg, 2.5 mmol/g resin; Aldrich 32,864-2). The mixture was shaken at room temperature. After 48 h, the resin was filtered off and acetic anhydride (0.02 ml, 0.2 mmol) was added to the organic solution. After 24 h, the mixture was concentrated and redissolved in methanol (2 ml). The solution was added on to a column carrying strongly acidic cation exchange resin (0.3 mmol/g resin), which was washed with methanol (3×6 ml), and eluted with 10% $NH_3$ in methanol, and concentrated to give the title compound. Yield: 19 mg; HRMS (FAB+, NBA) (M+H)+ 09.2858, $C_{26}H_{37}N_2O_2$ requires 409.2855; LC-MS: (M+H)+ 409.2, $t_r$ 5.97 min.

Example 17

N-((4-Methylphenyl)methyl)-N-(1-((4-methylphenyl)methyl)piperidin-4-yl)-4-methoxyphenylacetamide (26HCH79-8)

The product from example 13 above (20 mg, 0.06 mmol) was dissolved in abs. ethanol (2 ml). 4-Methylbenzaldehyde (0.134 ml, 1.1 mmol) was added followed by solid-supported borohydride (150 mg, 2.5 mmol/g resin; Aldrich 32,864-2). The mixture was shaken at room temperature. After 48 h, the resin was filtered off and acetic anhydride (0.02 ml, 0.2 mmol) was added to the organic solution. After 24 h, the mixture was concentrated and redissolved in methanol (2 ml). The solution was added on to a column carrying strongly acidic cation exchange resin (0.3 mmol/g resin), which was washed with methanol (3×6 ml), and eluted with 10% $NH_3$ in methanol, and concentrated to give the title compound. Yield: 22 mg; HRMS (FAB+, NBA) (M+H)+ 457.2853, $C_{30}H_{37}N_2O_2$ requires 457.2855; LC-MS: (M+H)+ 457.2, $t_r$ 6.97 min.

Example 18

N-(1-((4-Hydroxyphenyl)methyl)piperidin-4-yl)-N-((4-methylphenyl)methyl)-4-methoxyphenylacetamide (26HCH79-9)

The product from example 13 above (20 mg, 0.06 mmol) was dissolved in abs. ethanol (2 ml). 4-Hydroxybenzaldehyde (139 mg, 1.1 mmol) was added followed by solid-supported borohydride (150 mg, 2.5 mmol/g resin; Aldrich 32,864-2). The mixture was shaken at room temperature. After 48 h, the resin was filtered off and acetic anhydride (0.02 ml, 0.2 mmol) was added to the organic solution. After 24 h, the mixture was concentrated and redissolved in methanol (2 ml). The solution was added on to a column carrying strongly acidic cation exchange resin (0.3 mmol/g resin), which was washed with methanol (3×6 ml), and eluted with 10% $NH_3$ in methanol, and concentrated to give the title compound. Yield: 19 mg; HRMS (FAB30, NBA) (M+H)+ 459.2655, $C_{29}H_{35}N_2O_3$ requires 459.2648; LC-MS: (M+H)+ 459.2, $t_r$ 2.84 min.

Example 19

N-(1-((2-Hydroxyphenyl)methyl)piperidin-4-yl)-N-((4-methylphenyl)methyl)-4-methoxyphenylacetamide (26HCH79-10)

The product from example 13 above (20 mg, 0.06 mmol) was dissolved in abs. ethanol (2 ml). 2-Hydroxybenzaldehyde (0.122 ml, 1.1 mmol) was added followed by solid-supported borohydride (150 mg, 2.5 mmol/g resin; Aldrich 32,864-2). The mixture was shaken at room temperature. After 48 h, the resin was filtered off and acetic anhydride (0.02 ml, 0.2 mmol) was added to the organic solution. After 24 h, the mixture was concentrated and redissolved in methanol (2 ml). The solution was added on to a column carrying strongly acidic cation exchange resin (0.3 mmol/g resin), which was washed with methanol (3×6 ml), and eluted with 10% $NH_3$ in methanol, and concentrated to give the title compound. Yield: 16 mg; HRMS (FAB30, NBA) (M+H)+ 459.2633, $C_{29}H_{35}N_2O_3$ requires 459.2648; LC-MS: (M+H)+ 459.2, $t_r$ 5.81 min.

Example 20

N-(3-Phenylpropyl)-N-(piperidin-4-yl)-4-methoxyphenylacetamide (26HCH80-1)

To a solution of commercially available tert-butyl 4-oxo-1-piperidine carboxylate (400 mg, 2 mmol) in methanol (1 ml) and 3-phenylpropylamine (0.143 ml, 1 mmol) in methanol (1 ml) was added acetic acid in methanol (1 M, 1.34 ml) followed by $NaCNBH_3$ in methanol (0.3 M, 4.4 ml). The resulting solution was stirred at room temperature. After 24 h, water (2 ml) was added, and the mixture was stirred for 1 h, before it was concentrated. The resulting oil was redissolved in diethyl ether (20 ml), extracted with HCl (0.1 N, 1×15 ml). The aqueous layer was washed with diethyl ether (10 ml) and treated with 0.2 N NaOH until basic (pH>8), before extracted with dichloromethane (20 ml). The organic layer was dried ($Na_2SO_4$), filtered, and concentrated to give tert-butyl 4-(3-phenylpropyl)amino-piperidine carboxylate. Yield: 110 mg. To a solution of tert-butyl 4-(3-phenylpropyl)amino-piperidine carboxylate (50 mg, 0.16 mmol) in dichloromethane (6 ml) was added diisopropylethylamine (0.070 ml, 0.4 mmol) followed by 4-methoxyphenylacetyl chloride (0.055 ml, 0.35 mmol). The reaction mixture was stirred at room temperature. After 18 h, water (2 ml) was added. The mixture was stirred for another 2 h. The mixture was sequentially washed with HCl (0.2 N, 2×15 ml), NaOH (0.2 N, 2×15 ml), and water (10 ml), dried ($Na_2SO_4$), filtered and concentrated to give N-(3-phenylpropyl)-N-(1-(tert-butyloxycarbonyl)piperidin-4-yl)-4-methoxyphenylacetamide. The crude product was used without any further purification. N-(3-Phenylpropyl)-N-(1-(tert-butyloxycarbonyl)piperidin-4-yl)-4-methoxyphenylacetamide was dissolved in diethyl ether (2 ml) and HCl (1 ml, 4 M in dioxane) was added. The reaction mixture was stirred at room temperature. After 2.5 h, NaOH (1 ml, 6 N) was added followed by dichloromethane (10 ml). The mixture was extracted with water (2×15 ml), dried ($Na_2SO_4$), filtered to give a clear solution. The solution was added on to a column carrying strongly acidic cation exchange resin (0.3 mmol/g resin), which was washed with methanol (3×6 ml), and eluted with 10% $NH_3$ in methanol, and concentrated to give the title compound. Yield: 61 mg; $^{13}$C-NMR ($CD_3OD$, rotamers): δ 27.8, 29.4, 30.8, 32.3, 32.7, 33.3, 40.2, 40.5, 42.0, 44.5, 44.6, 44.9, 52.7, 54.56, 54.57, 54.9, 114.0, 114.1, 125.7, 126.1, 127.0, 127.4, 128.2, 128.3, 128.5, 129.47, 129.55, 141.2, 141.8, 158.9, 159.0, 172.5, 172.7.

Example 21

N-(2-Phenylethyl)-N-(piperidin-4-yl)-4-methoxyphenylmethylacetamide (26HCH80-2)

To a solution of commercially available tert-butyl 4-oxo-1-piperidine carboxylate (400 mg, 2 mmol) in methanol (1 ml) and 2-phenylethylamine (0.143 ml, 1 mmol) in methanol (1 ml) was added acetic acid in methanol (1 M, 1.34 ml)

followed by NaCNBH₃ in methanol (0.3 M, 4.4 ml). The resulting solution was stirred at room temperature. After 24 h, water (2 ml) was added, and the mixture was stirred for 1 h, before it was concentrated. The resulting oil was redissolved in diethyl ether (20 ml), extracted with HCl (0.1 N, 1×15 ml). The aqueous layer was washed with diethyl ether (10 ml) and treated with 0.2 N NaOH until basic (pH>8), before extracted with dichloromethane (20 ml). The organic layer was dried (Na₂SO₄), filtered, and concentrated to give tert-butyl 4-(2-phenylethyl)amino-piperidine carboxylate. Yield: 221 mg. To a solution of tert-butyl 4-(2-phenylethyl)amino-piperidine carboxylate (50 mg, 0.16 mmol) in dichloromethane (6 ml) was added diisopropylethylamine (0.070 ml, 0.4 mmol) followed by 4-methoxyphenylacetyl chloride (0.055 ml, 0.35 mmol). The reaction mixture was stirred at room temperature. After 18 h, water (2 ml) was added. The mixture was stirred for another 2 h. The mixture was sequentially washed with HCl (0.2 N, 2×15 ml), NaOH (0.2 N, 2×15 ml), and water (10 ml), dried (Na₂SO₄), filtered and concentrated to give N-(2-phenylethyl)-N-(1-(tert-butyloxycarbonyl)piperidin-4-yl)-4-methoxyphenylacetamide. The crude product was used without any further purification. N-(2-Phenylethyl)-N-(1-(tert-butyloxycarbonyl)piperidin-4-yl)-4-methoxyphenylacetamide was dissolved in diethyl ether (2 ml) and HCl (1 ml, 4 M in dioxane) was added. The reaction mixture was stirred at room temperature. After 2.5 h, NaOH (1 ml, 6 N) was added followed by dichloromethane (10 ml). The mixture was extracted with water (2×15 ml), dried (Na₂SO₄), filtered to give a clear solution. The solution was added on to a column carrying strongly acidic cation exchange resin (0.3 mmol/g resin), which was washed with methanol (3×6 ml), and eluted with 10% NH₃ in methanol, and concentrated to give the title compound. Yield: 52 mg; $^{13}$C-NMR (CD₃OD, rotamers): δ 27.1, 28.5, 34.9, 36.6, 40.2, 40.4, 44.1, 44.2, 44.4, 53.3, 54.2, 54.6, 114.0, 114.1, 126.2, 126.6, 127.2, 127.4, 128.3, 128.6, 128.79, 128.82, 129.7, 138.5, 139.5, 158.96, 159.0, 172.7, 173.1

Example 22

N-((2-Methoxyphenyl)methyl)-N-(piperidin-4-yl)-4-methoxyphenylmethylacetamide (26HCH80-4)

To a solution of commercially available tert-butyl 4-oxo-1-piperidine carboxylate (400 mg, 2 mmol) in methanol (1 ml) and 2-methoxybenzylamine (0.130 ml, 1 mmol) in methanol (1 ml) was added acetic acid in methanol (1 M, 1.34 ml) followed by NaCNBH₃ in methanol (0.3 M, 4.4 ml). The resulting solution was stirred at room temperature. After 24 h, water (2 ml) was added, and the mixture was stirred for 1 h, before it was concentrated. The resulting oil was redissolved in diethyl ether (20 ml), extracted with HCl (0.1 N, 1×15 ml). The aqueous layer was washed with diethyl ether (10 ml) and treated with 0.2 N NaOH until basic (pH>8), before extracted with dichloromethane (20 ml). The organic layer was dried (Na₂SO₄), filtered, and concentrated to give tert-butyl 4-((2-methoxyphenyl)methyl)amino-piperidine carboxylate. Yield: 211 mg. To a solution of tert-butyl 4-((2-methoxyphenyl)methyl)amino-piperidine carboxylate (50 mg, 0.16 mmol) in dichloromethane (6 ml) was added diisopropylethylamine (0.070 ml, 0.4 mmol) followed by 4-methoxyphenylacetyl chloride (0.055 ml, 0.35 mmol). The reaction mixture was stirred at room temperature. After 18 h, water (2 ml) was added. The mixture was stirred for another 2 h. The mixture was sequentially washed with HCl (0.2 N, 2×15 ml), NaOH (0.2 N, 2×15 ml), and water (10 ml), dried (Na₂SO₄), filtered and concentrated to give N-((2-methoxyphenyl)methyl)-N-(1-(tert-butyloxycarbonyl)piperidin-4-yl)-4-methoxyphenylacetamide. The crude product was used without any further purification. N-((2-Methoxyphenyl)methyl)-N-(1-(tert-butyloxycarbonyl)piperidin-4-yl)-4-methoxyphenylacetamide was dissolved in diethyl ether (2 ml) and HCl (1 ml, 4 M in dioxane) was added. The reaction mixture was stirred at room temperature. After 2.5 h, NaOH (1 ml, 6 N) was added followed by dichloromethane (10 ml). The mixture was extracted with water (2×15 ml), dried (Na₂SO₄), filtered to give a clear solution. The solution was added on to a column carrying strongly acidic cation exchange resin (0.3 mmol/g resin), which was washed with methanol (3×6 ml), and eluted with 10% NH₃ in methanol, and concentrated to give the title compound. Yield: 40 mg; $^{13}$C-NMR (CD₃OD, rotamers): δ 26.1, 27.4, 40.0, 40.1, 43.5, 43.9, 51.5, 53.4, 54.5, 54.58, 54.63, 54.78, 54.83, 110.1, 110.5, 113.76, 113.78, 113.84, 114.0, 114.1, 120.1, 120.5, 125.4, 126.0, 126.5, 126.7, 127.1, 127.3, 127.7, 128.8, 129.8, 130.0, 130.08, 130.14, 156.5, 157.0, 159.0, 159.1, 173.2, 173.8.

Example 23

N-((2-Chlorophenyl)methyl)-N-(piperidin-4-yl)-4-methoxyphenylacetamide (26HCH80-5)

To a solution of commercially available tert-butyl 4-oxo-1-piperidine carboxylate (400 mg, 2 mmol) in methanol (1 ml) and 2-chlorobenzylamine (0.121 ml, 1 mmol) in methanol (1 ml) was added acetic acid in methanol (1 M, 1.34 ml) followed by NaCNBH₃ in methanol (0.3 M, 4.4 ml). The resulting solution was stirred at room temperature. After 24 h, water (2 ml) was added, and the mixture was stirred for 1 h before it was concentrated. The resulting oil was redissolved in diethyl ether (20 ml), extracted with HCl (0.1 N, 1×15 ml). The aqueous layer was washed with diethyl ether (10 ml) and treated with 0.2 N NaOH until basic (pH>8), before extracted with dichloromethane (20 ml). The organic layer was dried (Na₂SO₄), filtered, and concentrated to give tert-butyl 4-((2-chlorophenyl)methyl)amino-piperidine carboxylate. Yield: 137 mg. To a solution of tert-butyl 4-((2-chlorophenyl)methyl)amino-piperidine carboxylate (50 mg, 0.15 mmol) in dichloromethane (6 ml) was added diisopropylethylamine (0.070 ml, 0.4 mmol) followed by 4-methoxyphenylacetyl chloride (0.055 ml, 0.35 mmol). The reaction mixture was stirred at room temperature. After 18 h, water (2 ml) was added. The mixture was stirred for another 2 h. The mixture was sequentially washed with HCl (0.2 N, 2×15 ml), NaOH (0.2 N, 2×15 ml), and water (10 ml), dried (Na₂SO₄), filtered and concentrated to give N-((2-chlorophenyl)methyl)-N-(1-(tert-butyloxycarbonyl)piperidin-4-yl)-4-methoxyphenylacetamide. The crude product was used without any further purification. N-((2-Chlorophenyl)methyl)-N-(1-(tert-butyloxycarbonyl)piperidin-4-yl)-4-methoxyphenylacetamide was dissolved in diethyl ether (2 ml) and HCl (1 ml, 4 M in dioxane) was added. The reaction mixture was stirred at room temperature. After 2.5 h, NaOH (1 ml, 6 N) was added followed by dichloromethane (10 ml). The mixture was extracted with water (2×15 ml), dried (Na₂SO₄), filtered to give a clear solution. The solution was added on to a column carrying strongly acidic cation exchange resin (0.3 mmol/g resin), which was washed with methanol (3×6 ml), and eluted with 10% NH₃ in methanol, and concentrated to give the title compound. Yield: 45 mg; $^{13}$C-NMR (CD₃OD, rotamers): δ 25.8, 26.9, 40.0, 40.1, 42.9, 43.4, 43.7, 46.0, 51.1, 53.0, 54.6, 113.77, 113.84, 114.0, 114.1, 126.6, 126.8, 127.08, 127.13, 127.3, 127.4, 128.1, 129.0, 129.2, 129.8, 130.0, 130.2, 131.9, 132.2, 135.0, 135.3, 159.1, 173.4, 173.8.

Example 24

N-((3,4-Di-methoxyphenyl)methyl)-N-(piperidin-4-yl)-4-methoxyphenylacetamide (26HCH80-6)

To a solution of commercially available tert-butyl 4-oxo-1-piperidine carboxylate (400 mg, 2 mmol) in methanol (1 ml) and 3,4-di-methoxybenzylamine (0.151 ml, 1 mmol) in methanol (1 ml) was added acetic acid in methanol (1 M, 1.34 ml) followed by NaCNBH$_3$ in methanol (0.3 M, 4.4 ml). The resulting solution was stirred at room temperature. After 24 h, water (2 ml) was added. and the mixture was stirred for 1 h, before it was concentrated. The resulting oil was redissolved in diethyl ether (20 ml), extracted with HCl (0.1 N, 1×15 ml). The aqueous layer was washed with diethyl ether (10 ml) and treated with 0.2 N NaOH until basic (pH>8), before extracted with dichloromethane (20 ml). The organic layer was dried (Na$_2$SO$_4$), filtered, and concentrated to give tert-butyl 4-((3,4-di-methoxyphenyl)methyl)amino-piperidine carboxylate. Yield: 162 mg. To a solution of tert-butyl 4-((3,4-di-methoxyphenyl)methyl)amino-piperidine carboxylate (50 mg, 0.14 mmol) in dichloromethane (6 ml) was added diisopropylethylamine (0.070 ml, 0.4 mmol) followed by 4-methoxyphenylacetyl chloride (0.055 ml, 0.35 mmol). The reaction mixture was stirred at room temperature. After 18 h, water (2 ml) was added. The mixture was stirred for another 2 h. The mixture was sequentially washed with HCl (0.2 N, 2×15 ml), NaOH (0.2 N, 2×15 ml), and water (10 ml), dried (Na$_2$SO$_4$), filtered and concentrated to give N-((3,4-di-methoxyphenyl)methyl)-N-(1-(tert-butyloxycarbonyl)piperidin-4-yl)-4-methoxyphenylacetamide. The crude product was used without any further purification. N-((3,4-Di-methoxyphenyl)methyl)-N-(1-(tert-butyloxycarbonyl)piperidin-4-yl)-4-methoxyphenylacetamide was dissolved in diethyl ether (2 ml) and HCl (1 ml, 4 M in dioxane) was added. The reaction mixture was stirred at room temperature. After 2.5 h, NaOH (1 ml, 6 N) was added followed by dichloromethane (10 ml). The mixture was extracted with water (2×15 ml), dried (Na$_2$SO$_4$), filtered to give a clear solution. The solution was added on to a column carrying strongly acidic cation exchange resin (0.3 mmol/g resin), which was washed with methanol (3×6 ml), and eluted with 10% NH$_3$ in methanol, and concentrated to give the title compound. Yield: 54 mg; $^{13}$C-NMR (CD$_3$OD, rotamers): δ 25.9, 27.3, 40.0, 40.1, 43.5, 43.8, 44.1, 51.4, 53.5, 54.6, 55.4, 110.2, 111.0, 111.9, 112.2, 114.0, 114.2, 118.6, 119.4, 127.1, 127.4, 129.9, 130.0, 130.5, 132.1, 148.2, 148.7, 149.2, 149.7, 158.98, 159.05, 173.3, 173.6.

Example 25

N-((4-Fluorophenyl)methyl)-N-(piperidin-4-yl)-4-methoxyphenylacetamide (26HCH80-7)

To a solution of commercially available tert-butyl 4-oxo-1-piperidine carboxylate (400 mg, 2 mmol) in methanol (1 ml) and 4-fluorobenzylamine (0.114 ml, 1 mmol) in methanol (1 ml) was added acetic acid in methanol (1 M, 1.34 ml) followed by NaCNBH$_3$ in methanol (0.3 M, 4.4 ml). The resulting solution was stirred at room temperature. After 24 h, water (2 ml) was added, and the mixture was stirred for 1 h, before it was concentrated. The resulting oil was redissolved in diethyl ether (20 ml), extracted with HCl (0.1 N, 1×15 ml). The aqueous layer was washed with diethyl ether (10 ml) and treated with 0.2 N NaOH until basic (pH>8), before extracted with dichloromethane (20 ml). The organic layer was dried (Na$_2$SO$_4$), filtered, and concentrated to give tert-butyl 4-((4-fluorophenyl)methyl)amino-piperidine carboxylate. Yield: 130 mg. To a solution of tert-butyl 4-((4-fluorophenyl)methyl)amino-piperidine carboxylate (50 mg, 0.16 mmol) in dichloromethane (6 ml) was added diisopropylethylamine (0.070 ml, 0.4 mmol) followed by 4-methoxyphenylacetyl chloride (0.055 ml, 0.35 mmol). The reaction mixture was stirred at room temperature. After 18 h, water (2 ml) was added. The mixture was stirred for another 2 h. The mixture was sequentially washed with HCl (0.2 N, 2×15 ml), NaOH (0.2 N, 2×15 ml), and water (10 ml), dried (Na$_2$SO$_4$), filtered and concentrated to give N-((4-fluorophenyl)methyl)-N-(1-(tert-butyloxycarbonyl)piperidin-4-yl)-4-methoxyphenylacetamide. The crude product was used without any further purification. N-((4-Fluorophenyl)methyl)-N-(1-(tert-butyloxycarbonyl)piperidin-4-yl)-4-methoxyphenylacetamide was dissolved in diethyl ether (2 ml) and HCl (1 ml, 4 M in dioxane) was added. The reaction mixture was stirred at room temperature. After 2.5 h, NaOH (1 ml, 6 N) was added followed by dichloromethane (10 ml). The mixture was extracted with water (2×15 ml), dried (Na$_2$SO$_4$), filtered to give a clear solution. The solution was added on to a column carrying strongly acidic cation exchange resin (0.3 mmol/g resin), which was washed with methanol (3×6 ml), and eluted with 10% NH$_3$ in methanol, and concentrated to give the title compound. Yield: 45 mg; $^{13}$C-NMR (CD$_3$OD, rotamers): δ 26.1, 27.5, 40.1, 43.6, 43.8, 44.0, 51.6, 53.6, 54.6, 113.77, 113.84, 114.0, 114.1, 114.7, 114.9, 115.3, 115.6, 126.8, 127.2, 128.1, 128.6, 128.7, 129.8, 130.0, 130.1, 130.6, 131.0, 133.8, 159.1, 173.3, 173.6.

Example 26

N-((2,4-Di-chlorophenyl)methyl)-N-(piperidin-4-yl)-4-methoxyphenylacetamide (26HCH80-8)

To a solution of commercially available tert-butyl 4-oxo-1-piperidine carboxylate (400 mg, 2 mmol) in methanol (1 ml) and 2,4-di-chlorobenzylamine (0.135 ml, 1 mmol) in methanol (1 ml) was added acetic acid in methanol (1 M, 1.34 ml) followed by NaCNBH$_3$ in methanol (0.3 M, 4.4 ml). The resulting solution was stirred at room temperature. After 24 h, water (2 ml) was added, and the mixture was stirred for 1 h, before it was concentrated. The resulting oil was redissolved in diethyl ether (20 ml), extracted with HCl (0.1 N, 1×15 ml). The aqueous layer was washed with diethyl ether (10 ml) and treated with 0.2 N NaOH until basic (pH>8), before extracted with dichloromethane (20 ml). The organic layer was dried (Na$_2$SO$_4$), filtered, and concentrated to give tert-butyl 4-((2,4-di-chlorophenyl)methyl)amino-piperidine carboxylate. Yield: 97 mg. To a solution of tert-butyl 4-((2,4-di-chlorophenyl)methyl)amino-piperidine carboxylate (50 mg, 0.14 mmol) in dichloromethane (6 ml) was added diisopropylethylamine (0.070 ml, 0.4 mmol) followed by 4-methoxyphenylacetyl chloride (0.055 ml, 0.35 mmol). The reaction mixture was stirred at room temperature. After 18 h, water (2 ml) was added. The mixture was stirred for another 2 h. The mixture was sequentially washed with HCl (0.2 N, 2×15 ml), NaOH (0.2 N, 2×15 ml), and water (10 ml), dried (Na$_2$SO$_4$), filtered and concentrated to give N-((2,4-di-chlorophenyl)methyl)-N-(1-(tert-butyloxycarbonyl)piperidin-4-yl)-4-methoxyphenylacetamide. The crude product was used without any further purification. N-((2,4-Di-chlorophenyl)methyl)-N-(1-(tert-butyloxycarbonyl)piperidin-4-yl)-4-methoxyphenylacetamide was dissolved in diethyl ether (2 ml) and HCl (1 ml, 4 M in dioxane) was added. The reaction mixture was stirred at room temperature. After 2.5 h, NaOH (1 ml, 6 N) was added followed by dichloromethane (10 ml). The mixture was extracted with water (2×15 ml), dried (Na$_2$SO$_4$), filtered to give a clear solution. The solution was added on to a column carrying strongly acidic cation exchange resin (0.3 mmol/g resin), which was washed with methanol (3×6 ml), and eluted with 10% NH$_3$ in methanol, and concentrated to give the title compound. Yield: 39 mg; $^{13}$C-NMR (CD$_3$OD, rotamers): δ 25.7, 26.8, 40.0, 42.6, 43.3, 43.7, 51.2, 53.0, 54.5, 54.6, 113.8, 113.8, 114.0, 114.1, 127.0, 128.4, 128.8, 129.8, 130.0, 130.1, 131.0, 132.7, 132.9, 134.5, 159.1, 173.4, 173.6.

Example 27

N-((3-Methylphenyl)methyl)-N-(piperidin-4-yl)-4-methoxyphenylacetamide (26HCH80-9)

To a solution of commercially available tert-butyl 4-oxo-1-piperidine carboxylate (400 mg, 2 mmol) in methanol (1 ml) and 3-methylbenzylamine (0.125 ml, 1 mmol) in methanol (1 ml) was added acetic acid in methanol (1 M, 1.34 ml) followed by NaCNBH$_3$ in methanol (0.3 M, 4.4 ml). The resulting solution was stirred at room temperature. After 24 h, water (2 ml) was added, and the mixture was stirred for 1 h, before it was concentrated. The resulting oil was redissolved in diethyl ether (20 ml), extracted with HCl (0.1 N, 1×15 ml). The aqueous layer was washed with diethyl ether (10 ml) and treated with 0.2 N NaOH until basic (pH>8), before extracted with dichloromethane (20 ml). The organic layer was dried (Na$_2$SO$_4$), filtered, and concentrated to give tert-butyl 4-((3-methylphenyl)methyl)amino-piperidine carboxylate. Yield: 136 mg. To a solution of tert-butyl 4-((3-methylphenyl)methyl)amino-piperidine carboxylate (50 mg, 0.16 mmol) in dichloromethane (6 ml) was added diisopropylethylamine (0.070 ml, 0.4 mmol) followed by 4-methoxyphenylacetyl chloride (0.055 ml, 0.35 mmol). The reaction mixture was stirred at room temperature. After 18 h, water (2 ml) was added. The mixture was stirred for another 2 h. The mixture was sequentially washed with HCl (0.2 N, 2×15 ml), NaOH (0.2 N, 2×15 ml), and water (10 ml), dried (Na$_2$SO$_4$), filtered and concentrated to give N-((3-methylphenyl)methyl)-N-(1-(tert-butyloxycarbonyl)piperidin-4-yl)-4-methoxyphenylacetamide. The crude product was used without any further purification. N-((3-Methylphenyl)methyl)-N-(1-(tert-butyloxycarbonyl)piperidin-4-yl)-4-methoxyphenylacetamide was dissolved in diethyl ether (2 ml) and HCl (1 ml, 4 M in dioxane) was added. The reaction mixture was stirred at room temperature. After 2.5 h, NaOH (1 ml, 6 N) was added followed by dichloromethane (10 ml). The mixture was extracted with water (2×15 ml), dried (Na$_2$SO$_4$), filtered to give a clear solution. The solution was added on to a column carrying strongly acidic cation exchange resin (0.3 mmol/g resin), which was washed with methanol (3×6 ml), and eluted with 10% NH$_3$ in methanol, and concentrated to give the title compound. Yield: 48 mg; $^{13}$C-NMR (CD$_3$OD, rotamers): δ 20.4, 26.8, 28.3, 40.2, 43.9, 44.1, 44.5, 51.8, 54.2, 54.57, 54.61, 114.0, 114.1, 123.2, 123.7, 126.7, 127.0, 127.1, 127.3, 128.0, 128.1, 128.7, 129.8, 129.9, 137.9, 138.6, 138.9, 159.0, 159.1, 173.1, 173.7.

Example 28

N-((3-Bromophenyl)methyl)-N-(piperidin-4-yl)-4-methoxyphenylacetamide (26HCH80-10)

To a solution of commercially available tert-butyl 4-oxo-1-piperidine carboxylate (400 mg, 2 mmol) in methanol (1 ml) and 3-bromobenzylamine hydrobromide (222 mg, 1 mmol) in methanol (1 ml) was added acetic acid in methanol (1 M, 1.34 ml) followed by NaCNBH$_3$ in methanol (0.3 M, 4.4 ml). The resulting solution was stirred at room temperature. After 24 h, water (2 ml) was added, and the mixture was stirred for 1 h, before it was concentrated. The resulting oil was redissolved in diethyl ether (20 ml), extracted with HCl (0.1 N, 1×15 ml). The aqueous layer was washed with diethyl ether (10 ml) and treated with 0.2 N NaOH until basic (pH>8), before extracted with dichloromethane (20 ml). The organic layer was dried (Na$_2$SO$_4$), filtered, and concentrated to give tert-butyl 4-((3-bromophenyl)methyl)amino-piperidine carboxylate. Yield: 142 mg. To a solution of tert-butyl 4-((3-bromophenyl)methyl)amino-piperidine carboxylate (50 mg, 0.14 mmol) in dichloromethane (6 ml) was added diisopropylethylamine (0.070 ml, 0.4 mmol) followed by 4-methoxyphenylacetyl chloride (0.055 ml, 0.35 mmol). The reaction mixture was stirred at room temperature. After 18 h, water (2 ml) was added. The mixture was stirred for another 2 h. The mixture was sequentially washed with HCl (0.2 N, 2×15 ml), NaOH (0.2 N, 2×15 ml), and water (10 ml), dried (Na$_2$SO$_4$), filtered and concentrated to give N-((3-bromophenyl)methyl)-N-(1-(tert-butyloxycarbonyl)piperidin-4-yl)-4-methoxyphenylacetamide. The crude product was used without any further purification. N-((3-Bromophenyl)methyl)-N-(1-(tert-butyloxycarbonyl)piperidin-4-yl)-4-methoxyphenylacetamide was dissolved in diethyl ether (2 ml) and HCl (1 ml, 4 M in dioxane) was added. The reaction mixture was stirred at room temperature. After 2.5 h, NaOH (1 ml, 6 N) was added followed by dichloromethane (10 ml). The mixture was extracted with water (2×15 ml), dried (Na$_2$SO$_4$), filtered to give a clear solution. The solution was added on to a column carrying strongly acidic cation exchange resin (0.3 mmol/g resin), which was washed with methanol (3×6 ml), and eluted with 10% NH$_3$ in methanol, and concentrated to give the title compound. Yield: 49 mg; $^{13}$C-NMR (CD$_3$OD, rotamers): δ 26.6, 28.2, 40.2, 43.9, 44.0, 51.8, 54.1, 54.6, 113.76, 113.84, 114.1, 114.2, 122.2, 125.0, 125.5, 126.7, 127.1, 129.2, 129.5, 129.7, 129.8, 129.9, 130.0, 130.5, 130.6, 140.8, 141.8, 159.1, 173.3, 173.7.

Example 29

N-(1-(Phenylmethyl)piperidin-4-yl)-N-(3-phenyl-2-propen-1-yl)-4-methoxyphenylacetamide (26HCH76B)

To a solution of 4-amino-N-benzylpiperidine (200 mg, 1.05 mmol) in methanol (2 ml) was added trans-cinnamaldehyde (211 mg, 1.6 mmol), followed by Acetic acid in methanol (1 M, 1.4 ml) and sodiumcyanoborohydride in methanol (0.3 M, 4.4 ml). The reaction mixture was stirred at room temperature. After 48 h, water (2 ml) was added. The mixture was stirred for another 2 h before concentrated and redissolved in diethyl ether (20 ml). The organic layer was extracted with HCl (0.1 N, 2×10 ml). The combined aqueous layers were treated with NaOH (0.2 N) until basic (pH>8). The mixture was extracted with dichloromethane (2×10 ml). The combined organic layers were dried (Na$_2$SO$_4$) and concentrated. The crude product, which was used without any further purification, was dissolved in dichloromethane (5 ml). Diisopropylethylamine (284 mg, 2.1 eq.) was added, followed by 4-methoxyphenylacetyl chloride (387 mg, 2.0 eq). The reaction mixture was stirred at room temperature. After 18 h, water (2 ml) was added. After additional 2 h dichloromethane (10 ml) was added.

The mixture was extracted with NaOH (0.2 N, 3×15 ml), and water (15 ml). The organic layer was dried (Na$_2$SO$_4$) and concentrated. The crude product was redissolved in methanol (2 ml) and added on to a column carrying strongly acidic cation exchange resin (0.3 mmol/g resin), which was washed with methanol (3×6 ml), and eluted with 10% NH$_3$ in methanol, and concentrated to give the title compound. $^{13}$C-NMR (CDCl$_3$): δ 28.5, 38.1, 46.6, 47.4, 50.9, 54.7, 62.9, 113.7, 125.5, 126.4, 126.6, 127.4, 127.9, 128.5, 128.6, 129.6, 130.0, 135.2, 135.3, 138.0, 158.2, 173.2.

Example 30

N-((4-Methylphenyl)methyl)-N-(1-piperidin-4-yl)-phenylacetamide (26HCH78-1)

To a solution of commercially available tert-butyl 4-oxo-1-piperidine carboxylate (1.75 g, 8.8 mmol) and 4-methylbenzylamine (970 mg, 8.0 mmol) in methanol (7 ml) was added acetic acid in methanol (1 M, 6.7 ml) followed by NaCNBH$_3$ in methanol (0.3 M, 30 ml). The resulting solution was stirred at room temperature. After 20 h, water (5 ml) was added, and the mixture was stirred for 1 h, before it was concentrated. Flash chromatography in dichloromethane:methanol 10:1 gave tert-butyl 4-(4-methylphenyl)methyl)amino-piperidine carboxylate. Yield: 2.4 g, 98%. To a solution of tert-butyl 4-(4-methylphenyl)methyl)amino-piperidine carboxylate (80 mg, 0.26 mmol) in dichloromethane (1.8 ml) was added diisopropylethylamine (0.11 ml, 2.4 eq.) followed by phenylacetyl chloride (81 mg, 0.53 mmol). The reaction mixture was stirred at room temperature. After 20 h, water (1 ml) was added. The mixture was stirred for another 2 h, before diethyl ether (20 ml) was added. The mixture was sequentially extracted with HCl (0.2 N, 2×15 ml), NaOH (0.2 N, 2×15 ml), and H$_2$O (10 ml), dried (Na$_2$SO$_4$), filtered and concentrated. The crude material was dissolved in diethyl ether (2 ml) and HCl (4 M in dioxane, 1 ml). The reaction mixture was stirred at room temperature. After 2 h, NaOH (6 N, 1 ml) was added followed by dichloromethane (10 ml). The mixture was extracted with water (2×10 ml), dried (Na$_2$SO$_4$), and filtered to give a clear solution. The solution was added on to a column carrying strongly acidic cation exchange resin (0.3 mmol/g resin), which was washed with methanol (3×6 ml), and eluted with 10% NH$_3$ in methanol, and concentrated to give the title compound. Yield: 38 mg; $^{13}$C-NMR (CD$_3$OD, rotamers): δ 19.9, 26.9, 28.4, 41.0, 41.1, 44.0, 44.1, 44.4, 51.9, 54.4, 126.1, 126.7, 126.8, 126.9, 128.5, 128.7, 128.78, 128.81, 128.9, 129.4, 129.5, 134.9, 135.2, 135.6, 136.0, 136.3, 137.2, 172.8, 173.3.

Example 31

N-((4-Methylphenyl)methyl)-N-(1-piperidin-4-yl)-3-phenylpropionamide (26HCH78-2)

To a solution of commercially available tert-butyl 4-oxo-1-piperidine carboxylate (1.75 g,. 8.8 mmol) and 4-methylbenzylamine (970 mg, 8.0 mmol) in methanol (7 ml) was added acetic acid in methanol (1 M, 6.7 ml) followed by NaCNBH$_3$ in methanol (0.3 M, 30 ml). The resulting solution was stirred at room temperature. After 20 h, water (5 ml) was added, and the mixture was stirred for 1 h, before it was concentrated. Flash chromatography in dichloromethane:methanol 10:1 gave tert-butyl 4-(4-methylphenyl)methyl)amino-piperidine carboxylate. Yield: 2.4 g, 98%. To a solution of tert-butyl 4-(4-methylphenyl)methyl)amino-piperidine carboxylate (80 mg, 0.26 mmol) in dichloromethane (1.8 ml) was added diisopropylethylamine (0.11 ml, 2.4 eq.) followed by 3-phenylpropionyl chloride (0.078 ml, 0.53 mmol). The reaction mixture was stirred at room temperature. After 20 h, water (1 ml) was added. The mixture was stirred for another 2 h, before diethyl ether (20 ml) was added. The mixture was sequentially extracted with HCl (0.2 N. 2×15 ml), NaOH (0.2 N, 2×15 ml), and H$_2$O (10 ml), dried (Na$_2$SO$_4$), filtered and concentrated. The crude material was dissolved in diethyl ether (2 ml) and HCl (4 M in dioxane, 1 ml). The reaction mixture was stirred at room temperature. After 2 h, NaOH (6 N, 1 ml) was added followed by dichloromethane (10 ml). The mixture was extracted with water (2×10 ml), dried (Na$_2$SO$_4$), and filtered to give a clear solution. The solution was added on to a column carrying strongly acidic cation exchange resin (0.3 mmol/g resin), which was washed with methanol (3×6 ml), and eluted with 10% NH$_3$ in methanol, and concentrated to give the title compound. Yield: 43 mg; $^{13}$C-NMR (CD$_3$OD, rotamers): δ 19.9, 27.4, 29.0, 31.4, 31.7, 34.7, 35.7, 44.2, 44.3, 51.6, 54.2, 125.9, 126.07, 126.15, 126.8, 128.3, 128.4, 128.7, 128.8, 129.3, 135.1, 136.1, 136.2, 137.0, 141.1, 141.2, 173.9, 174.4.

Example 32

N-((4-Methylphenyl)methyl)-N-(1-piperidin-4-yl)-(phenylthio)acetamide (26HCH78-3)

To a solution of commercially available tert-butyl 4-oxo-1-piperidine carboxylate (1.75 g, 8.8 mmol) and 4-methylbenzylamine (970 mg, 8.0 mmol) in methanol (7 ml) was added acetic acid in methanol (1 M, 6.7 ml) followed by NaCNBH$_3$ in methanol (0.3 M, 30 ml). The resulting solution was stirred at room temperature. After 20 h, water (5 ml) was added, and the mixture was stirred for 1 h, before it was concentrated. Flash chromatography in dichloromethane:methanol 10:1 gave tert-butyl 4-(4-methylphenyl)methyl)amino-piperidine carboxylate. Yield: 2.4 g, 98%. To a solution of tert-butyl 4-(4-methylphenyl)methyl)amino-piperidine carboxylate (80 mg, 0.26 mmol) in dichloromethane (1.8 ml) was added diisopropylethylamine (0.11 ml, 2.4 eq.) followed by (phenylthio)acetyl chloride (0.078 ml, 0.53 mmol). The reaction mixture was stirred at room temperature. After 20 h, water (1 ml) was added. The mixture was stirred for another 2 h, before diethyl ether (20 ml) was added. The mixture was sequentially extracted with HCl (0.2 N, 2×15 ml), NaOH (0.2 N, 2×15 ml), and H$_2$O (10 ml), dried (Na$_2$SO$_4$), filtered and concentrated. The crude material was dissolved in diethyl ether (2 ml) and HCl (4 M in dioxane, 1 ml). The reaction mixture was stirred at room temperature. After 2 h, NaOH (6 N, 1 ml) was added followed by dichloromethane (10 ml). The mixture was extracted with water (2×10 ml), dried (Na$_2$SO$_4$), and filtered to give a clear solution. The solution was added on to a column carrying strongly acidic cation exchange resin (0.3 mmol/g resin), which was washed with methanol (3×6 ml), and eluted with 10% NH$_3$ in methanol, and concentrated to give the title compound. Yield: 18 mg; HRMS (FAB[30], NBA) (M+H)$^+$ 355.1841, C$_{21}$H$_{27}$N$_2$OS requires 355.1844; LC-MS: (M+H)$^+$ 355.1, t$_r$ 2.62 min.

Example 33

N-((4-Methylphenyl)methyl)-N-(1-piperidin-4-yl)-phenoxyacetamide (26HCH78-4)

To a solution of commercially available tert-butyl 4-oxo-1-piperidine carboxylate (1.75 g, 8.8 mmol) and 4-methylbenzylamine (970 mg, 8.0 mmol) in methanol (7 ml) was added acetic acid in methanol (1 M, 6.7 ml)

followed by NaCNBH$_3$ in methanol (0.3 M, 30 ml). The resulting solution was stirred at room temperature. After 20 h, water (5 ml) was added, and the mixture was stirred for 1 h, before it was concentrated. Flash chromatography in dichloromethane:methanol 10:1 gave tert-butyl 4-(4-methylphenyl)methyl)amino-piperidine carboxylate. Yield: 2.4 g, 98%. To a solution of tert-butyl 4-(4-methylphenyl) methyl)amino-piperidine carboxylate (80 mg, 0.26 mmol) in dichloromethane (1.8 ml) was added diisopropylethylamine (0.11 ml, 2.4 eq.) followed by phenoxyacetyl chloride (0.073 ml, 0.53 mmol). The reaction mixture was stirred at room temperature. After 20 h, water (1 ml) was added. The mixture was stirred for another 2 h, before diethyl ether (20 ml) was added. The mixture was sequentially extracted with HCl (0.2 N, 2×15 ml), NaOH (0.2 N, 2×15 ml), and H$_2$O (10 ml), dried (Na$_2$SO$_4$), filtered and concentrated. The crude material was dissolved in diethyl ether (2 ml) and HCl (4 M in dioxane, 1 ml). The reaction mixture was stirred at room temperature. After 2 h, NaOH (6 N, 1 ml) was added followed by dichloromethane (10 ml). The mixture was extracted with water (2×10 ml), dried (Na$_2$SO$_4$), and filtered to give a clear solution. The solution was added on to a column carrying strongly acidic cation exchange resin (0.3 mmol/g resin), which was washed with methanol (3×6 ml), and eluted with 10% NH$_3$ in methanol, and concentrated to give the title compound. Yield: 24 mg; $^{13}$C-NMR (CD$_3$OD, rotamers): δ 19.9, 25.8, 27.4, 43.5, 43.7, 44.4, 51.9, 52.3, 66.9, 114.7, 114.8, 116.7, 117.0, 121.4, 123.6, 126.3, 126.8, 128.4, 128.9, 129.3, 129.5, 129.6, 131.0, 134.4, 136.1, 137.4, 158.3, 169.8, 170.1.

Example 34

N-((4-Methylphenyl)methyl)-N-(1-piperidin-4-yl)-(4-chlorophenoxy)acetamide (26HCH78-5)

To a solution of commercially available tert-butyl 4-oxo-1-piperidine carboxylate (1.75 g, 8.8 mmol) and 4-methylbenzylamine (970 mg, 8.0 mmol) in methanol (7 ml) was added acetic acid in methanol (1 M, 6.7 ml) followed by NaCNBH$_3$ in methanol (0.3 M, 30 ml). The resulting solution was stirred at room temperature. After 20 h, water (5 ml) was added, and the mixture was stirred for 1 h, before it was concentrated. Flash chromatography in dichloromethane:methanol 10:1 gave tert-butyl 4-(4-methylphenyl)methyl)amino-piperidine carboxylate. Yield: 2.4 g, 98%. To a solution of tert-butyl 4-(4-methylphenyl) methyl)amino-piperidine carboxylate (80 mg, 0.26 mmol) in dichloromethane (1.8 ml) was added diisopropylethylamine (0.11 ml, 2.4 eq.) followed by 4-chlorophenoxyacetyl chloride (0.082 ml, 0.53 mmol). The reaction mixture was stirred at room temperature. After 20 h, water (1 ml) was added. The mixture was stirred for another 2 h, before diethyl ether (20 ml) was added. The mixture was sequentially extracted with HCl (0.2 N, 2×15 ml), NaOH (0.2 N, 2×15 ml), and H$_2$O (10 ml), dried (Na$_2$SO$_4$), filtered and concentrated. The crude material was dissolved in diethyl ether (2 ml) and HCl (4 M in dioxane, 1 ml). The reaction mixture was stirred at room temperature. After 2 h, NaOH (6 N, 1 ml) was added followed by dichloromethane (10 ml). The mixture was extracted with water (2×10 ml), dried (Na$_2$SO$_4$), and filtered to give a clear solution. The solution was added on to a column carrying strongly acidic cation exchange resin (0.3 mmol/g resin), which was washed with methanol (3×6 ml), and eluted with 10% NH$_3$ in methanol, and concentrated to give the title compound. Yield: 21 mg; $^{13}$C-NMR (CD$_3$OD, rotamers): δ 19.9, 26.2, 27.8, 43.6, 43.9, 44.4, 52.2, 52.5, 67.0, 116.2, 116.4, 126.2, 126.3, 126.8, 128.6, 128.9, 129.1, 129.3, 129.5, 131.0, 134.4, 135.6, 136.4, 137.5, 157.1, 169.4, 169.7.

Example 35

N-((4-Methylphenyl)methyl)-N-(1-piperidin-4-yl)-3-methoxyphenylacetamide (26HCH78-6)

To a solution of commercially available tert-butyl 4-oxo-1-piperidine carboxylate (1.75 g, 8.8 mmol) and 4-methylbenzylamine (970 mg, 8.0 mmol) in methanol (7 ml) was added acetic acid in methanol (1 M, 6.7 ml) followed by NaCNBH$_3$ in methanol (0.3 M, 30 ml). The resulting solution was stirred at room temperature. After 20 h, water (5 ml) was added, and the mixture was stirred for 1 h, before it was concentrated. Flash chromatography in dichloromethane:methanol 10:1 gave tert-butyl 4-(4-methylphenyl)methyl)amino-piperidine carboxylate. Yield: 2.4 g, 98%. To a solution of tert-butyl 4-(4-methylphenyl) methyl)amino-piperidine carboxylate (80 mg, 0.26 mmol) in dichloromethane (1.8 ml) was added diisopropylethylamine (0.11 ml, 2.4 eq.) followed by 3-methoxyphenylacetyl chloride (97 mg, 0.53 mmol). The reaction mixture was stirred at room temperature. After 20 h, water (1 ml) was added. The mixture was stirred for another 2 h, before diethyl ether (20 ml) was added. The mixture was sequentially extracted with HCl (0.2 N, 2×15 ml), NaOH (0.2 N, 2×15 ml), and H$_2$O (10 ml), dried (Na$_2$SO$_4$), filtered and concentrated. The crude material was dissolved in diethyl ether (2 ml) and HCl (4 M in dioxane, 1 ml). The reaction mixture was stirred at room temperature. After 2 h, NaOH (6 N, 1 ml) was added followed by dichloromethane (10 ml). The mixture was extracted with water (2×10 ml), dried (Na$_2$SO$_4$), and filtered to give a clear solution. The solution was added on to a column carrying strongly acidic cation exchange resin (0.3 mmol/g resin), which was washed with methanol (3×6 ml), and eluted with 10% NH$_3$ in methanol, and concentrated to give the title compound. Yield: 26 mg; $^{13}$C-NMR (CD$_3$OD, rotamers): δ 19.9, 26.3, 27.7, 41.0, 43.7, 43.9, 44.4, 51.5, 53.8, 54.5, 54.6, 112.2, 112.6, 114.3, 114.5, 121.0, 121.2, 126.1, 126.8, 128.8, 129.4, 129.5, 129.8, 134.8, 136.0, 136.3, 136.5, 136.9, 137.2, 160.2, 160.3, 172.8, 173.2.

Example 36

N-((4-Methylphenyl)methyl)-N-(1-piperidin-4-yl)-4-fluorophenylacetamide (26HCH78-7)

To a solution of commercially available tert-butyl 4-oxo-1-piperidine carboxylate (1.75 g, 8.8 mmol) and 4-methylbenzylamine (970 mg, 8.0 mmol) in methanol (7 ml) was added acetic acid in methanol (1 M, 6.7 ml) followed by NaCNBH$_3$ in methanol (0.3 M, 30 ml). The resulting solution was stirred at room temperature. After 20 h, water (5 ml) was added, and the mixture was stirred for 1 h, before it was concentrated. Flash chromatography in dichloromethane:methanol 10:1 gave tert-butyl 4-(4-methylphenyl)methyl)amino-piperidine carboxylate. Yield: 2.4 g, 98%. To a solution of tert-butyl 4-(4-methylphenyl) methyl)amino-piperidine carboxylate (80 mg, 0.26 mmol) in dichloromethane (1.8 ml) was added diisopropylethylamine (0.11 ml, 2.4 eq.) followed by 4-fluorophenylacetyl chloride (0.072 ml, 0.53 mmol). The reaction mixture was stirred at room temperature. After 20 h, water (1 ml) was added. The mixture was stirred for another 2 h, before diethyl ether (20 ml) was added. The mixture was sequentially extracted with HCl (0.2 N, 2×15 ml), NaOH (0.2 N, 2×15 ml), and H$_2$O (10 ml), dried (Na$_2$SO$_4$), filtered and concentrated. The crude material was dissolved in diethyl ether (2 ml) and HCl (4 M in dioxane, 1 ml). The reaction mixture was stirred at room temperature. After 2 h, NaOH (6 N, 1 ml) was added followed by dichloromethane (10 ml). The mixture was extracted with water (2×10 ml), dried (Na$_2$SO$_4$), and filtered to give a clear solution. The solution was added on to a column carrying strongly acidic cation exchange resin (0.3 mmol/g resin), which was washed with methanol (3×6 ml), and eluted with 10% NH$_3$ in methanol, and concentrated to give the title compound. Yield: 26 mg; $^{13}$C-NMR (CD$_3$OD, rotamers): δ 19.9, 26.1, 27.4, 39.7, 39.9, 43.5, 43.8, 44.4, 51.3, 53.4, 114.9, 115.1, 115.3, 126.1, 126.7, 128.5, 128.8, 129.4, 130.7, 130.8, 130.9, 131.0, 131.2, 131.6, 134.8, 136.0, 136.3, 137.2, 160.9, 163.3, 172.7, 173.2.

Example 37

N-((4-Methylphenyl)methyl)-N-(1-piperidin-4-yl)-2, 5-di-methoxyphenylacetamide (26HCH78-8)

To a solution of commercially available tert-butyl 4-oxo-1-piperidine carboxylate (1.75 g, 8.8 mmol) and 4-methylbenzylamine (970 mg, 8.0 mmol) in methanol (7 ml) was added acetic acid in methanol (1 M, 6.7 ml) followed by NaCNBH$_3$ in methanol (0.3 M, 30 ml). The resulting solution was stirred at room temperature. After 20 h, water (5 ml) was added, and the mixture was stirred for 1 h, before it was concentrated. Flash chromatography in dichloromethane:methanol 10:1 gave tert-butyl 4-(4-methylphenyl)methyl)amino-piperidine carboxylate. Yield: 2.4 g, 98%. To a solution of tert-butyl 4-(4-methylphenyl) methyl)amino-piperidine carboxylate (80 mg, 0.26 mmol) in dichloromethane (1.8 ml) was added diisopropylethylamine (0.11 ml, 2.4 eq.) followed by 2,5-di-methoxyphenylacetyl chloride (0.092 ml, 0.53 mmol). The reaction mixture was stirred at room temperature. After 20 h, water (1 ml) was added. The mixture was stirred for another 2 h, before diethyl ether (20 ml) was added. The mixture was sequentially extracted with HCl (0.2 N, 2×15 ml), NaOH (0.2 N, 2×15 ml), and H$_2$O (10 ml), dried (Na$_2$SO$_4$), filtered and concentrated. The crude material was dissolved in diethyl ether (2 ml) and HCl (4 M in dioxane, 1 ml). The reaction mixture was stirred at room temperature. After 2 h, NaOH (6 N, 1 ml) was added followed by dichloromethane (10 ml). The mixture was extracted with water (2×10 ml), dried (Na$_2$SO$_4$), and filtered to give a clear solution. The solution was added on to a column carrying strongly acidic cation exchange resin (0.3 mmol/g resin), which was washed with methanol (3×6 ml), and eluted with 10% NH$_3$ in methanol, and concentrated to give the title compound. 36 mg; $^{13}$C-NMR (CD$_3$OD, rotamers): δ 20.0, 26.5, 28.2, 35.1, 35.7, 44.0, 44.4, 51.6, 53.8, 54.99, 55.03, 55.2, 55.5, 111.4, 111.7, 112.4, 112.9, 116.6, 116.9, 124.98, 125.02, 126.1, 126.7, 128.8, 129.3, 135.0, 136.1, 136.3, 137.0, 151.3, 151.7, 153.9, 154.0, 173.1, 173.5.

Example 38

N-((4-Methylphenyl)methyl)-N-(1-piperidin-4-yl)-4-chlorophenylacetamide (26HCH78-9)

To a solution of commercially available tert-butyl 4-oxo-1-piperidine carboxylate (1.75 g, 8.8 mmol) and 4-methylbenzylamine (970 mg, 8.0 mmol) in methanol (7 ml) was added acetic acid in methanol (1 M, 6.7 ml) followed by NaCNBH$_3$ in methanol (0.3 M, 30 ml). The resulting solution was stirred at room temperature. After 20 h, water (5 ml) was added, and the mixture was stirred for 1 h, before it was concentrated. Flash chromatography in dichloromethane:methanol 10: 1 gave tert-butyl 4-(4-methylphenyl)methyl)amino-piperidine carboxylate. Yield: 2.4 g, 98%. To a solution of tert-butyl 4-(4-methylphenyl) methyl)amino-piperidine carboxylate (80 mg, 0.26 mmol) in dichloromethane (1.8 ml) was added diisopropylethylamine (0.11 ml, 2.4 eq.) followed by 4-chlorophenylacetyl chloride (99 mg, 0.53 mmol). The reaction mixture was stirred at room temperature. After 20 h, water (1 ml) was added. The mixture was stirred for another 2 h, before diethyl ether (20 ml) was added. The mixture was sequentially extracted with HCl (0.2 N, 2×15 ml), NaOH (0.2 N, 2×15 ml), and H$_2$O (10 ml), dried (Na$_2$SO$_4$), filtered and concentrated. The crude material was dissolved in diethyl ether (2 ml) and HCl (4 M in dioxane, 1 ml). The reaction mixture was stirred at room temperature. After 2 h, NaOH (6 N, 1 ml) was added followed by dichloromethane (10 ml). The mixture was extracted with water (2×10 ml), dried (Na$_2$SO$_4$), and filtered to give a clear solution. The solution was added on to a column carrying strongly acidic cation exchange resin (0.3 mmol/g resin), which was washed with methanol (3×6 ml), and eluted with 10% NH$_3$ in methanol, and concentrated to give the title compound. Yield: 22 mg; $^{13}$C-NMR (CD$_3$OD, rotamers): δ 19.9, 26.3, 27.7, 39.9, 40.0, 43.6, 43.9, 44.4, 51.5, 53.6, 126.1, 126.7, 128.2, 128.4, 128.6, 128.9, 129.4, 129.6, 130.7, 130.9, 131.2, 131.6, 132.5, 132.7, 133.9, 134.1, 134.4, 134.8, 135.9, 136.3, 137.2, 172.4, 172.9.

Example 39

N-((4-Methylphenyl)methyl)-N-(1-(phenylmethyl) pyrrolidin-3-yl)-N'-phenylmethylcarbamide (26HCH50)

To a solution of 3-amino-1-phenylmethylpyrrolidine (353 mg, 2 mmol) and 4-methylbenzaldehyde (361 mg, 3 mmol) in methanol (20 ml) was added acetic acid in methanol (2 M, 6.7 ml) followed by NaCNBH$_3$ in methanol (0.3 M, 3 ml). The mixture was stirred at room temperature. After 24 h, water (5 ml) was added. The mixture was stirred for another hour before concentrated. Flash chromatography in dichloromethane/methanol 10/1 gave N-((4-methylphenyl) methyl)amino-1-phenylmethylpyrrolidine.

N-((4-Methylphenyl)methyl)amino-1-phenylmethylpyrrolidine (35 mg, 0.125 mmol) was dissolved in dichloromethane (1.5 ml), and benzylisocyanate (0.09 ml, 0.3 mmol) was added. The reaction mixture was stirred at room temperature. After 48 h, the crude reaction mixture was added on to a column carrying strongly acidic cation exchange resin, which was washed with methanol (3×6 ml), and eluted with 10% NH$_3$ in methanol, and concentrated to give the title compound. Yield: 48 mg, 92%; $^{13}$C-NMR (CD$_3$OD): δ 20.0, 29.7, 44.2, 51.3, 53.4, 56.4, 57.8, 58.7, 126.8, 127.1, 127.3, 127.6, 128.3, 128.4, 128.9, 129.1, 135.9, 136.8, 140.3, 158.5.

Example 40

N-((4-Methylphenyl)methyl)-N-(1-(phenylmethyl) pyrrolidin-3-yl)-4-methoxyphenylacetamide (26HCH52)

To a solution of 3-amino-1-phenylmethylpyrrolidine (353 mg, 2 mmol) and 4-methylbenzaldehyde (361 mg, 3 mmol) in methanol (20 ml) was added acetic acid in methanol (2 M, 6.7 ml) followed by NaCNBH$_3$ in methanol (0.3 M, 3 ml). The mixture was stirred at room temperature. After 24 h, water (5 ml) was added. The mixture was stirred for another hour before concentrated. Flash chromatography in dichloromethane/methanol 10/1 gave N-((4-methylphenyl) methyl)amino-1-phenylmethylpyrrolidine.

To a solution of N-((4-Methylphenyl)methyl)amino-1-phenylmethylpyrrolidine (35 mg, 0.125 mmol), diisopropylethylamine (0.14 ml) in dichloromethane (1.5 ml) was added 4-methoxyphenylacetyl chloride (0.1 ml, 0.5 mmol). The reaction mixture was stirred at room temperature. After 48 h, the crude reaction mixture was concentrated and redissolved in methanol. The solution was added on to a column carrying strongly acidic cation exchange resin, which was washed with methanol (3×6 ml), and eluted with 10% $NH_3$ in methanol, and concentrated. Flash chromatography in dichloromethane/methanol 10/1 gave the title compound. Yield: 20 mg, 38%; $^{13}$C-NMR ($CD_3OD$): δ 21.3, 30.2, 40.8, 47.8, 53.6, 53.9, 55.5, 57.5, 60.2, 114.4, 125.7, 127.0, 127.1, 127.3, 127.4, 128.4, 128.5, 128.7, 128.9, 129.2, 129.8, 130.0, 135.9, 137.0, 158.6.

Example 41

N-((4-Methylphenyl)methyl)-N-(1-(phenylmethyl) piperidin-4-yl)-4-methoxyphenylthioacetamide (RO)

A mixture of N-((4-Methylphenyl)methyl)-N-(1-(phenylmethyl)piperidin-4-yl)-(4-methoxyphenylmethyl) acetamide (20 mg, 0.045 mmol) and Lawesson's reagent (25 mg, 0.062 mmol), was taken in a glass vial and mixed thoroughly with magnetic stirbars. The glass vial was then irradiated in a microwave oven (900 W, Whirlpool M401)for 8 min. Upon completion of the reaction, the yellow-colored material was transferred to an ion-exchange column with the aid of methanol (2 ml). The ion-exchange column was subsequently washed with $CH_2Cl_2$ (2ml) and methanol (2 ml) and the product was thereafter eluted from the ion-exchange column (10% $NH_3$ in methanol, 2 ml)to give N-((4-Methylphenyl)methyl)-N-(1-(phenylmethyl) piperidin-4-yl)-4-methoxyphenylmethyl thioacetamide (20 mg, 97%) as a white solid; LC-MS: $(N+H)^+$ 459, $t_r$ 9.60 min; TLC ($CH_2Cl_2$/methanol 20: 1)$R_f$=0.38.

Example 42

Receptor Selection and Amplification (R-SAT) Assays.

The functional receptor assay, Receptor Selection and Amplification Technology (R-SAT), was used (with minor modifications from that previously described U.S. Pat. No. 5,707,798)to screen compounds for efficacy at the 5-HT2A receptor. Briefly, NIH3T3 cells were grown in 96 well tissue culture plates to 70–80% confluence. Cells were transfected for 12–16 hours with plasmid DNAs using superfect (Qiagen Inc.) as per manufacture's protocols. R-SAT's were generally performed with 50 ng/well of receptor and 20 ng/well of Beta-galactosidase plasmid DNA. All receptor and G-protein constructs used were in the pSI mammalian expression vector (Promega Inc) as described in U.S. Pat. No. 5,707,798. The 5HT2A receptor gene was amplified by nested PCR from brain cDNA using the oligodeoxynucleotides based on the published sequence (see Saltzman et. al. Biochem. Biophys. Res. Comm. 181:1469–78 (1991)). Large-scale transfections, cells were transfected for 12–16 hours, then trypsinized and frozen in DMSO. Frozen cells were later thawed, plated at 10,000–40,000 cells per well of a 96 well plate that contained drug. With both methods, cells were then grown in a humidified atmosphere with 5% ambient CO2 for five days. Media was then removed from the plates and marker gene activity was measured by the addition of the beta-galactosidase substrate ONPG (in PBS with 5% NP-40). The resulting colorimetric reaction was measured in a spectrophotometric plate reader (Titertek Inc.)at 420 nM. All data were analyzed using the computer program XLFit (IDBSm). Efficacy is the percent maximal repression compared to repression by a control compound (ritanserin in the case of 5HT2A). pIC50 is the negative of the log(IC50), where IC50 is the calculated concentration in Molar that produces 50% maximal repression. The results obtained for six compounds of the invention are presented in the following table.

TABLE 1

Efficacy of Compounds at the 5-HT2A Receptor

| Compound | Efficacy (average) | Efficacy (stdev) | pIC50 (average) | pIC50 (stdev) |
|---|---|---|---|---|
| 26HCH52 | 98 | 5.0 | 7.31 | 0.16 |
| 26HCH66-03 | 76 | 13.3 | 7.42 | 0.01 |
| 26HCH66-05 | 109 | 3.0 | 7.55 | 0.15 |
| 26HCH80-2 | 89 | 4.6 | 7.78 | 0.17 |
| 26HCH80-7 | 87 | 3.7 | 7.70 | 0.26 |
| 26HCH80-10 | 91 | 4.9 | 7.21 | 0.05 |

Example 43

In Vitro Efficacy of 26HCH17 as an Inverse Agonist at the 5-HT2A Receptor.

The graph shown in FIG. 1 represents the data obtained from a dose response analysis of 26HCH17 and ritanserin as 5-HT2A receptor inverse agonists. Briefly, the 5-HT2A receptor, and the alpha subunit of the guanine nucleotide binding protein Gq were transiently transfected into NIH3T3 cells and assayed using the functional receptor assay, Receptor Selection and Amplification Technology (R-SAT) essentially as disclosed in U.S. Pat. No. 5,707,798. Each compound was screened at seven serially diluted concentrations in triplicate. Data were analyzed using least squares fit analysis with GraphPad Prism (San Diego, Calif.), and are reported normalized to percent response.

Example 44

Selectivity Profile of Inverse Agonist 26HCH16D

R-SAT assays (as described in Example 42) were carried out with cells transfected with receptors (listed below) to determine the receptor selectivity profile for compound 26HCH16D. 5HT2A inverse agonist data (IC50 nM; % efficacy) were derived from detailed dose response curves (7 points in triplicate). All other data (initial concentration at which at least 30% efficacy observed; actual efficacy figure) derived from the 4 dose profiling protocol in which compounds were tested at 4 doses in duplicate. nr=activity less than 30% at all doses tested (3, 30, 300, 3000 nM), therefore EC50/IC50 greater than 3000 nM). The results are presented in the following table.

TABLE 2

Profile of 5-HT2A Inverse Agonist 26HCH16D

| Receptor | | Efficacy |
|---|---|---|
| 5HT2A (human) | Agonist | nr |
| | Inverse Agonist | 0.9 nM; 79% |
| 5HT2B (human) | Agonist | nr |
| | Antagonist | 3000 nM; 60% |
| 5HT2C (human) | Agonist | nr |
| | Inverse Agonist | 3000 nM; 79% |
| 5HT1A (human) | Agonist | nr |
| | Antagonist | |
| 5HT1A (rat) | Antagonist | nr |

TABLE 2-continued

Profile of 5-HT2A Inverse Agonist 26HCH16D

| Receptor | | Efficacy |
|---|---|---|
| 5HT1E (human) | Agonist | nr |
| D2 (human) | Agonist | nr |
|  | Antagonist | 3000 nM; 73% |
| H1 (human) | Agonist | nr |
|  | Antagonist | 3000 nM; 30% |
| alpha1a/D (rat) | Agonist | nr |
|  | Antagonist | nr |
| alpha1b/B (hamster) | Agonist | nr |
|  | Antagonist | nr |
| alpha1c/A (human) | Agonist | nr |
|  | Antagonist | 3000 nM; 46% |
| alpha2A (human) | Agonist | nr |
|  | Antagonist | nr |
| alpha2B (human) | Agonist | nr |
|  | Antagonist | nr |
| alpha2C (human) | Agonist | nr |
|  | Antagonist | nr |
| m1 (human) | Agonist | nr |
|  | Antagonist | nr |

As indicated above, 26HCH16D is a highly selective 5-HT2A inverse agonist.

General LC-MS Procedure for Working Examples ELH01–46, MBT01–14 and AKU01–38

In the following examples, HPLC/MS analyses were performed using either of two general methods (Method A or Method B). The $t_r$ values reported below were obtained using one of these procedures, as indicated in the specific examples.

The methods were as follows:

Method A: Agilent HP1100 HPLC/MSD.

G1312A Binary pump, G1313A Autosampler, G1316A Column compartment, G1315A Diode array detector (190–450 nm), 1946A MSD, electrospray ionization.

Chromatography:

8 mM ammoniumacetate in water/acetonitrile.

Gradient start at 70% org. up to 100% org. over 12 min, down to 70% org. over 0.5 min, held for 3.5 min. Total runtime 16 min. Flowrate 1 ml/min Column, Phenomenex Luna C18 (2) 3 um 75×4.6 mm.

MS Parameters:

Drying gas, 10 l/min. Nebulizer pressure, 40 psig. Gas temp, 350 C. VCap, 4000.

Method B: Waters/Micromass HPLC/MS

600 LC-pump, 2700 Sample manager, 2487 Dual absorbance detector (channel A-205 nm, channel B-235 nm), Micromass ZMD-mass-spectrometer, electrospray ionization.

Chromatography:

0.15% TFA in water/acetonitrile.

Gradient start at 30% org. up to 100% org. over 10 min, held for 3 min. down to 30% org. over 0.5 min, held for 4.5 min. Total run time 18 min. Flowrate, 1 ml/min.

Column, Symmetry C18, 5 μm, 4.6×50 mm. or 10 mM ammoniumacetate in water/acetonitrile.

Gradient start at 30% org. for 2.5 min, up to 100% org. over 10 min, held for 9 min, down to 30% org. over 0.5 min, held for 5 min. Total run time 27 min. Flowrate, 1 ml/min.

Column: Phenomenex Synergi C12, 4 μm, 4.6×50 mm.

MS Parameters:

Desolvation Gas, 404 l/H. Capillary, 5.3 kV. Cone, 36V. Extractor, 3V. Source Block Temp, 130 C. Desolvation Temp, 250 C.

Example 45

2-(4-methoxyphenyl)-N-(4-methylbenzyl)-N-(piperidin-4-yl)acetamide (50ELH87)

Reaction Step 1: N-trifluoroacetyl-4-piperidone (50ELH84)

4-Piperidone hydrochloride monohydrate (4.0 g, 26 mmol, 1.0 eq) was dissolved in 130 ml of dichloromethane. After addition of triethylamine (8.66 g, 3.3 eq) the reaction mixture was stirred for 10 min. The mixture was cooled on an ice-bath (0° C.). Trifluoroacetic anhydride (12.0 g, 2.2 eq) was added dropwise under stirring. After 2 hours the reaction was quenched by addition of distilled water. The aqueous phase was extracted twice with dichloromethane. The combined organic layers were collected and dried with sodium sulfate. Concentration afforded N-trifluoroacetyl-4-piperidone.

Reaction Step 2: 4-(4-Methylbenzylamino)-1-(trifluoroacetyl)piperidin (50ELH85)

Methanol (150 ml) was added to an Erlenmeyer flask and acetic acid was added under stirring until pH 5.4-Methylbenzylamine (3.14 g, 25.9 mmol) and N-trifluoroacetyl-4-piperidone(from reaction step 1) (5.065 g, 25.9 mmol) were added to a 250 ml round-bottomed flask and dissolved in the methanol/acetic acid (150 ml) solution previously made. The reaction mixture was stirred for 5 min and NaCNBH$_3$ (2.46 g, 38.9 mmol) was added slowly under stirring. After 20 hours the reaction was concentrated and transferred to a separatory funnel containing dichloromethane and distilled water. The aqueous phase was made basic by addition of Na$_2$CO$_3$. The aqueous phase was extracted twice with dichloromethane. The combined organic layers were collected and dried with Na$_2$SO$_4$. Concentration afforded, 4-(4-methylbenzylamine)-1-(trifluoroacetyl)piperidine. UV/MS 60/53 (M$^+$ 301), $t_r$ (A, MS) 3.267.

Reaction Step 3: 2-(4-Methoxyphenyl)-N-(4-methylbenzyl)-N-(1-trifluoroacetylpiperidin-4-yl)acetamide (50ELH86)

The product from reaction step 2 (7.8 g, 25.9 mmol) was dissolved in 100 ml of dichloromethane and stirred while 4-methoxyphenylacetyl chloride (4.8 g, 25.9 mmol) was added. After 4 hours, heptane was added whereupon the product precipitated as the hydrochloride salt. The solvent was removed by evaporation. The crude material was purified by flash chromatography EtOAc/Heptane (1:2) Yield (overall: Reaction steps 1+2+3) 3.912 g (34% ), UV/MS 91/58 (M$^+$ 449), $t_r$ (A, MS) 4.319. $^1$H-NMR (400 MHz, CDCl$_3$) δ 6.80–7.15 (Ar, 4H), 4.64 (brt, 1H), 4.4 (s, 2H), 3.95 (d, 2H), 3.72 (s, 3H), 3.50 (s, 2H), 3.09 (t, 2H), 2.7 (t, 2H), 2.32 (s, 3H), 1.75 (btr, 2H). $^{13}$C-NMR 172.5; 158.8; 137.4; 134.9; 129.9; 129.9; 129.8; 127.1; 125.8; 114.3; 55.4; 52.2; 47.3; 45.3; 43.4.40.6; 30.1; 29.2; 21.2.

Reaction Step 4: 2-(4-Methoxyphenyl)-N-(4-methylbenzyl)-N-(piperidin-4-yl) Acetamide (50ELH87)

The product from reaction step 3 (3.9 g, 8.7 mmol) was dissolved in methanol (12 ml). In a 250 ml round bottom flask a saturated solution of potassium carbonate in methanol was prepared. To this solution, the 2-(4-methoxyphenyl)-N-(4-methylbenzyl)-N-(N-trifluoroacetpiperidin-4-yl)acetamide solution was added under stirring. After 4 hours, the solution was concentrated and the remaining solid taken upin base and dichloromethane. The combined organic layers were dried with sodium sulfate and concentrated. UV/MS 91/72 (M$^+$ 353), $t_r$ (A, MS) 2.210.

The corresponding hydrochloride salt was also prepared, by dissolving the free base in dichloromethane (1 ml) and HCl (1 eq. 2 M HCl in ether) was added with stirring. The salt was precipitated by addition of the dichloromethane solution into heptane. Concentration on the rotary evaporator returned the product is white crystals.

Example 46

2-(4-Methoxyphenyl)-N-(4-methylbenzyl)-N-(1-methylpiperidin-4-yl) acetamide (50ELH27)

Reaction Step 1: 4-(4-Methylbenzylamino)-1-methylpiperidine (50ELH25)

Methanol (50 ml) was added to an Erlenmeyer flask and acetic acid was added under stirring until pH 5. Methylbenzylamine (1.0 g, 8.8 mmol) and 1-Methyl-4-piperidone (1.1 g, 8.8 mmol) were added to a 100 ml round-bottomed flask and dissolved in the methanol/acetic acid (40 ml) solution previously made. The reaction mixture was stirred for 5 min and NaCNBH$_3$ (0.83 g, 13.2 mmol) was added slowly under stirring. After 20 hours the reaction was concentrated and transferred to a separatory funnel containing dichloromethane and distilled water. The aqueous phase was made basic by addition of Na$_2$CO$_3$. The aqueous phase was extracted twice with dichloromethane. The combined organic layers were collected and dried with Na$_2$SO$_4$. Concentration afforded the title compound. Yield (crude): 98%. UV/MS 89/88 (M$^+$ 353), t$_r$ (A, MS) 3.982.

Reaction Step 2: 2-(4-Methoxyphenyl)-N-(4-methylbenzyl)-N-(1-methylpiperidin-4-yl) acetamide (50ELH27)

The product from reaction step 1 (1.9 g, 8.7 mmol) was dissolved in 40 ml of dichloromethane and stirred while 4-methoxyphenylacetylchloride (1.606 g, 8.7 mmol) was added. After 4 hours, heptane was added whereupon the product precipitated as the hydrochloride salt. The solvent was removed by evaporation. The crude material was purified by flash chromatography first eluting with 10% MeOH in CH$_2$Cl$_2$ and thereafter eluting with 0–20% MeOH in CH$_2$Cl$_2$ and 5% NEt$_3$. Yield (overall: Reaction steps 1+2): 77%. UV/MS: 100/100 (M$^+$ 367), t$_r$ (A, MS) 4.359, R$_f$ 0.15 (2% MeOH in CH$_2$Cl$_2$). $^1$H-NMR (400 MHz, CDCl$_3$) δ 12.6 (s, 1H), 7.16 (d, J=7.0 Hz, 2H), 7.10 (d, J=7.0 Hz, 2H), 7.04 (d, J=8.0 Hz, 2H), 6.82 (d, J=8.0 Hz, 2H), 4.87 (tt, J=11.0, 4.0 Hz, 1H), 4.53 ppm (s, 2H), 3.78 (s, 3H), 3.55 (s, 2H), 3.42 (brd, J=11.0 Hz, 2H), 2.80 (brq, J=11.0 Hz, 2H), 2.7 (d, J4.0 Hz, 3H), 2.42 (dq, J=13.0, 3.0 Hz, 2H), 2.34 (s, 3H), 1.78 (brd, J=13.0 Hz, 2H). $^{13}$C-NMR 173.1; 158.9; 137.4; 134.8; 129.9; 126.7; 125.8; 114.4; 76.9; 55.5; 54.6; 48.8; 43.7; 40.5; 26.4; 21.2

Example 47

2-(4-Methoxyphenyl)-N-(4-methylbenzyl)-N-(1-cyclohexylmethylpiperidin-4-yl)acetamide (42ELH45)

50ELH87 (the hydrochloride salt) (0.5 g, 1.29 mmol, 1.0 eq) was dissolved in ethanol (100 ml). Cyclohexanecarboxaldehyde (2.5 g, 20 eq.) was added followed by addition of sodium borohydride (0.084 g, 2.0 eq.). The reaction was stirred for 36 h and acetic acid (3 ml) was added. The reaction was stirred for additionally 2 h and extracted with sodium hydrogen carbonate (3 times) and dichloromethane. The organic layers were dried with sodium sulfate and concentrated. The product was purified by flash chromatography (1–10% MeOH in CH$_2$Cl$_2$). The resulting product was dissolved in ether (20 ml) and MeOH (added dropwise until dissolved) and HCl (1 eq. 2 M HCl in ether) was added under stirring. The hydrochloride salt of 2-(4-methoxyphenyl)-N-(4-methylbenzyl)-N-(1-cyclohexylmethylpiperidin-4-yl) acetamide precipitated and the white crystals were filtered. Yield 80 mg (16%), UV/MS 100/100 (M$^{30}$ 449), r$_t$ (A, MS) 7.105, mp 133–135° C., R$_f$ 0.25 (2% MeOH/CH$_2$Cl$_2$). $^1$H-NMR (400 MHz, CDCl$_3$) δ 11.9 (brs, 1H), 7.12 (q, 4H), 7.02 (d, 2H), 6.80 (d, 2H), 4.87 (m, 1H), 4.58 (s, 2H), 3.77 (s, 3H), 3.55 (s, 2H), 3.48 (m, 2H), 2.70 (m, 4H), 2.31 (s, 3H), 1.91 (d, 2H), 1.75 (m, 3H), 1.64 (d, 1H), 1.22 (d, 2H), 1.13 (tt, 2H), 1.02 (brq, 2H). $^{13}$C-NMR 173.1; 158.8; 137.2; 135.1; 129.9; 129.8; 126.8; 125.8; 114.4; 64.1; 55.5; 53.4; 49.2; 46.5; 40.4; 33.9; 25.9; 25.8; 25.7; 21.2.

Example 48

2-(4-Methoxyphenyl)-N-(4-methylbenzyl)-N-(1-ethylpiperidin-4-yl)acetamide (42ELH80)

50ELH87 (0.25 g, 0.71 mmol, 1.0 eq) was dissolved in acetonitrile (15 ml) and ethyl bromide (0.232 g, 3.0 eq.) was added under stirring. After 2 min Hünings base (0.084 g, 10.0 eq.) was added. After 36 hours, the solution was extracted with sodium hydrogen carbonate solution and dichloromethane (3 times). The organic layers were dried with sodium sulfate and concentrated yielding a yellow oil. The product was purified by flash chromatography (2% MeOH in CH$_2$Cl$_2$). The resulting product was dissolved in dichloromethane (1 ml) and HCl (1 eq. 2 M HCl in ether) was added under stirring. The salt was precipitated by addition of the dichloromethane solution into heptane. Concentration on the rotary evaporator gave the product as white crystals. Yield 170 mg (63%), UV/MS 98/95 (M$^+$ 381), mp 153–155° C., r$_t$ (A, MS) 3.033, R$_f$ 0.35 (3% MeOH/CH$_2$Cl$_2$). $^1$H-NMR (400 MHz, CDCl$_3$) δ 12.2 (s, 1H), 7.15 (d, 2H), 7.12 (d, 2H), 7.08 (d, 2H), 6.82 (d, 2H), 4.89 (m, 1H), 4.58 (s, 2H), 3.79 (s, 3H), 3.58 (s, 2H), 3.50 (d, 2H), 2.90 (m, 1H), 2.7 (brq, 2H), 2.45 (m, 2H), 2.34 (s, 3H), 1.80 (d, 2H), 1.44 (t, 3H). $^{13}$C-NMR 173.1; 158.9; 137.3; 134.9; 129.9; 125.8; 114.4; 55.5; 52.3; 52.0; 49.2; 46.5; 40.5; 26.2; 21.2; 9.5.

Example 49

2-(4-Methoxyphenyl)-N-(4-chlorbenzyl)-N-(1-ethylpiperidin-4-yl) acetamide (42ELH85).

This compound was prepared similarly to 50ELH27

Reaction-Step 1: (42ELH84)

Starting materials: 1-Methyl-4-piperidone (0.5 g, 4.4 mmol, 1.0 eq.), 4-chlorobenzylamine (0.626 g, 1.0 eq.), sodium cyanoborohydride (0.279 g, 1.5 eq.).

Reaction-Step 2: (42ELH85)

Starting materials: 42ELH84, 4-methoxyphenylacetylchloride (0.774 g, 1.0 eq.).

The procedure was analogous to 50ELH27, but the product was purified by ion-exchange chromatography followed by HPLC. The hydrochloride salt was made by dissolving the free base in dichloromethane (1 ml) and HCl (1 eq. 2 M HCl in ether) was added under stirring. The salt was precipitated by addition of the dichloromethane solution into heptane followed by concentration on the rotary evaporator.

Product White crystals. UV/MS 98/97 (M$^+$ 387), r$_t$ (A, MS) 2.953. $^1$H-NMR (400 MHz, CDCl$_3$) δ 12.6 (s, 1H), 7.35 (d, 2H), 7.18 (d, 2H), 7.05 (d, 2H), 6.82 (d, 2H), 4.89 (m, 1H), 4.55 (s, 2H), 3.80 (s, 3H), 3.55 (s, 2H), 3.45 (brs, 2H), 2.80 (brs, 2H), 2.72 (s, 3H), 2.25 (brs, 3H), 1.80 (brs, 2H). $^{13}$C-NMR 173.0; 158.9; 136.5; 133.6; 129.8; 129.4; 127.3; 126.3; 114.5; 55.5; 54.6; 48.7; 46.3; 43.7; 40.5; 26.3.

50-2-(4-Methoxyphenyl)-N-(4-chlorbenzyl)-N-(1-isopropylpiperidin-4-yl)acetamide (42ELH79).

Procedure as 42ELH80

Starting materials: 50ELH87 (0.25 g, 0.71 mmol, 1.0 eq.), isopropylbromide (0.262 g, 3.0 eq.).

Product: Yield 130 mg (46%), UV/MS 100/100 (M+395), r$_t$ (A, MS) 3.360. $^1$H-NMR (400 MHz, CDCl$_3$) δ 12.0 (s, 1H), 7.15 (d, 2H), 7.10 (d, 2H), 7.05 (d, 2H), 6.82 (d, 2H), 4.87 (m, 1H), 4.60 (s, 2H), 3.79 (s, 3H), 3.57 (s, 2H), 3.38 (brd, 3H), 2.79 (q, 2H), 2.63 (q, 2H), 2.34 (s, 3H), 1.80 (d, 2H), 1.39 (d, 6H). $^{13}$C-NMR 173.1; 158.9; 137.3; 135.1; 129.8; 126.8; 125.8; 114.4; 57.9; 49.4; 48.2; 46.5; 40.5; 25.9; 21.2; 16.9.

Example 51

2-(4-Methoxyphenyl)-N-(4-chlorobenzyl)-N-(piperidin-4-yl)acetamide (42ELH89) (As Starting Material in Other Reactions, Used Unpurified)

Procedure as 50ELH27.
Reaction Step 1: N-Trifluoroacetyl-4-piperidone (42ELH86)
Starting materials: 4-Piperidone hydrochloride monohydrate (2.0 g, 13 mmol, 1.0 eq), trifluoroacetic anhydride (6.0, 2.2 eq.). TLC showed full conversion.
Product: R$_f$ 0.9 (10% MeOH/CH$_2$Cl$_2$).
Reaction Step 2: 4-(4-Chlorobenzoylamino)-1-(trifluoroacetyl)piperidin (42ELH87)
Starting materials: 42ELH86 (2.5 g, 12.8 mmol, 1.0 eq.), 4-Chlorobenzylamine (1.8 g, 1.0 eq.)
Reaction Step 3: 2-(4-Methoxyphenyl)-N-(4-chlorbenzyl)-N-(1-trifluoroacetylpiperidin-4-yl)acetamide (42ELH88)
Starting materials: 42ELH87 (4.0 g, 12.5 mmol, 1.0 eq.), 4-methoxyphenylacetylchloride (2.31 g, 1.0 eq.)
Reaction Step 4: 2-(4-Methoxyphenyl)-N-(4-chlorbenzyl)-N-(piperidin-4-yl)acetamide (42ELH89)
Product: Yield: 2 g (57%), UV/MS 80/82 (M$^+$ 373), Rf 0.2 (50% EtOAc/Heptane).

Example 52

2-(4-Methoxyphenyl)-N-(4-chlorbenzyl)-N-(1-cyclopentylpiperidin-4-yl)acetamide (42ELH91).

Procedure as 42ELH80, but the product was purified by HPLC. The acidic eluent was made basic with sodium carbonate and extracted with dichloromethane (3 times). The combined organic layers were collected and dried with sodium sulfate and concentrated. The remaining product was dissolved in 1 ml of dichloromethane and HCl (1 eq. 2 M HCl in ether) was added under stirring. This solution was added drop-wise to a large excess of n-heptane to make the hydrochloride precipitate. The solvent was evaporated off to form white crystals of 2-(4-methoxyphenyl)-N-(4-chlorbenzyl)-N-(1-cyclopentylpiperidin-4-yl)acetamide, hydrochloride.

Starting materials: 42ELH89 (0.25 g, 0.67 mmol, 1.0 eq.), cyclopentylbromide (0.3, 3.0 eq.)

Product: Yield. 211.2 mg (76%). Purification by ion-exchange: UV/MS 90/98. Purification by HPLC UV/MS 100/100 (M$^+$ 441), R$_f$ 0.2 (3% MeOH/CH$_2$Cl$_2$), r$_t$ (A, MS) 4.067. $^1$H-NMR (400 MHz, CDCl$_3$) δ12.2 (brs, 1H), 7.32 (d, 2H), 7.17 (d, 2H), 7.04 (d, 2H), 6.82 (d, 2H), 4.90 (brt, 1H), 4.58 (s, 2H), 3.79 (s, 3H), 3.58 (brd, 2H), 3.54 (s, 2H), 3.14 (brq, 2H), 2.58 (brq, 2H), 2.04 (m, 4H), 1.89 (m, 4H), 1.75 (brd, 2H). $^{13}$C-NMR 173.0; 158.9; 133.5; 129.8; 129.3; 127.3; 126.4; 114.5; 68.4; 55.5; 51.9; 49.1; 46.2; 40.5; 28.5; 26.0; 23.8.

Example 53

2-(4-Methoxyphenyl)-N-(4-chlorbenzyl)-N-(1-isopropylpiperidin-4-yl)acetamide (42ELH90).

42ELH89 (0.25 g, 0.67 mmol, 1.0 eq) was transferred to a 4 ml vial and dissolved in acetonitrile (2 ml). Isopropyl bromide (0.25 g, 3.0 eq.) was added along with Hünigs base (0.87 g, 10.0 eq.). The vial was sealed and shaken for 4 days at 60° C. The reaction mixture was transferred to a separatory funnel with distilled water and CH$_2$Cl$_2$. The aqueous phase was made basic with sodium hydrogen carbonate and extracted with dichloromethane (3 times). The organic layers were collected and dried with sodium sulfate and concentrated, this resulted in a yellow oil. The product was purified by flash chromatography (3% MeOH in CH$_2$Cl$_2$). The resulting product was dissolved in dichloromethane (1 ml) and HCl (1 eq. 2 M HCl in ether) was added under stirring. The salt precipitated by addition of the dichloromethane solution into heptane. Concentration on the rotary evaporator returned the product as white crystals. Yield 101.2 mg (63%), UV/MS 94/96 (M$^+$ 415), R$_f$ 0.25 (3% MeOH/CH$_2$Cl$_2$).

$^1$H-NMR (400 MHz, CDCl$_3$) δ 12.05 (brs, 1H), 7.36 (d, 2H), 7.18 (d, 2H), 7.04 (d, 2H), 6.82 (d, 2H), 4.88 (m, 1H), 4.60 (s, 2H), 3.79 (s, 3H), 3.55 (d, 2H), 3.36 (d, 3H), 2.80 (brq, 2H), 2.65 (brq, 2H), 1.76 (brd, 2H), 1.39 (d, 6H). $^{13}$C-NMR 173.0; 159.0; 137.0; 136.0; 129.7; 129.3; 127.4; 126.4; 114.5; 57.9; 55.5; 49.2; 48.2; 46.2; 40.5; 25.8; 16.9.

Example 54

2-(Phenyl)-N-(4-trifluoromethylbenzyl)-N-(1-methylpiperidin-4-yl)acetamide (50ELH14b)

Procedure as for 50ELH27. Purification was done by HPLC. The hydrochloride salt was made by dissolving the free-base in dichloromethane (1 ml) and HCl (1 eq. 2 M HCl in ether) was added under stirring. The salt was precipitated by addition of the dichloromethane solution into heptane followed by concentration.
Reaction-Step 1: 4-(4-Triflouromethylbenzylamino)-1-methylpiperidin (50ELH2).
Starting materials: 1-Methyl-4-piperidone (1.13 g, 10.0 mmol, 1.0 eq.), 4-trifluoromethylbenzylamine (1.75 g, 1.0 eq.).
Product: UV/MS 80/92 (M+273).
Reaction-Step 2: 2-(Phenyl)-N-(4-trifluoromethylbenzyl)-N-(1-methylpiperidin-4-yl) acetamide (50ELH14b).
Starting materials: 50ELH2 (0.12 g, 0.44 mmol, 1.0 eq.), phenylacetylchloride (0.068 g, 1.0 eq.).
Product: UV/MS 100/97 M$^+$ 390), r$_t$ (A, MS) 3.797, R$_f$ 0.3 (5% MeOH/CH$_2$Cl$_2$). $^1$H-NMR (400 MHz, CDCl$_3$, rotamers 54/46) δ 7.52 (d, 2H), 7.42 (d, 2H), 7.12 7.30 (m, 4H,), 4.63 and 3.74 (2m, 1H), 4.38 (brs, 2H), 3.80 and 3.50 (2s, 3H), 3.31 and 2.78 (2d, 2H), 2.33 and 2.18 (2s, 2H), 2.24 and 1.65–1.90 (t and m, 4H), 1.60 and 1.22 (2d, 2H), 1. $^{13}$C-NMR 172.3; 171.8; 143.9; 135.1; 134.8; 129.1; 129.0; 128.9; 128.7; 127.4; 127.3; 127.2; 126.3; 126.1; 126.0; 56.0; 55.2; 54.9; 50.9; 46.8; 45.2; 44.9; 42.2; 41.7; 30.6; 28.4.

Example 55

2-(4-Fluorophenyl)-N-(4-trifluoromethylbenzyl)-N-(1-methylpiperidin-4-yl)acetamide (50ELH14c)

Procedure as 50ELH14B.

Reaction-Step 2: 2-(4-Fluorophenyl)-N-(4-trifluoromethylbenzyl)-N-(1-methylpiperidin-4-yl)acetamide (50ELH14c).

Starting materials: 50ELH2 (0.12 g, 0.44 mmol, 1.0 eq.), 4-fluorophenylacetylchloride (0.076 g, 1.0 eq.).

Product: Yield 69.7 mg (36%), UV/MS 100/98 (M$^+$ 409), r$_t$ (A, MS) 3.839, R$_f$ 0.3 (5% MeOH/CH$_2$Cl$_2$). $^1$H-NMR (400 MHz, DMSO, rotamers 65/35) δ 10.80 and 10.60 (2s, 1H), 7.71 and 7.62 (2d, 2H), 7.47 and 7.38 (2d, 2H), 7.00-7.36 (t and m, 4H), 4.70 and 4.50 (2s, 2H), 4.30 (m, 1H), 3.93 and 3.56 (2s, 2H), 3.34 (s, 2H), 3.00 (brq, 2H), 2.64 (s, 3H), 2.08 (m, 2H), 1.68 and 1.58 (2d, 2H). $^{13}$C-NMR 176.8; 176.4; 167.6; 165.3; 150.0; 149.0; 136.6; 132.5; 131.0; 130.5; 120.6; 120.5; 120.5; 120.4; 58.1; 58.0; 57.0; 54.5; 52.0; 49.3; 47.6; 45.0; 32.4; 31.4.

Example 56

2-(4-Methoxyphenyl)-N-(4-trifluoromethylbenzyl)-N-(1-methylpiperidin-4-yl)acetamide (50ELH14d)

Procedure as 50ELH14B.

Reaction-Step 2: 2-(4-Methoxyphenyl)-N-(4-trifluoromethylbenzyl)-N-(1-methylpiperidin-4-yl)acetamide (50ELH14d).

Starting materials: 50ELH2 (0.15 g, 0.55 mmol, 1.0 eq.), 4-methoxyphenylacetylchloride (0.1 g, 1.0 eq.).

Product: Yield 57.5 mg (29%), UV/MS 99/100 (M$^+$ 421), r$_t$ (B, MS) 6.30, R$_f$ 0.25 (3% MeOH/CH$_2$Cl$_2$). $^1$H-NMR (400 MHz, CDCl$_3$) δ 12.4 (brs, 1H), 7.55 (d, 2H), 7.28 (d, 2H), 6.96 (d, 2H), 4.84 (brt, 1H), 4.59 (s, 2H), 3.72 (s, 3H), 3.46 (s, 2H), 3.38 (d, 2H), 2.78 (q, 2H), 2.64 (s, 3H), 2.38 (q, 2H), 1.70 (d, 2H). $^{13}$C-NMR 173.0; 159.0; 142.3; 130.0; 129.8; 126.3; 126.2; 114.7; 114.5; 55.5; 54.4; 48.7; 46.5; 43.6; 40.6; 26.3.

Example 57

2-(4-Trifluoromethylphenyl)-N-(4-trifluoromethylbenzyl)-N-(1-methylpiperidin-4-yl)acetamide (50ELH14a)

Procedure as 50ELH14B.

Reaction-Step 2: 2-(4-Trifluoromethylphenyl)-N-(4-trifluoromethylbenzyl)-N-(1-methylpiperidin-4-yl)acetamide (50ELH14a).

Starting materials: 50ELH2 (0.12 g, 0.44 mmol, 1.0 eq.), 4-trifluoromethylphenylacetylchloride (0.1 g, 1.0 eq.).

Product: Yield 92.6 mg (42%), UV/MS 89/93 (M$^+$ 458), r$_t$ (A, MS) 4.211, R$_f$ 0.3 (5% MeOH/CH$_2$Cl$_2$). $^1$H-NMR (400 MHz, CDCl$_3$) δ 12.7 (brs, 1H), 7.56 (d, 2H), 7.48 (d, 2H), 7.17 (d, 2H), 4.86 (m, 1H), 4.63 (s, 2H), 3.58 (s, 3H), 3.40 (d, 2H), 2.75 (q, 2H), 2.65 (d, 3H), 2.46 (dq, 2H), 1.73 (brs, 2H). $^{13}$C-NMR 171.8; 141.9; 138.4; 129.4; 127.9; 126.3; 126.3; 126.2; 125.9; 125.8; 54.4; 48.8; 46.6; 43.6; 40.9; 26.2.

Example 58

2-(4-Fluorophenyl)-N-(4-fluorobenzyl)-N-(1-methylpiperidin-4-yl)acetamide (50ELH6)Procedure as 50ELH14B.

Reaction-Step 1: 4-(4-Fluorobenzylamino)-1-methylpiperidine (50ELH4).

Starting materials: 1-Methyl-4-piperidone (1.13 g, 10.0 mmol, 1.0 eq.), 4-fluorobenzylamine (1.25 g, 1.0 eq.).

Product: Yield 2.154 g (97%), UV/MS 79/89 (M$^+$ 223).

Reaction-Step 2: 2-(4-Fluorophenyl)-N-(4-fluorobenzyl)-N-(1-methylpiperidin-4-yl)acetamide (50ELH14a).

Starting materials: 50ELH4 (0.12 g, 0.54 mmol, 1.0 eq.), 4-fluorophenylacetylchloride (0.096 g, 1.0 eq.).

Product: Yield 57 mg (29%), UV/MS 100/100 (M$^+$ 359), r$_t$ (A, MS) 3.763, R$_f$ 0.25 (3% MeOH/CH$_2$Cl$_2$). $^1$H-NMR (400 MHz, CDCl$_3$) 67 12.6 (brs, 1H), 7.2 (dd, 2H), 7.06 (m, 4H), 6.98 (t, 2H), 4.88 (tt, 1H), 4.58 (s, 4H), 3.45 (d, 2H), 2.81 (q, 2H), 2.72 (d, 3H), 2.48 (brq, 2H), 1.78 (brs, 2H). $^{13}$C-NMR 172.5; 163.4; 160.8; 133.4; 130.6; 130.2; 127.5; 127.4; 116.3; 116.1; 115.9; 115.7; 54.5; 48.8; 46.2; 43.6; 40.3; 26.3.

Example 59

2-(4-Methoxyphenyl)-N-(4-fluorobenzyl)-N-(1-methylpiperidin-4-yl)acetamide (50ELH8).

Procedure as 50ELH14B

Reaction-Step 2:

Starting materials: 50ELH4 (0.12 g, 0.54 mmol, 1.0 eq.), 4-methoxyphenylacetylchloride (0.1 g, 1.0 eq.).

Product: Yield 54 g (26%), UV/MS 100/100 (M$^+$ 371), r$_t$ (A, MS) 3.257, R$_f$ 0.25 (3% MeOH/CH$_2$Cl$_2$). $^1$H-NMR (400 MHz, CDCl$_3$) 67 12.2 (brs, 1H), 7.12 (m, 2H), 6.97 (m, 4H), 6.75 (d, 2H), 4.80 (brt, 1H), 4.49 (s, 2H), 3.71 (s, 3H), 3.47 (s, 2H), 3.37 (d, 2H), 2.8 (q, 2H), 2.64 (s, 3H), 2.35 (q, 2H), 1.69 (d, 2H). $^{13}$C-NMR 173.0; 163.5; 161.1; 158.9; 133.7; 133.6; 129.8; 127.6; 127.5; 126.5; 116.2; 116.0; 114.6; 114.5; 55.5; 54.4; 48.8; 46.2; 43.6; 40.5; 26.4.

Example 60

2-(Phenyl)-N-(4-fluorobenzyl)-N-(1-methylpiperidin-4-yl)acetamide (50ELH10)

Procedure as 50ELH14B.

Reaction-Step 2: 2-(Phenyl)-N-(4-fluorobenzyl)-N-(1-methylpiperidin-4-yl)acetamide (50ELH10).

Starting materials: 50ELH4 (0.13 g, 0.59 mmol, 1.0 eq.), phenylacetylchloride (0.091 g, 1.0 eq.).

Product: UV/MS 100/94 (M$^+$ 341), r$_t$ (A, MS) 3.127, R$_f$ 0.25 (3% MeOH/CH$_2$Cl$_2$). $^1$H-NMR (400 MHz, DMSO, rotamers 54/56) δ 12.38 (brs, 1H), 7.35–7.00 (m, 9H), 4.55 and 4.40 (2s, 2H), 4.50 and 4.25 (brt, 1H), 3.91 and 3.56 (2s, 2H), 3.30 (Hidden under water signal) (2H), 2.98 (d, 2H), 2.64 (s, 3H), 2.09 (brt, 2H), 1.66 and 1.45 (2brd, 2H). $^{13}$C-NMR 171.9; 171.6; 162.8; 160.4; 136.5; 136.2; 135.4; 129.9; 129.7; 129.5; 129.2; 129.0; 128.9; 128.7; 127.2; 127.1; 116.2; 116.0; 115.6; 53.2; 52.5; 49.8; 46.9; 44.0; 42.8; 40.9; 40.6; 40.4; 40.2; 40.0; 39.8; 39.6; 27.7; 26.6.

Example 61

2-(4-Trifluoromethylphenyl)-N-(4-fluorobenzyl)-N-(1-methylpiperidin-4-yl)acetamide (50ELH12$^2$)

Procedure as 50ELH14B.

Reaction Step 0: 4-Trifluoromethyphenylacetyl chloride (50ELH12$^1$)

4-Trifluorophenylacetic acid (1.0 g) and thionyl chloride (15 ml) were refluxed for 1 h. The excess thionyl chloride was evaporated off. NMR showed complete conversion.

Reaction-Step 2: 2-(4-Trifluoromethlphenyl)-N-(4-fluorobenzyl)-N-(1-methylpiperidin-4-yl)acetamide (50ELH1 22).

Starting materials: 50ELH4 (0.12 g, 0.55 mmol, 1.0 eq.), 4-trifluoromethylphenylacetylchloride (50ELH12[1]) (0.11 g, 0.5 mmol, 1.0 eq.).

Product: Yield 47.1 mg (24%), UV/MS 96/96 (M⁺ 409), $r_t$ (A, MS) 4.566, $R_f$ 0.25 (3% MeOH/CH$_2$Cl$_2$). ¹H-NMR (400 MHz, CDCl$_3$)o 7.52 (d, 2H), 7.22 (d, 2H), 7.17 (dd, 2H), 7.04 (t, 2H), 4.86 (brt, 1H), 4.58 (s, 2H), 3.64 (s, 2H), 3.45 (brd, 2H), 2.84 (brq, 2H), 2.71 (d, 3H), 2.45 (brq, 2H), 1.77 (brd, 2H). ¹³C-NMR 171.8; 163.6; 161.2; 138.7; 133.3; 129.8; 129.5; 127.5; 127.4; 125.8; 125.7; 116.4; 116.2; 54.4; 48.9; 46.3; 43.6; 40.8; 26.3.

Example 62

4-(4-Methoxybenzylamino)-1-methylpiperidine (50ELH18).

Procedure as 50ELH27.

Starting materials: 1-Methyl-4-piperidone (1.13 g, 10.0 mmol, 1.0 eq.), 4-methoxybenzylamine (1.37 g, 1.0 eq.).

Product: UV/MS 95/95 (M⁺ 235), $r_t$ (A, MS) 3.509. ¹H-NMR (400 MHz, CDCl$_3$) δ 7.3–6.8 (m, 4H), 3.77 (s, 3H), 3.73 (s, 2H), 2.86 (m, 2H), 2.55 (m, 1H), 2.30 (s, 3H), 2.1 (t, 2H), 1.96 (dd, 2H), 1.50 (m, 2H).

Example 63

2-(4-Trifluoromethylphenyl)-N-[4-(methoxycarbonyl)benzyl]-N-(1-methylpiperidin-4-yl)acetamide (50ELH20A)

Procedure as 50ELH14B.

Reaction-Step 1: Methyl 4-(N-[1-methylpiperidine-4-yl]aminomethyl) benzoate (50ELH19).

Starting materials: 1-Methyl-4-piperidone (1.13 g, 10.0 mmol, 1.0 eq.), methyl 4-(aminomethyl)benzoate hydrochloride (2.0 g, 1.0 eq.).

Product: UV/MS 81/88 (M⁺ 263), $r_t$ (A, MS) 3.060. ¹H-NMR (400 MHz, CDCl$_3$) δ 8.00 (d, 2H), 7.20 (d, 2H), 3.90 (s, 3H), 3.85 (s, 2H), 2.96 (dt, 2H), 2.7 (brs, 1H), 2.62 (m, 1H), 2.40 (s, 3H), 2.28 (t, 2H), 1.96 (m, 2H), 1.56 (m, 2H).

Reaction-Step 2: 2-(4-Trifluoromethylphenyl)-N-[4-(methoxycarbonyl)benzyl]-N-(1-methylpiperidin-4-yl) acetamide (50ELH20A).

Starting materials: 50ELH19 (0.20 g, 0.76 mmol, 1.0 eq.), 50ELH12[1] (0.169 g, 1.0 eq.).

Product: Yield 108.9 mg (32%), UV/MS 100/100 (M⁺ 448), $r_t$ (A, MS) 3.327, $R_f$ 0.3 (5% MeOH/CH$_2$Cl$_2$). ¹H-NMR (400 MHz,DMSO, rotamers 56/44) δ 10.7 and 10.4 (2brs, 1H), 7.96–7.28 (m, 8H), 4.70 and 4.51 (2s, 2H), 4.30 (brt, 1H), 4.06 and 3.69 (2s, 2H), 3.83 and 3.81 (2s, 3H), 3.00 (m, 2H), 2.63 (m, 3H), 2.05 (brt, J=12 Hz, 2H), 1.69 (brt, J=12 Hz, 2H). ¹³C-NMR (CDCl$_3$) 171.9; 166.7; 142.9; 138.5; 130.7; 130.1; 129.7; 126.2; 125.9; 55.2; 52.5; 49.2; 47.4; 41.2; 32.1; 26.6; 22.9; 14.3.

Example 64

2-Phenyl-N-[4-(methoxycarbonyl)benzyl]-N-(1-methylpiperidin-4-yl) acetamide (50ELH20B)

Procedure as 50ELH14B

Reaction-Step 2: 2-Phenyl-N-[4-(methoxycarbonyl)benzyl]-N-(1-methylpiperidin-4-yl) acetamide (50ELH20B).

Starting materials: 50ELH19 (0.2 g, 0.76 mmol, 1.0 eq.), phenylacetylchloride (0.117 g, 1.0 eq.).

Product: Yield 82.5 g (29%), UV/MS 100/100 (M⁺ 381), $r_t$ (A, MS) 2.652, $R_f$ 0.25 (30% MeOH/CH$_2$Cl$_2$). ¹H-NMR (400 MHz, CDCl$_3$) δ 12.2 (brs, 1H), 8.00 (d, J=7.4, 2H), 7.4–7.2 (m, 4H), 7.08 (d, J=7.4, 2H), 4.89 (brt, 1H), 4.62 (s, 2H), 3.90 (s, 3H), 3.56 (s, 2H), 3.42 (d, J=11.0, 2H), 2.84 (q, J=11.0, 2H), 2.68 (d, J=3.6, 3H), 240 (q, J=11.0, 2H), 1.77 (brd, J=11.0, 2H). ¹³C-NMR 173.0; 168.0; 143.3; 136.7; 130.6; 129.0; 127.4; 125.9; 54.5; 52.4; 48.8; 43.6; 41.4; 26.3.

Example 65

2-(4-Chlorophenyl)-N-[4-(methoxycarbonyl)benzyl]-N-(1-methylpiperidin-4-yl) acetamide (50ELH20C).

Procedure as 50ELH14B.

Reaction-Step 2: 2-(4-Chlorophenyl)-N-[4-(methoxycarbonal)benzyl]-N-(1-methylpiperidin-4-yl) acetamide (50ELH20C).

Starting materials: 50ELH19 (0.2 g, 0.76 mmol, 1.0 eq.), 4-chlorophenylacetylchloride (0.131 g, 1.0 eq.).

Product: Yield 79.2 g (26%), UV/MS 100/96 (M⁺ 399), $r_t$ (A, MS) 2.333. ¹H-NMR (400 MHz, DMSO, rotamers 62/38) δ 10.8 and 10.60 (2brs, 1H), 7.95 and 7.85 (2d, J=8.6, 2H), 7.4 and 7.28 (2d, 2H), 7.35 and 7.14 (2m, 4H), 4.67 and 4.50 (2s, 2H), 4.29 (m, 1H), 3.93 and 3.84 (2s, 2H), 3.81 (s, 3H), 3.21 (d, J=11.9, 2H), 3.00 (d, J=11.9, 2H), 2.63 (s, 3H), 2.06 (m, 2H), 1.68 and 1.56 (d, J=11.9, 2H). ¹³C-NMR (CDCl$_3$) 172.6; 166.7; 163.4; 161.0; 143.0; 130.7; 130.6; 130.5; 126.0; 115.9; 115.7; 54.7; 52.4; 48.9; 46.9; 44.0; 40.4; 26.4.

Example 66

2-(4-Methoxyphenyl)-N-[4-(methoxycarbonyl)benzyl]-N-(1-methylpiperidin-4-yl) acetamide (50ELH20D).

Procedure as 50ELH14B.

Reaction-Step 2: 2-(4-Methoxyphenyl)-N-[4-(methoxycarbonyl)benzyl]-N-(1-methylpiperidin-4-yl) acetamide (50ELH20D).

Starting materials: 50ELH19 (0.2 g, 0.76 mmol, 1.0 eq.), 4-methoxyphenylacetylchloride (0.140 g, 1.0 eq.).

Product: Yield 108.6 g (26%), UV/MS 100/99 (M⁺ 410), $r_t$ (A, MS) 2.280. ¹H-NMR (400 MHz, CDCl$_3$) δ 12.38 (brs, 1H), 8.00 (d, J=7.2, 2H), 7.28 (d, J=7.2, 2H), 7.00 (d, J=7.2, 2H), 6.79 (d, J=7.2, 2H), 4.88 (brt, 1H), 4.61 (s, 2H), 3.90 (s, 3H), 3.75 (s, 3H), 3.42 (brd, J=10.7, 2H), 2.84 (q, J=10.7, 2H), 2.68 (d, J=3.6, 3H), 2.40 (brq, J=10.7, 2H1), 1.75 (d, J=10.7, 2H). ¹³C-NMR 173.0; 166.8; 159.0; 143.3; 130.5; 129.9; 129.8; 126.3; 125.9; 114.5; 55.5; 54.7; 52.4; 48.7; 46.7; 43.6; 40.6; 32.1; 26.3; 22.9; 14.3.

Example 67

2-(4-TMethylphenyl)-N-[4-(methoxycarbonyl)benzyl]-N-(1-methylpiperidin-4-yl) acetamide (50ELH23)

Procedure as 50ELH14B.

Reaction-Step 2: 1-Phenyl-N-[2-(4-methylphenyl)ethyl]-N-(1-methylpiperidin-4-yl) amide (50ELH23).

Starting materials: 4-(2-Phenylethyl)amino-1-methylpiperidine (0.20 g, 0.86 mmol, 1.0 eq.), benzoylchloride (0.158 g, 1.0 eq.).

Product: Yield 159 mg (50%), UV/MS 100/100 (M⁺ 337), $r_t$ (A, MS) 3.289, $R_f$ 0.55 (10% MeOH/CH$_2$Cl$_2$). ¹H-NMR (400 MHz, DMSO (80° C.)) δ 10.9 (brs, 1H), 7.44 (s, 2H), 7.34 (d, J=3.0 Hz, 2H), 7.04 (d, J=7.0 Hz, 2H), 6.95 (brs, 2H), 4.00 (brs, 1H), 3.40 (d, J=4.2 Hz, 2H), 3.35 (d, J=4.2 Hz, 2H), 2.95 (brs, 2H), 2.77 (t, J=3.2 Hz, 2H), 2.40 (q, J=6.4 Hz, 2H), 2.24 (s, 3H) 1.83 (d, J=6.4 Hz, 2H). $^{13}$C-NMR (CDCl$_3$) 171.6; 138.1; 136.3; 136.0; 129.8; 129.6; 129.1; 129.1; 126.7; 53.6; 52.4; 46.1; 42.9; 35.9; 27.3; 21.1.

Example 68

2-(4-Methoxyphenyl)-N-(3-phenyl-1-propyl)-N-(1-methylpiperidin-4-yl) acetamide (50ELH65)

Procedure as 50ELH14B.

Reaction-Step 1: 4-(3-Phenylaminopropyl)piperidine (50ELH59)

Starting materials: 1-Methyl-4-piperidone (1.1 ml, 7.4 mmol, 1.0 eq.), 3-phenylpropylamine (1.35 g, 1.0 eq.).

Product. UV/MS 100/94 (M$^+$ 233), r$_t$ (A, MS) 3.534.). $^1$H-NMR (400 MHz, CDCl$_3$) δ 7.28–7.12 (m, 5H), 3.40 (brs, 1H), 2.84 (dt, J=12.3 and 3.5 Hz, 2H), 2.94 (g, J=7.0 Hz, 4H), 2.51 (m, 1H), 2.27 (s, 3H), 2.05 (brt, J=12.3 Hz, 2H), 1.82 (m, 2H), 1.44 (m, 2H).

Reaction-Step 2: 2-(4-Methoxyphenyl)-N-(3-phenyl-1-propyl)-N-(1-methylpiperidin-4-yl) acetamide (50ELH65)

Starting materials: 50ELH59 (0.50 g, 2.2 mmol, 1.0 eq.), 4-methoxyphenylacetylchloride (0.398 g, 1.0 eq.).

Product: Yield 153 mg (43%), UV/MS 100/100 (M$^+$ 381), r$_t$ (A, MS) 2.938. $^1$H-NMR (400 MHz, DMSO, rotamers 55/45) δ 11.0 and 10.90 (2brs, 1H), 7.30–7.10 (m, J=7.9 Hz, 6H), 6.97 (d, J=7.9 Hz, 1H), 4.22 and 4.06 (2dt, dH), 3.70 (s, 3H), 3.35 (t, J=10.4 Hz, 2H), 3.15 (m, 2H), 3.00 (q, J=10.4 Hz, 2H), 2.66 (d, 3H), 2.52 (q, J=7.9 Hz, 2H), 2.17 (brq, J=12 Hz, 2H) 1.73 (m, 2H), 1.70 and 1.52 (2d, J=12 Hz, 2H). $^{13}$C-NMR (DMSO) 171.3; 171.0; 158.6; 142.2; 141.7; 130.0; 129.0; 128.0; 128.5; 128.2; 126.6; 114.5; 55.7; 55.7; 53.5; 53.3; 50.1; 44.5; 42.9; 41.9; 33.7; 33.1; 32.9; 31.4; 27.8; 26.8.

Example 69

2-(4-Methoxyphenyl)-N-[2-(4-methylphenyl)ethyl]-N-(1-methylpiperidin-4-yl) acetamide (50ELH68)

Procedure as 50ELH14B

Reaction-Step 1: 4-[2-(4-Methylphenyl)ethylamino]-piperidin (50ELH58)

Starting materials: 1-Methyl-4-piperidone (1.1 ml, 7.4 mmol, 1.0 eq.), 2-(4-methylphenyl)ethylamine (1.0 g, 1.0 eq.).

Product: UV/MS 100/91 (M$^+$ 233), r$_t$ (A, MS) 3.933.). $^1$H-NMR (400 MHz, CDCl$_3$) δ 7.4 (s, 5H), 3.27 (brs, 1H), 2.84 (d, J=7.0 Hz, 4H), 2.75 (m, 2H), 2.54 (m, 1H), 2.29 (2xs, 6H), 2.10 (brt, J=12.3 Hz, 2H), 1.86 (brd, 2H), 1.45 (m, 2H).

Reaction-Step 2: 2-(4-Methoxyphenyl)-N-[2-(4-methylphenyl)ethyl]-N-(1-methylpiperidin-4-yl) acetamide (50ELH68)

Starting materials: 50ELH58 (0.30 g, 1.3 mmol, 1.0 eq.), 4-methoxyphenylacetylchloride (0.238 g, 1.0 eq.).

Product: Yield 125 mg (26%), UV/MS 100/99 (M$^+$ 381), r$_t$ (A, MS) 3.156. $^1$H-NMR (400 MHz, DMSO, rotamers 50/50) δ 11.0 and 10.90 (2brs, 1H), 7.25–7.04 (m, J=8.7 Hz, 6H), 6.87 and 6.84 (2d, J=8.7 Hz, 2H), 4.30 and 4.09 (2dt, J=11.5 Hz, dH), 3.73 and 3.58 (2s, 2H), 3.71 and 3.70 (2s, 3H), 3.35 (m, (Underneath waterpeak) 3H), 3.24 (m, 1H), 3.02 (m, J=11.5 Hz, 2H), 2.80–2.62 (m, 5H), 2.32 and 2.20 (2q, J=11.5Hz, 2H), 2.26 and 2.24 (2s, 3H) 1.78 and 1.49 (2d, J=11.5 Hz, 2H). $^{13}$C-NMR (DMSO) 171.5; 171.2; 158.6; 136.8; 136.2; 136.0; 135.8; 130.7; 130.5; 129.7; 129.6; 129.4; 129.2; 128.4; 128.3; 114.5; 55.8; 55.7; 53.3; 53.3; 52.2; 50.2; 46.8; 43.9; 42.9; 36.8; 35.2; 27.6; 26.8; 21.3.

Example 70

2-(4-Methoxyphenyl)-N-[2-(2-thionyl)ethyl]-N-(1-methylpiperidin-4-yl) acetamide (50ELH71A)

Procedure as 50ELH14B

Reaction-Step 1: 4-[2-(2-Thienyl)ethylamino]piperidin (50ELH67A)

Starting materials: 1-Methyl-4-piperidone (0.5 g, 4.4 mmol, 1.0 eq.), thiophene-2-ethylamine (0.563 g, 1.0 eq.).

Product: UV/MS 94/93 (M$^+$ 225).

Reaction-Step 2: 2-(4-Methoxyphenyl)-N-[2-(2-thienylethyl]-N-(1-methylpipieridin-4-yl) acetamide (50ELH71A)

Starting materials: 50ELH67A (0.243 g, 1.08 mmol, 1.0 eq.), 4-methoxyphenylacetylchloride (0.2 g, 1.0 eq.).

Product: Yield 80.7 mg (33%), UV/MS 100/100 (M$^+$ 373), r$_t$ (A, MS) 2.613. $^1$H-NMR (400 MHz, DMSO, rotamers 50/50) δ 10.8 and 10.6 (2brs, 1H), 7.36 and 7.31 (2d, J=4.7 Hz, 1H), 7.20 and 7.06 (2d, J=8.3 Hz, 2H), 7.00–6.92 (m, J=4.7 and 2.8 Hz, 2H), 6.87 and 6.40 (2d, J=8.3 Hz, 2H), 4.22 and 4.08 (2dt, J=12.2 Hz, 1H), 3.71 (s, 3H), 3.70 (s, 2H), 3.46–3.30 (m, 4H), 3.10–2.90 (m, 4H), 2.67 (m, 2H), 2.28 and 2.12 (2q, J=12 Hz, 2H), 1.80 and 1.50 (2d, J=12 Hz, 2H). $^{13}$C-NMR (DMSO) 172.5; 158.9; 139.6; 130.0; 129.6; 126.8; 124.5; 114.5; 55.5; 54.7; 49.3; 45.8; 43.8; 41.3; 31.9; 29.9

Example 71

2-(4-Methoxyphenyl)-N-[2-(4-nitrophenyl)ethyl]-N-(1-methylpiperidin-4-yl) acetamide (50ELH71C)

Procedure as 50ELH14B

Reaction-Step 1: 4-[2-(4-nitrophenyl)ethylamino]-piperidin (50ELH67C)

Starting materials: 1-Methyl-4-piperidone (0.5 g, 4.4 mmol, 1.0 eq.), 4-nitrophenyl-2-ethylamine (0.897 g, 1.0 eq.).

Product: UV/MS 96/89 (M$^+$ 264), r$_t$ (A, MS) 3.264.

Reaction-Step 2: 2-(4-Methoxyphenyl)-N-[2-(4-nitrophenyl)ethyl]-N-(1-methylpiperidin-4-yl) acetamide (50ELH71A)

Starting materials: 50ELH67C (0.285 g, 1.08 mmol, 1.0 eq.), 4-methoxyphenylacetylchloride (0.2 g, 1.0 eq.).

Product: Yield 130.9 mg (30%), UV/MS 100/100 (M$^+$ 412), r$_t$ (A, MS) 2.219. $^1$H-NMR (400 MHz, DMSO, rotamers 50/50) δ 10.8 and 10.6 (2brs, 1H), 8.17 and 8.12 (2d, J=8.6 Hz, 2H), 7.58 and 7.48 (2d, J=8.6 Hz, 2H), 7.2 and 7.1 (2d, J=8.6 Hz, 2H), 6.87 and 6.40 (2d, J=8.6 Hz, 2H), 4.25 and 4.10 (2dt, J=12 Hz, 1H), 3.72 (s, 3H), 3.70 (s, 2H), 3.48–3.30 (m, 4H), 3.10–2.84 (m, 4H), 2.69 and 2.67 (2d, J=4.7 Hz, 3H), 2.34 and 2.15 (2q, J=13.2 Hz, 2H), 1.79 and 1.47 (2d, J=13.2 Hz, 2H).

Example 72

2-(4-Methoxyphenyl)-N-(2-thienylmethyl)-N-(1-methylpiperidin-4-yl) acetamide (50ELH73A)

Procedure as 50ELH14B.

Reaction-Step 1: 4-[(2-Thienylmethyl)amino]-1-methylpiperidine (50ELH66A)

Starting materials: 1-Methyl-4-piperidone (0.5 g, 4.4 mmol, 1.0 eq.), 2-thienylmethylamine(0.52 g, 1.0 eq.).

Product: UV/MS 77/86 (M$^+$ 211), r$_t$ (A,MS) 2.739.

Reaction-Step 2: 2-(4-Methoxyphenyl)-N-(2-thienylmethyl)-N-(1-methylpiperidin-4-yl) acetamide (50ELH73A)

Starting materials: 50ELH66A (0.228 g, 1.08 mmol, 1.0 eq.), 4-methoxyphenylacetylchloride (0.2 g, 1.0 eq.).

Product: Yield 178.4 mg (50%), UV/MS 100/98 (M$^+$ 359), r$_t$ (A, MS) 3.117. $^1$H-NMR (400 MHz, DMSO) δ 10.9 and 10.6 (2brs, 1H), 7.47 and 7.32 (2d, J=4.5 Hz, 1H), 7.20 and 7.03 (2d, J=8.4 Hz, 2H), 7.03 and 6.98 (2m, 1H), 6.87 (m, 3H), 4.70 and 4.57 (2s, 2H), 4.42 and 4.16 (2t, J=11.9 Hz, 1H), 3.77 and 3.60 (2s, 2H), 3.51 (s, 3H), 3.15 (m, 2H), 2.98 (m, J=11.9 Hz, 2H), 2.65 (2d, J=4.5 Hz, 3H), 2.25 and 2.17 (2q, J=11.9 Hz, 2H), 1.69 and 1.44 (2d, J=11.9 Hz, 2H). $^{13}$C-NMR (DMSO) 171.4; 158.6; 143.2; 130.7; 128.1; 126.6; 126.3; 125.9; 114.5; 55.7; 53.3; 52.6; 50.0; 42.8; 27.7; 26.8.

Example 73

2-(4-Methoxyphenyl)-N-(furfuryl)-N-(1-methylpiperidin-4-yl) acetamide (50ELH73B).

Procedure as 50ELH14B.

Reaction-Step 1: 4-(Furfurylamino)-1-methylpiperidin (50ELH66B)

Starting materials: 1-Methyl-4-piperidone (0.5 g, 4.4 mmol, 1.0 eq.), Furfurylamine (0.43 g, 1.0 eq.).

Product: UV/MS 77/92 (M$^+$ 195), r$_t$ (A, MS) 2.812.).

Reaction-Step 2: 2-(4-Methoxyphenyl)-N-(furfuryl)-N-(1-methylpiperidin-4-yl) acetamide (50ELH73B).

Starting materials: 50ELH66B (0.21 g, 1.08 mmol, 1.0 eq.), 4-methoxyphenylacetylchloride (0.2 g, 1.0 eq.).

Product: Yield 134 mg (36%), UV/MS 100/99 (M$^+$ 343), r$_t$ (A, MS) 2.401. $^1$H-NMR (400 MHz, DMSO, rotamers 57/43) δ 10.95 and 10.75 (2brs, 1H), 7.63 and 7.48 (s, 1H), 7.18 and 7.06 (2d, J=7.7 Hz, 2H), 6.85 (t, J=7.7 Hz, 2H), 6.44 and 6.33 (2d, J=7.7 Hz, 1H), 6.37 and 6.11 (2s, 1H) 4.5 and 4.34 (2s, 2H), 4.42 and 4.18 (2dt, J=11 and 2 Hz, 1H), 3.75 and 3.65 (2s, 2H) 3.70 (s, 3H), 3.33 (hidden, 2H), 3.0 (q, 2H), 2.64 (d, J=4.7 Hz, 3H), 2.15 (dq, J=11 and 2 Hz, 2H), 1.65 and 1.50 (2d, J=11 Hz, 2H).

Example 74

2-(2-thienylmethyl)-N-(4-methylphenylmethyl)-N-(1-methylpiperidin-4-yl) acetamide (50ELH82)

Procedure as 50ELH14B

Reaction-Step 2: 2-(2-thienylmethyl)-N-(4-methylphenylmethyl)-N-(1-methylpiperidin-4-yl) acetamide (50ELH82)

Starting materials: 50ELH25 (0.30 g, 1.38 mmol, 1.0 eq.), thiophene-2-acetylchlorid (0.22 g, 1.0 eq.).

Product: Yield 235 mg (62%), UV/MS 97/93 (M$^+$ 343), r$_t$ (A, MS) 2.795. $^1$H-NMR (400 MHz, DMSO, rotamers 54/46) δ 10.8 and 10.60 (2brs, 1H), 7.4 and 7.35 (2d, 1H), 7.2–6.76 (m, 6H), 4.55 and 4.4 (2s, 2H), 4.49 and 4.26 (2dt, J=11 and 2 Hz, 2H), 4.15 and 3.79 (2s, 2H), 3.32 (d, J=11 Hz, 2H), 2.99 (q, 2H), 2.63 (s, 3H), 2.27 and 2.23 (2s, 3H), 2.09 (q, J=11 Hz, 2H), 1.66 and 1.55 (2d, J=11 Hz, 2H).

Example 75

2-(4-Methoxyphenyl)-N-(4-methylbenzyl)-N-(1-cyclopentylpiperidin-4-yl) acetamide (42ELH75)

Procedure as for 42ELH80, except that the reaction was run at 60° C. for 3 days.

Starting materials: 50ELH87 (0.25 g, 0.71 mmol, 1.0 eq.), Cyclopentylbromide (0.288 g, 3.0 eq.).

Product: Yield 91.2 mg (34%), UV/MS 88/93 (M$^+$ 421), r$_t$ (A, MS) 4.450.

Example 76

2-(4-Methoxyphenyl)-N-(4-methylbenzyl)-N-(1-(3-(1,3-dihydro-2H-benzimidazol-2-one-1-yl)propyl) piperidine-4-yl) acetamide (50ELH89).

50ELH87 (0.05 g, 0.14 mmol, 1 eq.) was transferred to a 4 ml vial and dissolved in 1 ml of acetonitrile. Then, 1-(3-chloropropyl)-1,3-dihydro-2H-benzimidazol-2-one (0.032 g, 1.1 eq.), sodium carbonate (0.022 g, 1.1 eq.) and KI (one crystal) were added and the vial was sealed and shaken for 20 h at 82° C. The mixture was extracted with distilled water (pH 10, sodium carbonate) and dichloromethane (3 times) the organic layers were dried with sodium sulfate and concentrated. The title compound was purified by HPLC and evaporated to dryness, forming a trifluoroacetic acid salt. Yield 8.8 mg (12%). UV/MS 100/100 (M$^+$ 527), r$_t$ (A, MS) 2.851.

Example 77

2-(4-Methoxyphenyl)-N-(4-methylbenzyl)-N-[1-(2-methylthiazol-4-ylmethyl) piperidin-4-yl] acetamide (63ELH1A).

50ELH87 (0.3 g, 0.852 mmol, 1.0 eq) and 4-(chloromethyl)-2-methylthiazole hydrochloride (0.235 g, 1.5 eq) were added to a 7 ml vial and dissolved in acetonitrile (3 ml). Potassium carbonate (141.3 g, 1.2 eq) and a crystal of potassium iodide were added and the vial was sealed and shaken for 20 h at 82° C. The reaction mixture was extracted with distilled water (made basic by potassium carbonate, pH 10) and dichloromethane. The crude product was dried with sodium sulfate and concentrated. After purification by HPLC the product was converted into the hydrochloride salt by dissolving the free base in 1 ml dichloromethane and adding 1 eq. HCl in ether (2M). This mixture was added drop-wise to an excess of heptane where the product precipitated. The solvent was removed by evaporation leaving a white powder as the product. yield 83.8 mg (21%), UV/MS 100/90 (M$^+$ 463), r$_t$ (B, MS) 11.82.

Example 78

2-(4-Methoxyphenyl)-N-(2-4-(fluorophenyl) ethyl)-N-(1-methylpiperidin-4-yl) acetamide (50ELH93A)

Procedure as 50ELH14B.

Reaction-Step 1: 4-[2-4-(Fluorophenyl)ethylamino]-1-methylpiperidine (50ELH92A)

Starting materials: 1-Methyl-4-piperidone (0.3 g, 2.65 mmol, 1.0 eq.), 4-(fluorophenyl)ethylamine (0.369 g, 1.0 eq.).

Product: UV/MS 60/92 (M$^+$ 237), r$_t$ (A,MS) 3.422.

Reaction-Step 2: 2-(4-Methoxyphenyl)-N-(2-4-(fluorophenyl)ethyl)-N-(1-methylpiperidin-4-yl) acetamide (50ELH93A)

Starting materials: 50ELH92A (0.625 g, 2.65 mmol, 1.0 eq.), 4-methoxyphenylacetylchloride (0.488 g, app. 1.0 eq.).

Product: Yield 181 mg (18%), UV/MS 87/97 (M$^+$ 385), r$_t$ (A, MS) 2.783. R$_f$ 0.8 (10% MeOH/CH$_2$Cl$_2$). $^1$H-NMR (400 MHz, DMSO, rotamers 50/50) δ 10.9 (brs, 1H), 7.56–6.8 (m, 8H), 4.26 and 4.02 (2brt, 2H), 3.70 and 3.95 (2s, 3H), 3.59 and 3.57 (2s, 2H), 3.4–3.15 (m, 5H), 2.96–2.66 (m, 5H), 2.62 and 2.56 (2s, 3H), 2.29 and 2.10 (2q, 2H), 1.73 and 1.41 (2d, 2H). $^{13}$C-NMR (DMSO) 172.5; 171.4; 171.3; 162.9; 162.7; 160.5; 160.3; 158.9; 158.6; 136.1; 136.1; 135.3; 131.4; 131.3; 131.1; 131.0; 131.0; 130.6; 130.5; 128.4; 128.4; 126.9; 115.9; 115.8; 115.7; 115.6; 114.5; 55.7; 53.7; 53.5; 52.7; 52.3; 50.7; 46.7; 43.8; 43.2; 43.0; 36.3; 34.7; 27.9; 26.9.

Example 79

2-(4-Methoxyphenyl)-N-[2-(2,5-dimethoxyphenyl)ethyl]-N-(1-methylpiperidin-4-yl) acetamide (50ELH93C)

Procedure as 50ELH14B. A small amount was purified by HPLC and evaporated to dryness, forming the trifluoroacetic acid salt.

Reaction-Step 1: 4-[2-(2,5-dimethoxyphenyl)ethylamino]-1-methylpiperidine (50ELH92A)

Starting materials: Methyl-4-piperidone (0.3 g, 2.65 mmol, 1.0 eq.), 2,5-(dimethoxyphenyl)ethylamine (0.481 g, 1.0 eq.).

Product: UV/MS 81/90 (M$^+$ 279), r$_t$ (A, MS) 2.868.

Reaction-Step 2: 2-(4-Methoxyphenyl)-N-[2-(2.5-dimethoxyphenyl)ethyl]-N-(1-methylpiperidin-4-yl) acetamide (50ELH93C)

Starting materials: 50ELH93C (0.737 g, 2.65 mmol, 1.0 eq.), 4-methoxyphenylacetylchloride (0.488 g, app. 1.0 eq.).

Product: UV/MS 82/100 (M$^+$ 427), r$_t$ (B, MS) 8.44. R$_f$ 0.8 (10% MeOH/CH$_2$Cl$_2$).

Example 80

2-(4-Methoxyphenyl)-N-[2-(2,4-dichlorophenyl)ethyl]-N-(1-methylpiperidin-4-yl) acetamide (50ELH93D)

Procedure as 50ELH14B, but purified by HPLC and evaporated to dryness forming the trifluoroacetic acid salt.

Reaction-Step 1: 4-[2-(2,4-Dichlorophenyl)ethylamino]-1-methylpiperidine (50ELH92D)

Starting materials: 1-Methyl-4-piperidone (0.3 g, 2.65 mmol, 1.0 eq.), 2,5-(dichlorophenyl) ethylamine (0.50 g, 1.0 eq.).

Product: UV/MS 82/92 (M$^+$ 287), r$_t$ (A, MS) 4.875.

Reaction-Step 2: 2-(4-Methoxyphenyl)-N-[2-(2,4-dichlorophenyl)ethyl]-N-(1-methylpiperidin-4-yl) acetamide (50ELH93D)

Starting materials: 50ELH93D (0.76 g, 2.65 mmol, 1.0 eq.), 4-methoxyphenylacetylchloride (0.488 g, app. 1.0 eq.).

Product: UV/MS 100/96 (M$^+$ 435), r$_t$ (A, MS) 4.415. R$_f$ 0.8 (10% MeOH/CH$_2$Cl$_2$).

Example 81

2-(4-Methoxyphenyl)-N-[2-(3-chlorophenyl)ethyl]-N-(1-methylpiperidin-4-yl) acetamide (50ELH93E)

Procedure as 50ELH14B, but purified on HPLC and evaporated to dryness forming the trifluoroacetic acid salt.

Reaction-Step 1: 4-[(3-Chlorophenyl)ethyl)amino]-1-methylpiperidine (50ELH92E)

Starting materials: 1-Methyl-4-piperidone (0.3 g, 2.65 mmol, 1.0 eq.), 3-(chlorophenyl) ethylamine (0.413 g, 1.0 eq.).

Product: UV/MS 86/88 (M$^+$ 253), r$_t$ (A,MS) 3.175.

Reaction-Step 2: 2-(4-Methoxyphenyl)-N-[2-(3-chlorophenyl)ethyl]-N-(1-methylpiperidin-4-yl) acetamide (50ELH93E)

Starting materials: 50ELH93E (0.67 g, 2.65 mmol, 1.0 eq.), 4-methoxyphenylacetylchloride (0.488 g, app. 1.0 eq.).

Product: UV/MS 100/100 (M$^+$ 401), r$_t$ (A, MS) 3.464. R$_f$ 0.8 (10% MeOH/CH$_2$Cl$_2$).

Example 82

2-(4-Methoxyphenyl)-N-[2-(4-methoxyphenyl)ethyl]-N-(1-methylpiperidin-4-yl) acetamide (50ELH95B)

Procedure as 50ELH14B. Purified by HPLC and evaporated to dryness forming the trifluoroacetic acid salt.

Reaction-Step 1: 4-[(4-Methoxyphenyl)ethyl)amino]-1-methylpiperidine (50ELH94B)

Starting materials: 1-Methyl-4-piperidone (0.3 g, 2.65 mmol, 1.0 eq.), 4-methoxyphenylethylamine (0.40 g, 1.0 eq.).

Product: UV/MS 74/87 (M$^+$ 249), r$_t$ (A,MS) 2.935.

Reaction-Step 2: 2-(4-Methoxyphenyl)-N-[2-(4-methoxyphenyl)ethyl]-N-(1-methylpiperidin-4-yl) acetamide (50ELH95B)

Starting materials: 50ELH94B (0.657 g, 2.65 mmol, 1.0 eq.), 4-methoxyphenylacetylchloride (0.488 g, app. 1.0 eq.).

Product: UV/MS 100/100 (M$^+$ 397), r$_t$ (A, MS) 2.389. R$_f$ 0.8 (10% MeOH/CH$_2$Cl$_2$).

Example 83

2-(4-Methoxyphenyl)-N-[2-(3-fluorophenyl)ethyl]-N-(1-methylpiperidin-4-yl) acetamide (50ELH95D)

Procedure as 50ELH14B. Purified on HPLC and evaporated to dryness, forming the trifluoroacetic acid salt.

Reaction-Step 1: 4-[2-((3-Fluorophenyl)ethyl)amino]-1-methylpiperidine (50ELH94D)

Starting materials: 1-Methyl-4-piperidone (0.3 g, 2.65 mmol, 1.0 eq.), 3-fluorophenylethylamine (0.369 g, 1.0 eq.).

Product: UV/MS 74/89 (M$^+$ 237), r$_t$ (A,MS) 2.946.

Reaction-Step 2: 2-(4-methoxyphenyl)-N-[2-(3-fluorophenyl)ethyl]-N-(1-methylpiperidin-4-yl) acetamide (50ELH95D)

Starting materials: 50ELH94D (0.625 g, 2.65 mmol, 1.0 eq.), 4-methoxyphenylacetylchloride (0.488 g, app. 1.0 eq.).

Product: UV/MS 100/95 (M$^+$ 385), r$_t$ (A, MS) 2.946. R$_f$ 0.8 (10% MeOH/CH$_2$Cl$_2$).

Example 84

2-(4-ethoxyphenyl)-N-[2-(4-fluorophenyl)ethyl]-N-(1-methylpiperidin-4-yl) acetamide (63ELH20)

Reaction Step, 1: 4-Ethoxyphenylacetic acid chloride (63ELH19)

4-Ethoxyphenylacetic acid (0.5 g, 2.8 mmol) was transferred to a 7 ml vial and dissolved in thionylchloride (3 ml). The reaction mixture was shaken at 70° C. for 2½ hours.

Thionylchloride was evaporated off and the resulting product was used unpurified.

Reaction Step 2: 2-(4-Ethoxyphenyl)-N-[2-(4-fluorophenyl)ethyl]-N-(1-methylpiperidin-4-yl) acetamide (63ELH20)

63ELH17 (0.11 g, 0.47 mmol) was transferred to a 4 ml vial and dissolved in dichloromethane. 63ELH19 (0.084 mg, 1 eq.) was added and the vial was sealed and the reaction shaken for 20 h. The product was extracted in distilled water (made basic with potassium carbonate, pH 10) and dichloromethane. Dried with sodium sulfate and concentrated. Purified by HPLC. The extraction, drying and concentration was repeated and the product re-dissolved in dichloromethane (1 ml) and HCl (1 eq., 2 M in ether) was added. The mixture was added drop-wise to an excess of heptane whereupon the salt precipitated. Yield 33.4 mg (18%), UV/MS: 92/100 ($M^+$ 399), $t_r$ (B, MS) 10.38.

Example 85

2-(4-Ethoxyphenyl)-N-(4-fluorobenzyl)-N-(1-methylpiperidin-4-yl) acetamide (63ELH21)

50ELH4 (0.11 g, 0.49 mmol, 1.0 eq.) was transferred to a 4 ml vial and dissolved in dichloromethane. 63ELH19 (0.089 mg, 1.0 eq.) was added and the vial was sealed and the reaction shaken for 20 h. The product was extracted in distilled water (made basic with potassium carbonate, pH 10) and dichloromethane. Dried with sodium sulfate and concentrated. Purified by HPLC. The extraction, drying and concentration was repeated and the product dissolved in dichloromethane (1 ml) and HCl (1 eq., 2 M in ether)is added. This mixture was added drop-wise to an excess of heptane whereupon the salt precipitated. Yield 31.1 mg (16%), UV/MS: 94/100 ($M^+$ 385), $t_r$ (A, MS) 2.573.

Example 86

N-((4-methylphenyl)methyl)-N-(1-methylpiperidin-4-yl)-2-(3-hydroxy-4-methoxyphenyl)acetamide (57MBT12B)

N-((4-methylphenyl)methyl)-4-amino-1-methylpiperidine (50ELH25) (105 mg, 0.48 mmol) and 3-hydroxy-4-methoxyphenylacetic acid (88 mg, 0.48 mmol) were dissolved in DMF (10 ml). Diisopropylethylamine (DIEA, 250 µL, 1.44 mmol) was added followed by bromo-tris-pyrrolidino-phosphonium hexafluorophosphate (PyBrOP, 336 mg, 0.72 mmol), and the mixture was stirred at r.t for 1 h. Water (50 mL) was added, and the reaction mixture was extracted with EtOAc (2×50 mL). Drying by $Na_2SO_4$ and concentration yielded 514 mg crude material, which was purified by flash chromatography (0–30% MeOH in $CH_2Cl_2$). This gave 105 mg (57%)of the title compound as a white solid. $R_f$=0.20 (10% MeOH in $CH_2Cl_2$). HPLC-MS (method A)showed $MH^+$=383. UV/MS(%)=100/92. $^1$H-NMR (400 MHz, $CD_3OD$, Rotamers 52:48): δ 7.18–6.58 (m, 7H), 4.53 (s, 2H), 4.31 and 3.97 (2m, 1H), 3.82 and 3.81 (2s, 3H), 3.80 and 3.55 (2s, 2H), 3.04 and 2.85 (2m, 2H), 2.41 and 2.32 (2s, 3H), 2.35 and 2.12 (2m, 2H), 2.29 and 2.27 (2s, 3H), 1.83 and 1.74 (2m, 2H), 1.72 and 1.33 (2m, 2H)

Example 87

N-((4-methylphenyl)methyl)-N-(1-methylpiperidin-4-yl)-2-(3,4-dihydroxyphenyl)acetamide (57MBT24B)

N-((4-methylphenyl)methyl)-N-(1-methylpiperidine-4-yl)-2-(3-hydroxy-4-methoxyphenyl)acetamide (57MBT12B) (52 mg, 0.136 mmol) was dissolved in $CH_2Cl_2$ (1 mL) and cooled to −78 ° C. Boron tribromide (1M in $CH_2Cl_2$, 204 µl, 0.204 mmol) was added dropwise and the cooling bath was removed. After stirring for 2 h, methanol (2 mL) was added and the mixture was evaporated. The resulting oil was purified by preparative HPLC to give 24 mg (48%) of the title compound as a white solid. HPLC-MS (method A) showed $MH^+$=369. UV/MS(%)= 100/97. 1H-NMR (400 MHz, CD3OD, Rotamers 33:67): δ 7.19–6.47 (m, 7H), 4.54 and 4.53 (2s, 2H), 4.23 (m, 1H), 3.83 and 3.58 (2s, 2H), 3.46 and 3.40 (2br d, J=12 Hz, 2H), 3.02 and 2.95 (2br t, J=12 Hz, 2H), 2.79 (s, 3H), 2.33 and 2.28 (2s, 3H), 2.17 and 1.84 (2dq, J=4, 12 Hz, 2H), 1.87 and 1.48 (2br d, J=12 Hz, 2H)

Example 88

N-((3-hydroxy-4-methylphenyl)methyl)-N-(1-methylpiperidin-4-yl)-2-(4-methoxyphenyl) acetamide (57MBT54B)

N-((4-methoxyphenyl)methyl)-4-amino-1-methylpiperidine (1 g, 4.27 mmol) was dissolved in 4% formic acid in methanol (60 mL). 10% Pd/C (1 g) was added under argon and the reaction mixture was heated to reflux for 24 h. The mixture was filtered through celite and the filtrate was acidified with conc. HCl to pH 1. Concentration yielded a yellow oil which was purified by flash chromatography ($MeOH/CH_2Cl_2$ 3:7+3.5% $NH_4OH$)to give 249 mg (51%) of 4-amino-1-methylpiperidine (57-MBT36B) as a white solid. $R_f$0.13 (10% MeOH in $CH_2Cl_2$+3.5% NH4OH). HPLC-MS (method B) showed $MH^+$=115. UV/MS(%)=−/ 100.

4-Amino-1-methylpiperidine (57MBT36B) (26 mg, 0.231 mmol) was dissolved in methanol (1 mL) and 3-hydroxy-4-methylbenzaldehyde (32 mg, 0.231 mmol) and acetic acid (33 µL) were added. The mixture was cooled to 0° C. $NaBH_3CN$ (29 mg, 0.462 mmol) was added and the cooling bath was removed. After 3 h the reaction mixture was evaporated and flash chromatography (0–30% MeOH in $CH_2Cl_2$) gave 27 mg (50%) of N-((3-hydroxy-4-methylphenyl)methyl)-4-amino-1-methylpiperidine (57MBT44C) as a white solid. $R_f$=0.27 (10% MeOH in $CH_2Cl_2$+3.5% $NH_4OH$). HPLC-MS (method A) showed $MH^+$=235. UV/MS(%)=99/99.

N-((3-hydroxy-4-methylphenyl)methyl)-4-amino-1-methylpiperidine (57MBT44C) (27 mg, 0.115 mmol) was dissolved in $CH_2Cl_2$ (2 mL). 4-Methoxyphenylacetyl chloride (17 µL, 0.115 mmol) was added dropwise under argon. After 3 h, n-heptane (3 mL) was added and the mixture was evaporated. Flash chromatography (0–20% MeOH in $CH_2Cl_2$) gave 14 mg (32%) of the title compound as a white solid. $R_f$=0.32 (10% MeOH in $CH_2Cl_2$+3.5% $NH_4OH$). HPLC-MS (method A) showed $MH^{+-}$383. UV/MS(%)=99/ 96. $^1$H-NMR (400 MHz, $CD_3OD$, Rotamers 63:37): δ 7.28–6.55 (m, 7H), 4.48 (s, 2H), 4.37 and 3.95 (2m, 1H), 3.78 and 3.77 (2s, 3H), 3.06 and 2.89 (2br d, J=12 Hz, 2H), 2.42 and 2.32 (2s, 3H), 2.40 and 2.12 (2m, 2H), 2.18 and 2.12 (2s, 3H), 1.86 and 1.83 (2m, 2H), 1.75 and 1.35 (2br d, J=12 Hz, 2H)

Example 89

N-((4-methylphenyl)methyl)-N-(1-methylpiperidin-4-yl)-2-(4-bromophenyl)acetamide hydrochloride (57MBT70-1D)

4-Bromophenylacetic acid (54 mg, 0.252 mmol) was dissolved in $CH_2Cl_2$ (2 mL), and N-((4-methylphenyl)

methyl)-4-amino-1-methylpiperidine (292 mg/mL stock solution in $CH_2Cl_2$, 171 µL, 0.229 mmol) and polystyrene supported diisopropylethylamine (PS-DIEA with a loading of 3.57 mmol/g, 192 mg, 0.687 mmol) was added followed by bromo-tris-pyrrolidino-phosphonium hexafluorophosphate (PyBrOP, 160 mg/mL stock solution, 1 mL, 0.334 mmol). The reaction mixture was shaken for 1 h at r.t. and filtered onto a prewashed (methanol) ion exchange column (0.88 mmol/g, 1 g). The column was washed with methanol (8*4 mL) and the remaining product was eluted off the column with 10% $NH_4OH$ in methanol (2*4 mL) and evaporated. The resulting oil was filtered through silica (H=4 cm, D=1 cm)with methanol/$CH_2Cl_2$ 1:9 (20 mL), evaporated and subjected to a second ion exchange column (0.88 mmol/g, 1 g). The column was washed with methanol (8*4 mL) and the remaining product was eluted off the column with 10% $NH_4OH$ in methanol (2*4 mL) and evaporated on rotavap and oil pump. The product was dissolved in $CH_2Cl_2$ (0.5 mL) and HCl in diethylether (1.0 M, 0.1 mL, 0.1 mmol) was added. The solution was added to n-heptane (3 mL) and evaporation afforded 29 mg (25%) of the title compound as a white solid. $R_f$=0.31 (10% MeOH in $CH_2Cl_2$). HPLC-MS (method B) showed $MH^+$=416. UV/MS(%)=100/99.

Example 90

N-((4-methylphenyl)methyl)-N-(1-methylpiperidin-4-yl)-2-(4-iodophenyl)acetamide hydrochloride (57MBT70-2D)

The title compound was prepared according to example MBT04. Yield: 33 mg (26%). $R_f$=0.31 (10% MeOH in $CH_2Cl_2$). HPLC-MS (method B)showed $MH^+$=463. UV/MS (%)=100/98.

Example 91

N-((4-methylphenyl)methyl)-N-(1-methylpiperidin-4-yl)-2-(4-(2-propyl)phenyl)acetamide hydrochloride (57MBT70-3D)

The title compound was prepared according to example MBT04. Yield: 36 mg (34%). $R_f$=0.31 (10% MeOH in $CH_2Cl_2$). HPLC-MS (method B) showed $MH^+$=379. UV/MS(%)=100/97.

Example 92

N-((4-methylphenyl)methyl)-N-(1-methylpiperidin-4-yl)-2-(4-trifluoromethoxyphenyl)acetamide hydrochloride(57MBT70-4D)

The title compound was prepared according to example MBT04. Yield: 35 mg (30%). $R_f$=0.27 (10% MeOH in $CH_2Cl_2$). HPLC-MS (method B)showed $MH^+$=421. UV/MS (%)=100/99.

Example 93

N-((4-methylphenyl)methyl)-N-(1-methylpiperidin-4-yl)-2-(4-methylthiophenyl)acetamide hydrochloride(57MBT70-5D)

The title compound was prepared according to example MBT04. Yield: 35 mg (33%). $R_f$ =0.30 (10% MeOH in $CH_2Cl_2$). HPLC-MS (method B) showed $MH^+$=383. UV/MS(%)=100/99.

Example 94

N-((4-methylphenyl)methyl)-N-(1-methylpiperidin-4-yl)-2-(4-(N,N-dimethylamino)phenyl)acetamide hydrochloride(57MBT70-6D)

The title compound was prepared according to example MBT04.

Yield: 16 mg (15%). $R_f$=0.25 (10% MeOH in $CH_2Cl_2$). HPLC-MS (method A) showed $MH^+$=380. UV/MS(%)=100/100.

Example 95

N-((4-methylphenyl)methyl)-N-(1-methylpiperidin-4-yl)-2-(4-nitrophenyl)acetamide hydrochloride (57MBT70-7D)

The title compound was prepared according to example MBT04. Yield: 28 mg (27%). $R_f$=0.27 (10% MeOH in $CH_2Cl_2$). HPLC-MS (method B) showed $MH^+$=382. UV/MS(%)=100/100.

Example 96

N-((4-methylphenyl)methyl)-N-(1-methylpiperidin-4-yl)-2-(4-methoxy-3-methylphenyl)acetamide hydrochloride(57MBT70-8D)

The title compound was prepared according to example MBT04. Yield: 34 mg (32%). $R_f$=0.30 (10% MeOH in $CH_2Cl_2$). HPLC-MS (method B) showed $MH^{+=381}$. UV/MS (%)=100/99.

Example 97

N-((4-methylphenyl)methyl)-N-(1-methylpiperidin-4-yl)-2-(4-pyridyl)acetamide hydrochloride (57MBT70-9F)

The title compound was prepared according to example MBT04. Yield: 18 mg (17%). $R_f$=0.09 (10% MeOH in $CH_2Cl_2$). HPLC-MS (method A) showed $MH^+$=338. UV/MS(%)=100/100.

Example 98

N-((4-methylphenyl)methyl)-N-(1-methylpiperidin-4-yl)-2-(4-methylphenyl)acetamide hydrochloride (57MBT62B)

The title compound was prepared according to example MBT04. Yield: 10 mg (35%). $R_f$=(10% MeOH in $CH_2Cl_2$). HPLC-MS (method A) showed $MH^+$=351. UV/MS(%)=100/100.

Example 99

N-((4-(hydroxymethyl)phenyl)methyl)-N-(1-methylpiperidin-4-yl)-2-(4-methoxyphenyl) acetamide hydrochloride(57MBT72D)

To a stirred suspension of $LiAlH_4$ (285 mg, 7.52 mmol) in diethylether (10 mL)at 0° C. was added a solution of 4-cyanobenzyl alcohol (0.5 g, 3.76 mmol) in diethylether (5 mL) over 15 min. The grey reaction mixture was heated to reflux for 3 h. After cooling to r.t., the mixture was treated successively with water (1 mL), 2M NaOH (2 mL) and water (2 mL) under vigorous stirring. The resulting white slurry was filtered and washed with $CH_2Cl_2$ (20 mL). Extraction with additional $CH_2Cl_2$ (20 mL) and n-butanol (20 mL) and evaporation yielded an oil, which upon flash chromatography (0–15% MeOH in $CH_2Cl_2$) gave 152 mg (29%)of 4-(aminomethyl)benzylalcohol (57MBT52B) as a white solid. $R_f$=0.51 (30% MeOH in $CH_2Cl_2$+3.5% $NH_4OH$).

1-Methyl-4-piperidone (84 µL, 0.73 mmol) was dissolved in methanol (5 mL) and 4-(aminomethyl)benzylalcohol (57MBT52B) (100 mg, 0.73 mmol) was added followed by acetic acid (125 μL). NaBH$_3$CN (92 mg, 1.46 mmol) was added and the mixture was stirred for 3 h. The reaction mixture was evaporated and 2M NaOH (5 mL) was added. Extraction with CH$_2$Cl$_2$ (4*5 mL), drying with Na$_2$SO$_4$ and evaporation gave 152 mg (87%) of N-((4-(hydroxymethyl)phenyl)methyl)-4-amino-1-methylpiperidine (57MBT56D) as a white solid. HPLC-MS (method B) showed MH$^+$=235. UV/MS(%)=100/100.

N-((4-(Hydroxymethyl)phenyl)methyl)-4-amino-1-methylpiperidine (57MBT56D) (20 mg, 0.0853 mmol) was dissolved in CH$_2$Cl$_2$ (2 mL) and 4-methoxyphenylacetyl chloride (26 μL, 0.171 mmol) was added dropwise. The reaction mixture was stirred for 1 h and water (500 μL) was added followed by evaporation. A solution of sodium (5 mg, 0.179 mmol) in methanol (2 mL) was added. After stirring for 4 h, the solution was transferred to a prewashed (methanol) ion exchange column (0.88 mmol/g, 1 g) and washed with methanol (4*4 mL). The remaining product was eluted off the column with 10% NH$_4$OH in methanol (2*4 mL) and evaporated. The resulting oil was filtered through silica (H=4 cm, D=1 cm) with methanol/CH$_2$Cl$_2$ 2:8 (20 mL), evaporated and subjected to a second ion exchange column (0.88 mmol/g, 1 g). The column was washed with methanol (8*4 mL) and the remaining product was eluted off the column with 10% NH$_4$OH in methanol (2*4 mL) and evaporated on rotavap and oilpump. The product was dissolved in CH$_2$Cl$_2$ (0.5 mL) and HCl in diethylether (1.0 M, 0.1 mL, 0.1 mmol) was added. The solution was added to n-heptane (3 mL) and evaporation afforded 14 mg (39%) of the title compound as a white solid. R$_f$=0.16 (10% MeOH in CH$_2$Cl$_2$). HPLC-MS (method B) showed MH$^+$=383. UV/MS(%)=100/96.

Example 100

2-(4-Chlorophenyl)-N-(4-methylbenzyl)-N-(1-isopropylpiperidin-4-yl)acetamide (47AKU-7)

1-Trifluoroacetyl-4-piperidone (47AKU-2)

4-Piperidone hydrochloride monohydrate (3.85 g, 25 mmol) and Triethylamine (10.5 ml, 75 mmol) were partly dissolved in 100 ml of dichloromethane and stirred for 10 min. Reaction mixture was then cooled on ice-bath and trifluoroacetic anhydride (7.2 ml, 50 mmol) was slowly added over 10 min. Ice-bath was removed and mixture was stirred overnight. Additional trifluoroacetic anhydride (2 ml) was added and the mixture was stirred for 1 hr. Water (200 ml) was added. Phases were separated and aq. phase was re-extracted with dichloromethane. Combined organic phases were washed with brine, dried over MgSO$_4$ and concentrated (40° C.) giving 4.97 g (100%) 47AKU-2 as yellow crystals. TLC (5% methanol in dichloromethane): R$_f$=0.8. $^1$H-NMR (400 MHz, CDCl$_3$): δ=3.87–3.99 (4H, m); 2.54–2.61 (4H, m). $^{13}$C-NMR (CDCl$_3$): δ=204.7, 118.0, 115.1, 44.2, 42.8, 41.2, 40.5.

4-(4-Methylbenzylamino)-1-trifluoroacetyl-piperidine (47AKU-3)

47AKU-2 (4.97 g, 25 mmol) was dissolved in 100 ml methanol and 4-methylbenzyl-amine (3.2 ml, 25 mmol) was added. Mixture was stirred and acetic acid (~2 ml) was added until pH~5. NaCNBH$_3$ (3.15 g, 50 mmol) was slowly added. After magnetic stirring for 20 hrs the methanol was partly removed on the rotary evaporator (40° C.). Dichloromethane, 2M NaOH and water were added until pH~10. Phases were separated and aq. phase was then re-extracted twice with dichloromethane. Combined organic phases were washed with brine and dried over MgSO$_4$. Concentration(40° C.) yielded 6.94 g (92%) 47AKU-3. TLC (10% methanol in dichloromethane): R$_f$=0.6. HPLC-MS (Method A): M$^+$=301.0 (UV/MS(%)=94/100).

2-(4-Chlorophenyl)-N-(4-methylbenzyl)-N-(1-trifluoroacetylpiperidin-4-yl)acetamide (47AKU-4)

47AKU-3 (3.01 g, 10 mmol) in 25 ml of dichloromethane was placed in a 100 ml flask. Triethylamine (1.4 ml, 10 mmol) was added and the mixture was cooled on an ice-bath and stirred for 10 min. 4-Chlorophenylacetyl chloride (1.90 g, 10 mmol) was dissolved in 10 ml dichloromethane and added slowly to the ice-cold mixture. After 15 min. the ice-bath was removed and the mixture was left for 1 hr. Precipitation was observed. The reaction mixture was then concentrated at aspirator pressure(40° C.). The crude product was purified by flash chromatography (0–50% ethylacetate in heptane) yielding 2.38 g (53%/) 47AKU-4. TLC (100% dichloromethane): R$_f$=0.6. HPLC-MS (Method A): M$^+$=453.0 (UV/MS(%)=89/84).

2-(4-Chlorophenyl)-N-(4-methylbenzyt)-N-(piperidin-4-yl)acetamide (47AKU-6)

47AKU-4 (2.38 g; ~5 mmol) was dissolved in 50 ml of methanol. K$_2$CO$_3$ (3.5 g; 25 mmol) was added in one portion. After magnetic stirring for 20 hrs, additional K$_2$CO$_3$ (1 g) was added. After 4 hrs magnetic stirring methanol was partly removed by evaporation(40° C.). Ethyl acetate (100 ml) and water (100 ml) were added. The phases were separated and the aq. phase was then re-extracted with ethylacetate. The combined organic phases were dried over MgSO$_4$ and concentrated (40° C.) giving 1.95 g (100%) 47AKU-6. TLC (20% methanol in dichloromethane): R$_f$=0.3. HPLC-MS (Method A): M$^+$=357.1 (UV/MS(%)=84/95).

2-(4-Chlorophenyl)-N-(4-methylbenzyl)-N-(1-isopropylpiperidin-4-yl)-acetamide (47AKU-7)

47AKU-6 (358 mg, 1.0 mmol) was dissolved in 20 ml of acetonitrile. Triethylamine (1.4 ml, 10 mmol) was added and mixture was stirred for 10 min. Isopropyl bromide (370 mg, 3.0 mmol) was dissolved in 5 ml of acetonitrile and added to the reaction mixture which was stirred at room temp. for 20 hrs and then heated to 60° C. for 4 hrs. After cooling, ethylacetate (25 ml) and water (25 ml) were added. The phases were separated and the aq. phase was then re-extracted with ethylacetate. The combined organic phases were washed with brine, dried over MgSO$_4$ and concentrated (40° C.) giving 362 mg of crude product. Purification by flash chromatography (0–10% methanol in dichloromethane) and HCl-precipitation from 2M HCl/diethyl ether in dichloromethane/heptane gave 76 mg (18%) 47AKU-7. TLC (10% methanol in dichloromethane): R$_f$=0.4. Mp=223–224° C. HPLC-MS (Method A): M$^+$=399.1 (UV/MS(%)=100/99). $^1$H-NMR (400 MHz, CDCl$_3$): δ=7.03–7.29 (8H, m); 4.86 (1H, m); 4.61 (2H, m); 3.58 (2H, m); 3.37 (3H, m); 2.82 (2H, m); 2.64 (2H, m); 2.34 (3H, s); 1.80 (2H, m); 1.39 (6H, d). $^{13}$C-NMR (CDCl$_3$): δ=172.4 137.4, 134.8, 133.3, 133.1, 130.4, 129.9, 129.0, 125.8, 58.0, 49.5, 48.2, 46.6, 40.4, 26.0, 21.2, 17.0.

Example 101

2-(4-Chlorophenyl)-N-(4-methylbenzyl)-N-(1-ethylpiperidin-4-yl)acetamide (47AKU-12)

47AKU-6 (358 mg, 1.0 mmol) was dissolved in 20 ml of acetonitrile. Triethylamine (1.4 ml, 10 mmol) was added and the mixture was stirred for 10 min. Ethyl bromide (370 μl, 5.0 mmol) was added. The mixture was then heated to 50°

C. and stirred overnight. After cooling, water (25 ml) and ethylacetate (25 ml) were added. The phases were separated and the aq. phase was re-extracted with ethylacetate. The combined organic phases were washed with brine and dried over MgSO$_4$. Evaporation(40° C.) yielded 406 mg of crude product. Purification by ion exchange chromatography (washout with 10% aq. NH$_4$OH (25%) in methanol) gave 166 mg (43%) 47AKU-12. The HCl-salt was prepared from 2M HCl/diethylether in dichloromethane/heptane. TLC (10% methanol in dichloromethane): R$_f$=0.5. HPLC-MS (Method A): M$^+$=385.1 (UV/MS(%)=100/99). $^1$H-NMR (400 MHz, CDCl$_3$, rotamers): δ=7.02–7.34 (8H, m); 4.62 (1H, m); 4.46 and 4.53 (2H, 2s); 3.81 (1H, s); 3.55 (2H, s); 2.92 (2H, m); 2.34 (3H, s); 2.29 (1H, s); 1.98 (2H, m); 1.52–1.84 (4H, m); 1.03 (3H, t). $^{13}$C-NMR (CDCl$_3$): δ=171.7, 137.2, 135.4, 133.9, 132.8, 130.4, 129.7, 128.9, 125.8, 52.8, 52.4, 46.5, 40.8, 31.2, 29.8, 21.2, 12.4.

Example 102

2-Phenyl-N-(4-methylbenzyl)-N-(1-methylpiperidin-4-yl)-acetamide (47AKU-13)

47AKU-5 (218 mg, 1.0 mmol) was dissolved in 2 ml of dichloromethane in a 50 ml flask. Phenylacetyl chloride (134 μl, 1.0 mmol) was added. After 3 hrs stirring at room temp. mixture was concentrated on Rotavapor (40° C.). Crude product was purified by ion exchange chromatography (washout with 10% aq. NH$_4$OH (25%) in methanol) and flash chromatography (0–10% methanol in dichloromethane) giving 48 mg (14%) 47AKU-13. HCl-salt was prepared from 2M HCl/diethylether in dichloromethane/heptane. TLC (10% methanol in dichloromethane): R$_f$=0.4. HPLC-MS (Method A): M$^+$=337.1 (UV/MS(%)=98/98). $^1$H-NMR (400 MHz, CDCl$_3$, rotamers): δ=7.01–7.40 (9H, m); 4.63 (1H, m); 4.53 and 4.45 (2H, 2s); 3.85 and 3.61 (2H, 2s); 2.86 and 2.77 (2H, 2m); 2.35 and 2.29 (3H, 2s); 2.25 and 2.20 (3H, 2s); 209 (2H, m); 1.61–1.86 (4H, m). $^{13}$C-NMR (CDCl$_3$): δ=72.2, 137.1, 135.5, 129.7, 128.9, 128.8, 127.2, 126.9, 125.8, 55.3, 51.6, 46.6, 46.1, 41.6, 29.5, 21.2.

Example 103

2-(4-Chlorophenyl)-N-(4-methylbenzyl)-N-(1-methylpiperidin-4-yl)-acetamide (47AKU-8)
4-(4-Methylbenzylamino)-1-methyl-piperidine (47AKU-5)

1-Methyl-4-piperidone (1.13 g, 10 mmol) was dissolved in 20 ml of methanol and added to a 100 ml flask. 4-Methylbenzylamine (1.21 g, 10 mmol) in 10 ml of methanol was added. Acetic acid (~1.5 ml) was added until pH~5. NaCNBH$_3$ (1.26 g, 20 mmol) was slowly added. After 20 hrs magnetic stirring methanol was partly removed on Rotavapor (40° C.). Dichloromethane, water and 2M NaOH were added until pH~10. The phases were separated and aq. phase was extracted twice with dichloromethane. The combined organic phases were washed with brine and dried over MgSO$_4$. Concentration on Rotavapor (40° C.) yielded 2.06 g crude (93%) 47AKU-5. TLC (20% methanol in dichloromethane): R$_f$=0.3. HPLC-MS (Method A): M$^+$=219.1 (UV/MS(%)=89/98).
2-(4-Chlorophenyl)-N-(4-methylbenzyl)-N-(1-methylpiperidin-4-yl)-acetamide (47AKU-8)

47AKU-5 (437 mg, 2.0 mmol) was dissolved in 10 ml of dichloromethane in a 50 ml flask. Triethylamine (280 μl, 2.0 mmol) was added and the mixture was cooled to 0° C. on an ice bath and stirred for 10 min. 4-Chlorophenylacetyl chloride (380 mg, 2.0 mmol) was dissolved in 10 ml of dichloromethane and added to the cooled mixture. After 2 hrs stirring at room temp. additional dichloromethane (10 ml) and water (20 ml) were added. The phases were separated and the aq. phase was re-extracted with dichloromethane. The combined organic phases were dried over MgSO$_4$ and concentrated on the Rotavapor (40° C.) giving 755 mg of crude product. Purification by flash chromatography (0–10% methanol in dichloromethane)gave 485 mg (65%) product. Further purification by ion exchange chromatography (washout with 10% aq. NH$_4$OH (25%) in methanol) gave 239 mg (32%) 47AKU-8. The HCl-salt was prepared from 2M HCl/diethylether in dichloromethane/heptane. TLC (10% methanol in dichloromethane): R$_f$=0.4. Mp=217–219° C. HPLC-MS (Method A): M$^+$=371.1 (UV/MS(%)=99/99). $^1$H-NMR (400 MHz, CD$_3$OD): δ=7.05–7.39 (8H, m); 4.80 (3H, s); 4.62+4.56 (2H, 2s); 4.35 (1H, m); 4.00 (1H, s); 3.71 (1H, s); 3.46 (2H, m); 3.06 (2H, m); 2.80 (3H, s); 2.32+2.27 (3H, 2s); 2.19 (1H,m). $^{13}$C-NMR (CD$_3$OD): δ=173.0, 137.5, 134.5, 133.9, 132.6, 130.6, 129.5, 128.5, 126.2, 54.0, 51.4, 42.6, 40.2, 31.8, 26.6, 19.9.

Example 104

2-(4-Chlorophenyl)-N-(4-methylbenzyl)-N-(1-cyclopentylpiperidin-4-yl)-acetamide (47AKU-11)

47AKU-6 (358 mg, 1.0 mmol) was dissolved in 20 ml of acetonitrile. Triethylamine (1.4 ml, 10 mmol) was added and mixture was stirred for 10 min. Cyclopentylbromide (540 μl, 5.0 mmol) was added and the mixture was stirred at room temp. After 20 hrs the mixture was heated to 50° C. for an additional 24 hrs. The reaction mixture was then cooled and water (25 ml) and ethylacetate (25 ml) were added. The phases were separated and the aq. phase was re-extracted with ethylacetate. The combined organic phases were washed with brine and dried over MgSO$_4$. Concentration on Rotavapor (45° C.) yielded 426 mg of crude product. Purification by ion exchange chromatography (washout with 10% aq. NH$_4$OH (25%) in methanol) and flash chromatography (0–10% methanol in dichloromethane)gave 76 mg (18%) 47AKU-11. The HCl-salt was prepared from 2M HCl/diethylether in dichloromethane/heptane. TLC (10% methanol in dichloromethane): R$_f$=0.5. HPLC-MS (Method A): M$^+$=425.1 (UV/MS(%)=100/97). $^1$H-NMR (400 MHz, CDCl$_3$, rotamers): δ=7.01–7.34 (8H, m); 4.67 (1H, m); 4.49 and 4.52 (2H, 2s); 3.54 (2H, s); 3.15 and 3.02 (2H, 2m); 2.64 (1H, m); 2.27 and 2.34 (3H, 2s); 2.20 (1H, m); 1.85 (4H, m); 1.69 (4H, m); 1.53 (4H, m); 1.37 (1H, m). $^{13}$C-NMR (CDCl$_3$): δ=171.9, 137.2, 135.2, 133.8, 132.9, 130.4, 129.7, 128.9, 125.8, 67.7, 52.4, 52.1, 46.5, 40.7, 30.2, 28.8, 24.3, 21.2.

Example 105

2-(4-Flourophenyl)-N-(4-methylbenzyl)-N-(1-methylpiperidin-4-yl)-acetamide (47AKU-14)

47AKU-5 (218 mg, 1.0 mmol) was dissolved in 3 ml of dichloromethane in a 50 ml flask. 4-Fluorophenylacetyl chloride (150 μl, 1.1 mmol) was added. After 4 hrs stirring at room temp. the mixture was concentrated on Rotavapor (40° C.). The crude product was purified by flash chromatography (0–10% methanol in dichloromethane) giving 243 mg (68%) 47AKU-14. The HCl-salt was prepared from 2M HCl/diethylether in dichloromethane/heptane. TLC (10% methanol in dichloromethane): R$_f$=0.5. HPLC-MS (Method A): M$^+$=355.1 (UV/MS(%)=100/100). $^1$H-NMR (400 MHz, CDCl$_3$): δ=6.92–7.33 (8H, m); 4.73 (1H, m); 4.52 (2H, s); 3.56 (2H, 2s); 3.44 (5H, m); 3.25 (2H, m); 2.52–2.67 (4H, m); 2.33 (3H, s). $^{13}$C-NMR (CDCl$_3$): δ=172.5, 163.3, 160.9, 139.5, 134.8, 130.6, 129.8, 125.8, 115.8, 54.6, 50.8, 49.9, 46.7, 40.4, 27.2, 21.2.

Example 106

2-(4-Chlorophenyl)-N-(4-methylbenzyl)-N-(1-2-hydroxyethyl)-piperidin-4-yl)-acetamide (47AKU-18)

47AKU-6-2 (358 mg, 1.0 mmol) was dissolved in 10 ml of acetonitrile in 50 ml flask. Triethylamine (1.4 ml, 10 mmol) was added and mixture was stirred for 10 min.

2-Bromoethanol (215 μl, 3.0 mmol) was added. Reaction mixture was then heated to 60° C. and stirred overnight. After cooling ethylacetate (25 ml) and water (25 ml) were added. Phases were separated and aq. phase was re-extracted with ethylacetate. Combined organic phases were washed with brine, dried over MgSO$_4$ and concentrated on Rotavapor (40° C.) giving 406 mg crude product. Purification by flash chromatography (0–10% methanol in dichloromethane) afforded 253 mg (63%) 47AKU-18. HCl-salt was prepared from 2M HCl/diethylether in dichloromethane/heptane. TLC (10% methanol in dichloromethane): $R_f$=0.4. HPLC-MS (Method A): M$^+$=401.1 (UV/MS(%)=100/100). $^1$H-NMR (400 MHz, CDCl$_3$, rotamers): δ=7.04–7.34 (8H, m); 4.60 (1H, m); 4.52 and 4.45 (2H, 2s); 3.55 (4H, m); 3.03 (1H, bs); 2.92 (2H, m); 2.52 (2H, m); 2.36 and 2.31 (3H, 2s); 2.19 (2H, m); 1.66 (4H, m). ). $^{13}$C-NMR (CDCl$_3$): δ=171.7, 137.3, 135.2, 133.8, 132.9, 130.4, 129.8, 128.9, 125.8, 59.4, 58.1, 53.1, 52.3, 46.8, 40.8, 29.7, 21.2.

Example 107

2-(4-Chlorophenyl)-N-(4-methylbenzyl)-N-(1-cyclobutylpiperidin-4-yl)-acetamide (47AKU-19)
1-Cyclobutyl-4-piperidone (47AKU-15)

Partly dissolved quartenary salt (1.23 g, 3.7 mmol) (prepared according to the procedure outlined in the synthesis of 47AKU-47) was slowly added to a refluxing solution of Cyclobutylamine (178 mg, 2.5 mmol) and Potassium carbonate (48 mg, 0.34 mmol) in ethanol. The mixture was refluxed for 1.5 hrs. After cooling to room temp. water (10 ml) and dichloromethane (25 ml) were added. Phases were separated and aq. phase was re-extracted with dichloromethane. Combined organic phases were dried over MgSO$_4$ and concentrated on Rotavapor (40° C.) giving 419 mg crude 47AKU-15. TLC (10% methanol in dichloromethane): $R_f$=0.4. HPLC-MS (Method A): M$^+$=154.1 (MS(%)=75).
4-(4-Methylbenzylamino)-1-cyclobutyl-piperidine (47AKU-16)

4-Methylbenzylamine (215 mg, 1.8 mmol) was dissolved in 5 ml methanol and placed in 50 ml flask. 47AKU-15 (270 mg, 1.8 mmol) in 5 ml methanol was added. Acetic acid (0.3 ml) was added until pH~5. NaCNBH$_3$ (226 mg, 3.6 mmol) was slowly added. Gas evolution observed. After 24 hrs magnetic stirring dichloromethane, 2M NaOH and water were added until pH~10. Phases were separated and aq. phase was then re-extracted with dichloromethane. Combined organic phases were dried over MgSO$_4$ and concentrated on Rotavapor (40° C.) yielding 419 mg crude 47AKU-16. TLC (10% methanol in dichloromethane): $R_f$=0.3. HPLC-MS (Method A): M$^+$=259.1 (UV/MS(%)=44/87).
2-(4-Chlorophenyl)-N-(4-methylbenzyl)-N-(1-cyclobutylpiperidin-4-yl)-acetamide (47AKU-19)

47AKU-16 (209 mg, 0.8 mmol) was placed in 50 ml flask and 5 ml dichloromethane was added. 4-Chlorophenylacetyl chloride (171 mg, 0.9 mmol) in 5 ml dichloromethane was added. After 5 hrs magnetic stirring the reaction mixture was concentrated on Rotavapor (40° C.). Crude product was purified by flash chromatography (0–10% methanol in dichloromethane) giving 101 mg (31%) product. Further purification by ion exchange chromatography (washout with 10% aq. NH$_4$OH (25%) in methanol) gave 55 mg (17%) 47AKU-19. Oxalate-salt was prepared from Oxalic acid (1.1 eq) in dichloromethane/heptane. TLC (10% methanol in dichloromethane): $R_f$=0.6. HPLC-MS (Method B): M$^+$=411.2 (UV/MS(%)=91/86). $^1$H-NMR (400 MHz, CDCl$_3$, rotamers): δ7.33–7.01 (8H, m); 4.62 (1H, m); 4.52 and 4.46 (2H, 2s); 3.80 (1H, s); 3.45 and 3.54 (2H, 2s); 2.86 (2H, m); 2.66 (2H, m); 2.28 and 2.34 (3H, 2s); 1.98 (2H, m); 1.80 (2H, m); 1.70–1.52 (6H, m). $^{13}$C-NMR (CDCl$_3$): δ=171.7, 137.2, 135.4, 133.9, 132.9, 130.4, 129.7, 128.9, 125.7, 60.4, 52.3, 49.4, 46.5, 40.7, 29.4, 27.6, 21.2, 14.2.

Example 108

2-(4-Methoxyphenyl)-N-(4-methylbenzyl)-N-(1-cyclobutylpiperidin-4-yl)acetamide (47AKU-20)

47AKU-16 (209 mg, 0.8 mmol) was placed in 50 ml flask and 5 ml dichloromethane was added. 4-Methoxyphenylacetyl chloride (167 mg, 0.9 mmol) in 5 ml dichloromethane was added. After 5 hrs magnetic stirring the reaction mixture was concentrated on Rotavapor (40° C.). Crude product was purified by flash chromatography (0–10% methanol in dichloromethane) giving 72 mg (22%) product. Further purification by ion exchange chromatography (washout with 10% aq. NH$_4$OH (25%) in methanol) gave 67 mg (20%) 47AKU-20. Oxalate-salt was prepared from Oxalic acid (1.1 eq) in dichloromethane/heptane. TLC (10% methanol in dichloromethane): $R_f$ =0.6. HPLC-MS (Method B): M$^+$=407.3 (UV/MS(%)=93/77). $^1$H-NMR (400 MHz, CDCl$_3$, rotamers): δ=7.26–6.79 (8H, m); 4.62 (1H, m); 4.52 and 4.45 (2H, 2s); 3.79 (1H, m); 3.77 (3H, s); 3.52 and 3.45 (2H, 2s); 2.84 (2H, m); 2.66 (2H, m); 2.34 and 2.28 (3H, 2s); 1.98 (2H, m); 1.81 (2H, m); 1.72–1.51 (6H,m). $^{13}$C-NMR (CDCl$_3$): δ=172.5, 158.7, 137.0, 135.7, 130.4, 129.8, 127.4, 125.8, 114.3, 60.4, 55.5, 52.1, 49.4, 46.4, 40.6, 29.4, 27.6, 21.2, 14.2.

Example 109

(47AKU-21) 2-(4-Methoxyphenyl)-N-(4-methylbenzyl)-N-(tropin-4-yl)acetamide (47AKU-21)
4-(4-Methylbenzylamino)-tropane (47AKU-17)

4-Methylbenzylamine (607 mg, 5.0 mmol) was dissolved in 10 ml methanol and placed in 100 ml flask. Tropinone (697 mg, 5.0 mmol) in 10 ml methanol was added. Acetic acid (0.75 ml) was added until pH~5. NaCNBH$_3$ (628 mg, 10 mmol) was slowly added. Gas evolution observed. After 20 hrs magnetic stirring dichloromethane, 2M NaOH and water were added until pH~10. Phases were separated and aq. phase was then re-extracted with dichloromethane. Combined organic phases were dried over MgSO$_4$. Concentration on Rotavapor (40° C.) yielded 1.14 g crude 47AKU-17. TLC (10% methanol in dichloromethane): $R_f$ =0.4. HPLC-MS (Method A): M$^+$=245.2 (UV/MS(%)=65/96).
2-(4-Methoxyphenyl)-N-(4-methylbenzyl)-N-(tropin-4-yl)-acetamide (47AKU-21)

47AKU-17 (244 mg, 1.0 mmol) was placed in 50 ml flask and 5 ml dichloromethane was added. 4-Methoxyphenylacetyl chloride (203 mg, 1.1 mmol) in 10 ml dichloromethane was added. After 3 hrs magnetic stirring the reaction mixture was concentrated on Rotavapor (40° C.). Crude product was purified by ion exchange chromatography (washout with 10% aq. $NH_4OH$ (25%) in methanol) and flash chromatography (0–10% methanol in dichloromethane) giving 202 mg (51%) 47AKU-21. Oxalate-salt was prepared from Oxalic acid (1.1 eq) in dichloromethane/heptane. TLC (10% methanol in dichloromethane): $R_f$0.4. HPLC-MS (Method B): $M^+$=393.3 (UV/MS(%)=94/92). $^1$H-NMR (400 MHz, $CDCl_3$, isomers): δ=7.02–7.17 (6H, m); 6.78–6.87 (2H, m); 4.74 (1H, s); 4.44 (1H, s); 3.78 and 3.77 (3H, 2s); 3.68 (1H, m); 3.66 and 3.55 (3H, 2s); 2.65 (2H, m); 2.56 (2H, m); 2.32 (3H, s); 2.12–2.26 (6H, m); 2.05 (2H, m). $^{13}$C-NMR ($CDCl_3$): δ=173.2, 171.4, 158.8, 137.1, 129.7, 127.6, 126.9, 126.0, 114.4, 63.4, 60.9, 55.5, 54.6, 47.5, 41.5, 40.4, 32.8, 31.1, 27.5, 24.9, 21.2.

Example 110

N-(4-Methylbenzyl)-N-(1-methylpiperidin-4-yl)-N'-benzyl-carbamide (47AKU-22)

47AKU-5 (219 mg, 1.0 mmol) was dissolved in 5 ml dichloromethane and placed in 50 ml flask. Benzylisocyanate (160 mg, 1.2 mmol) in 5 ml dichloromethane was added. After 16 hrs magnetic stirring the reaction mixture was concentrated on Rotavapor (40° C.). Crude product was purified by flash chromatography (0–10% methanol in dichloromethane) giving 236 mg (67%) 47AKU-22. Oxalate-salt was prepared from Oxalic acid (1.1 eq) in dichloromethane/heptane. TLC (10% methanol in dichloromethane): $R_f$=0.5. HPLC-MS (Method B): $M^+$=352.3 (UV/MS(%)=100/100). $^1$H-NMR (400 MHz, $CDCl_3$): δ=7.26–7.02 (9H, m); 4.61 (1H, m); 4.41 (1H, m); 4.33 (4H, m); 2.87 (2H, m); 2.32 (3H, s); 2.25 (3H, s); 2.09 (2H, m); 1.79–1.62 (4H, m). $^{13}$C-NMR ($CDCl_3$): δ=158.6, 139.7, 137.3, 135.4, 129.8, 128.6, 127.4, 127.2, 126.2, 55.5, 52.2, 46.2, 45.8, 45.0, 30.2, 21.2.

Example 111

N-(4-Methylbenzyl)-N-(1-methylpiperidin-4-yl)-N'-phenyl carbamide (47AKU-24)

47AKU-5 (219 mg, 1.0 mmol) was dissolved in 5 ml dichloromethane and placed in 50 ml flask. Phenylisocyanate (143 mg, 1.2 mmol) in 5 ml dichloromethane was added. After 4 hrs magnetic stirring the reaction mixture was concentrated on Rotavapor (40° C.). Crude product was purified by flash chromatography (0–10% methanol in dichloromethane) giving 181 mg (54%) 47AKU-24. HCl-salt was prepared from 2M HCl/diethylether in dichloromethane/heptane. TLC (10% methanol in dichloromethane): $R_f$=0.4. HPLC-MS (Method A): $M^+$=338.3 (UV/MS(%)=100/100). $^1$H-NMR (400 MHz, $CDCl_3$): δ=7.12–7.24 (8H, m); 6.93–6.98 (1H, m); 6.26 (1H, s); 4.45 (3H, s); 2.90 (2H, d); 2.36 (3H, s); 2.28 (3H, s); 2.12 (2H, m); 1.69–1.85 (4H, m). $^{13}$C-NMR ($CDCl_3$): δ=156.1, 139.3, 137.8, 134.9, 130.1, 128.9, 126.3, 123.1, 119.9, 55.5, 52.3, 46.3, 46.2, 30.3, 21.3.

Example 112

N-Phenethyl-N-(1-methylpiperidin-4-yl)-N'-benzyl-carbamide (47AKU-25)

4-(2-Phenylethyl)amino-1-methylpiperidine (110 mg, 0.5 mmol) was dissolved in 5 ml dichloromethane and placed in 50 ml flask. Benzylisocyanate (80 mg, 0.6 mmol) in 5 ml dichloromethane was added. After 20 hrs magnetic stirring the reaction mixture was concentrated on Rotavapor (40° C.). Crude product was purified by flash chromatography (0–10% methanol in dichloromethane) giving 164 mg (84%) 47AKU-25. HCl-salt was prepared from 2M HCl/diethylether in dichloromethane/heptane. TLC (10% methanol in dichloromethane): $R_f$=0.4. HPLC-MS (Method A): $M^+$=352.3 (UV/MS(%)=100/100). $^1$H-NMR (400 MHz, $CDCl_3$): δ=7.34–7.09 (10H, m); 4.52 (1H, m); 4.35 (2H, d); 4.08 (1H, m); 3.33 (2H, t); 2.92 (2H, m); 2.82 (2H, t); 2.28 (3H, s); 2.07 (2H, m); 1.84–1.66 (4H, m). $^{13}$C-NMR ($CDCl_3$): δ=157.9, 139.8, 139.1, 129.0, 128.9, 128.8, 127.8, 127.4, 126.9, 55.7, 52.8, 46.2, 45.3, 44.8, 37.5, 30.6.

Example 113

2-Phenyl-N-(4-methoxybenzyl)-N-(1-methylpiperidin-4-yl)-acetamide (47AKU-26a)

50ELH-18 (118 mg, 0.5 mmol) was dissolved in 5 ml dichloromethane in 50 ml flask.

4-Fluorophenylacetyl chloride (104 mg, 0.6 mmol) was added. After 20 hrs stirring at room temp. mixture was concentrated on Rotavapor (40° C.). Crude product was purified by flash chromatography (0–10% methanol in dichloromethane) giving 87 mg (49%) 47AKU-26a. HCl-salt was prepared from 2M HCl/diethylether in dichloromethane/heptane. HPLC-MS (Method A): $M^+$=353.1 (UV/MS(%)=96/88).

Example 114

2-(4-Trifluoromethylphenyl)-N-(4-methoxybenzyl)-N-(1-methylpiperidin-4-yl)-acetamide (47AKU-26b)

50ELH-18 (118 mg, 0.5 mmol) was dissolved in 5 ml dichloromethane in 50 ml flask.

4-Trifluoromethylphenylacetyl chloride (134 mg, 0.6 mmol) was added. After 20 hrs stirring at room temp. mixture was concentrated on Rotavapor (40° C.). Crude product was purified by flash chromatography (0–10% methanol in dichloromethane) giving 81 mg (39%) 47AKU-26b. HCl-salt was prepared from 2M HCl/diethylether in dichloromethane/heptane. HPLC-MS (Method A): $M^+$=421.1 (UV/MS(%)=90/100).

Example 115

2-(4-Fluorophenyl)-N-(4-methoxybenzyl)-N-(1-methylpiperidin-4-yl)-acetamide (47AKU-26c)

50ELH-18 (118 mg, 0.5 mmol) was dissolved in 5 ml dichloromethane in 50 ml flask.

4-Fluorophenylacetyl chloride (104 mg, 0.6 mmol) was added. After 20 hrs stirring at room temp. mixture was concentrated on Rotavapor (40° C.). Crude product was purified by flash chromatography (0–10% methanol in dichloromethane) giving 68 mg (37%) 47AKU-26c. HCl-salt was prepared from 2M HCl/diethylether in dichloromethane/heptane. HPLC-MS (Method A): $M^+$=371.1 (UV/MS(%)=100/97).

Example 116

2-(4-Methoxyphenyl)-N-(4-methoxybenzyl)-N-(1-methylpiperidin-4-yl)-acetamide (47AKU-26d)

50ELH-18 (118 mg, 0.5 mmol) was dissolved in 5 ml dichloromethane in 50 ml flask.

4-Methoxyphenylacetyl chloride (111 mg, 0.6 mmol) was added. After 20 hrs stirring at room temp. mixture was

Example 117

2-(4-Methylphenyl)-N-(4-chlorobenzyl)-N-(1-methylpiperidin-4-yl)-acetamide (47AKU-28)

4-(4-Chlorobenzylamine)-1-methyl-piperidine (47AKU-27)

1-Methyl-4-piperidone (566 mg, 5.0 mmol) was dissolved in 10 ml methanol and placed in 100 ml flask. 4-Chlorobenzylamine (708 mg, 5.0 mmol) was added. Mixture was stirred and Acetic acid (~0.75 ml) was added until pH~5. NaCNBH$_3$ (628 mg, 10 mmol) was slowly added. Gas evolution observed. After magnetic stirring for 16 hrs methanol was partly removed on Rotavapor (40° C.). Dichloromethane, 2M NaOH and water were added until pH~10. Phases were separated and aq. phase was then re-extracted with dichloromethane. Combined organic phases were dried over MgSO$_4$. Concentration on Rotavapor (40° C.) yielded 1.14 g crude 47AKU-27. TLC (10% methanol in dichloromethane): R$_f$=0.3. HPLC-MS (Method A): M$^+$=239.1 (MS(%)=96).

2-(4-Methylphenyl)-N-(4-chlorobenzyl)-N-(1-methylpiperidin-4-yl)-acetamide (47AKU-28)

p-Tolylacetic acid (1.50 g) was dissolved in 10 ml thionylchloride and placed in 50 ml flask. Mixture was heated to reflux for 2 hrs and then concentrated on Rotavapor (40° C.).

p-Tolylacetic chloride (202 mg, 1.2 mmol) in 5 ml dichloromethane was added to 47AKU-27 (239 mg, 1.0 mmol) in 5 ml dichloromethane. After 4 hrs magnetic stirring the reaction mixture was concentrated on Rotavapor (40° C.). Crude product was purified by flash chromatography (0–10% methanol in dichloromethane) giving 104 mg (28%) 47AKU-28. HCl-salt was prepared from 2M HCl/diethylether in dichloromethane/heptane. TLC (10% methanol in dichloromethane): R$_f$=0.5. HPLC-MS (Method A): M$^+$=371.1 (UV/MS(%)=100/90). $^1$H-NMR (400 MHz, CDCl$_3$, rotamers): δ=7.34–6.99 (8H, m); 4.57 (1H, m); 4.50 and 4.44 (2H, 2s); 3.80 (1H, s); 3.55 (1H, s); 2.96 and 2.82 (2H, 2m); 2.34 (1H, m); 2.32 (3H, s); 2.24 and 2.15 (3H, 2s); 1.91 (1H, m); 1.81–1.59 (4H, m). $^{13}$C-NMR (CDCl$_3$): δ=172.5, 138.2, 136.8, 133.4, 131.8, 129.7, 129.2, 128.6, 127.4, 54.9, 51.3, 46.7, 41.3, 30.6, 28.6, 21.2.

Example 118

2-(4-Hydroxyphenyl)-N-(4-methylbenzyl)-N-(1-methylpiperidin-4-yl)-acetamide (47AKU-29)

42ELH-77 (41 mg, 0.1 mmol) was dissolved in 1 ml dry dichloromethane and placed in oven-dried 10 ml flask. Mixture was cooled to −78° C. on a dry-ice/isopropanol bath. Borontribromide (1.0 M in dichloromethane, 150 µl, 0.15 mmol) was slowly added at −78° C. Ice-bath was removed and mixture was left at room temp. for 2 hrs. Water (3 ml) and saturated NaCl (aq.) were added and aq. phase was extracted with dichloromethane, ethylacetate and n-butanol. Combined organic phases were dried over MgSO$_4$ and concentrated on Rotavapor (40° C.). Crude product was purified by flash chromatography (0–20% methanol in dichloromethane) giving 22 mg (63%) 47AKU-29. HCl-salt was prepared from 2M HCl/diethylether in dichloromethane/heptane. TLC (10% methanol in dichloromethane): R$_f$=0.3. HPLC-MS (Method A): M$^+$=353.2 (UV/MS(%)=100/100). $^1$H-NMR (400 MHz, CDCl$_3$, rotamers): δ=7.07–6.60 (8H, m); 4.48 (1H, m); 4.39 (2H, s); 3.76 and 3.66 (4H, 2bs); 3.41 (2H, s); 3.08 (2H, m); 2.49 (1H, m); 2.42 (2H, bs); 2.22 and 2.16 (3H, 2s); 1.96–1.82 (2H, m); 1.66–1.56 (1H, m). $^{13}$C-NMR (CDCl$_3$): δ=173.7, 156.0, 137.3, 134.6, 129.7, 129.6, 125.7, 125.4, 115.7, 54.4, 50.4, 46.8, 44.0, 40.5, 27.3, 20.9.

Example 119

N-Phenethyl-N-(1-methylpiperidin-4-yl)-N'-phenyl-carbamide (47AKU-30)

4-(2-Phenylethyl)amino-1-methylpiperidine (110 mg, 0.5 mmol) was dissolved in 5 ml dichloromethane and placed in 50 ml flask. Phenylisocyanate (71 mg, 0.6 mmol) in 5 ml dichloromethane was added. After 16 hrs magnetic stirring the reaction mixture was concentrated on Rotavapor (40° C.). Crude product was purified twice by flash chromatography (0–10% methanol in dichloromethane) giving 131 mg (78%) 47AKU-30. HCl-salt was prepared from 2M HCl/diethylether in dichloromethane/heptane. TLC (10% methanol in dichloromethane): R$_f$=0.4. HPLC-MS (Method A): M$^+$=338.1 (UV/MS(%)=99/100). $^1$H-NMR (400 MHz, CDCl$_3$): δ=7.36–6.93 (10H, m); 6.24 (1H, s); 4.31 (1H, m); 3.50 (2H, t); 3.20 (2H, d); 2.89 (2H, t); 2.57 (2H, m); 2.50 (3H, s); 2.26 (2H, m); 1.79 (2H, m). $^{13}$C-NMR (CDCl$_3$) δ=155.8, 139.2, 139.0, 129.4, 129.3, 128.9, 127.3, 123.2, 120.4, 54.9, 51.3, 45.5, 44.3, 37.6, 28.3.

Example 120

N-(3-Phenylpropyl)-N-(1-methylpiperidin-4-yl)-N'-benzyl-carbamide (47AKU-31)

4-(3-Phenylpropyl)amino-1-methylpiperidine(160 mg, 0.7 mmol) was dissolved in 5 ml dichloromethane and placed in 50 ml flask. Benzylisocyanate (107 mg, 0.8 mmol) in 5 ml dichloromethane was added. After 2 hrs magnetic stirring the reaction mixture was concentrated on Rotavapor (40° C.). Crude product was purified twice by flash chromatography (0–10% methanol in dichloromethane) giving 156 mg (61%) 47AKU-31. HCl-salt was prepared from 2M HCl/diethylether in dichloromethane/heptane. TLC (10% methanol in dichloromethane): R$_f$=0.3. HPLC-MS (Method A): M$^+$=366.1 (UV/MS(%)=100/100). $^1$H-NMR (400 MHz, CDCl$_3$): δ=7.34–7.07 (10H, m); 4.33 (3H, m); 4.14 (1H, m); 3.04 (2H, m); 2.89 (2H, d); 2.57 (2H, t); 2.28 (3H, s); 2.06 (2H, m); 1.87 (2H, m); 1.75–1.62 (4H, m). $^{13}$C-NMR (CDCl$_3$): δ=157.5, 141.0, 140.0, 129.0, 128.6, 128.3, 128.0, 127.6, 126.6, 55.6, 52.1, 46.3, 45.1, 41.6, 33.4, 32.2, 30.6.

Example 121

N-(3-Phenylpropyl)-N-(1-methylpiperidin-4-yl)-N'-phenyl-carbamide (47AKU-32)

4-(3-Phenylpropyl)amino-1-methylpiperidine (160 mg, 0.7 mmol) was dissolved in 5 ml dichloromethane and placed in 50 ml flask. Phenylisocyanate (95 mg, 0.8 mmol) in 5 ml dichloromethane was added. After 20 hrs magnetic stirring the reaction mixture was concentrated on Rotavapor (40° C.). Crude product was purified by flash chromatography (0–10% methanol in dichloromethane) giving 106 mg (43%) 47AKU-32. HCl-salt was prepared from 2M HCl/diethylether in dichloromethane/heptane. TLC (10% methanol in dichloromethane): R$_f$=0.3. HPLC-MS (Method A): M$^+$=352.1 (UV/MS(%)=100/100). $^1$H-NMR (400 MHz, CDCl$_3$): δ=7.35–6.95 (10H, m); 5.99 (1H, s); 4.18 (1H, m);

3.17 (2H, t); 2.91 (2H, d); 2.65 (2H, t); 2.28 (3H, s); 2.07 (2H, m); 1.97 (2H, m); 1.81–1.66 (4H, m). $^{13}$C-NMR (CDCl$_3$): δ=154.9, 141.0, 139.3, 129.2, 129.0, 129.0, 126.8, 123.1, 120.0, 55.6, 52.2, 46.2, 41.8, 33.4, 32.3, 30.6.

Example 122

2-(4-Methoxyphenyl)-2,2-ethylene-N-(4-methylbenzyl)-N-(1-methylpiperidin-4-yl)acetamide (47AKU-33)

1-(4-Methoxyphenyl)-1-cyclopropane carboxylic acid (230 mg, 1.2 mmol) was dissolved in 2 ml thionylchloride and placed in 50 ml flask. Mixture was heated to reflux for 2 hrs and then concentrated on Rotavapor (40° C.). The acid chloride (250 mg, 1.2 mmol) in 5 ml dichloromethane was added to 47AKU-5 (220 mg, 1.0 mmol) in 5 ml dichloromethane. After 2 hrs magnetic stirring the reaction mixture was concentrated on Rotavapor (40° C.). Crude product was purified twice by flash chromatography (0–10% methanol in dichloromethane) giving 201 mg (51%) 47AKU-33. HCl-salt was prepared from 2M HCl/diethylether in dichloromethane/heptane. TLC (10% methanol in dichloromethane): R$_f$=0.6. HPLC-MS (Method A): M$^+$=393.2 (UV/MS(%)=95/88).

$^1$H-NMR (400 MHz, CDCl$_3$, rotamers): δ=7.22–6.70 (8H, m); 4.44 (2H, s); 4.26 (1H, m); 3.74 (3H, s); 3.12 and 2.89 (2H, 2m); 2.51 (1H, m); 2.32 (3H, m); 2.26 (3H, s); 2.08–1.52 (4H, m); 1.36 (2H, bs); 1.15–0.95 (3H, m). $^{13}$C-NMR (CDCl$_3$) δ=172.9, 158.6, 136.6, 132.7, 129.2, 128.6, 127.9, 127.4, 114.4, 55.5, 55.1, 54.4, 45.2, 45.0, 29.8, 29.2, 21.2, 13.8.

Example 123

2-(4-Methoxyphenyl)-N-(1-phenylethyl)-N-(1-methylpiperidin-4-yl)acetamide (47AKU-37)
4-Alpha-methylbenzylamino-1-methyl-piperidine (47AKU-36)

DL-Phenylethylamine (606 mg, 5.0 mmol) was dissolved in 10 ml methanol and 1-Methyl-4-piperidone (566 mg, 5.0 mmol) in 10 ml methanol was added. Mixture was stirred and Acetic acid (~0.75 ml) was added until pH~5. NaCNBH$_3$ (628 g, 10 mmol) was slowly added. Gas evolution observed. After magnetic stirring for 20 hrs methanol was partly removed on Rotavapor (40° C.). Ethylacetate, 2M NaOH and water were added until pH~10. Phases were separated and aq. phase was then re-extracted with ethylacetate and dichloromethane. Combined organic phases were dried over MgSO$_4$. Concentration on Rotavapor (40° C.) yielded 838 mg crude 47AKU-36. TLC (10% methanol in dichloromethane): R$_f$=0.3. HPLC-MS (Method A): M$^+$=219.1 (UV/MS(%)=100/94).
2-(4-Methoxyphenyl)-N-alpha-methylbenzyl-N-(1-methylpiperidin-4-yl)acetamide (47AKU-37)

47AKU-36 (218 mg, 1.0 mmol) was dissolved in 10 ml dichloromethane and placed in 50 ml flask. 4-Methoxyphenylacetyl chloride (185 mg, 1.2 mmol) in 10 ml dichloromethane was added. After 16 hrs magnetic stirring the reaction mixture was concentrated on Rotavapor (40° C.). Crude product was purified by flash chromatography (0–10% methanol in dichloromethane) giving 256 mg (70%) 47AKU-37. HCl-salt was prepared from 2M HCl/diethylether in dichloromethane/heptane. TLC (10% methanol in dichloromethane): R$_f$=0.5. HPLC-MS (Method A): M$^+$=367.3 (UV/MS(%)=100/99).

$^1$H-NMR (400 MHz, CDCl$_3$, rotamers): δ=7.34–7.06 (7H, m); 6.84 (2H, d); 5.10 (1H, m); 3.77 (3H, s); 3.67 (2H, m); 3.17 (1H, m); 3.03–2.75 (3H, m); 2.64 (3H, s); 2.38 (2H, m); 1.77–1.05 (6H, m). $^{13}$C-NMR (CDCl$_3$): δ=172.0, 158.9, 139.9, 130.0, 129.0, 128.2, 127.1, 114.5, 55.5, 53.1, 51.4, 42.4, 41.3, 31.1, 29.5, 24.9, 18.1.

Example 124

2-(4-Methoxyphenyl)-N-(4-methylbenzyl)-N-(3-tropen-4-yl)acetamide (47AKU-39)
4-Methylbenzylimino-tropane (47AKU-38)

4-Methylbenzylamine (1.21 g, 10 mmol) and Tropinone (1.39 g, 10 mmol) were placed in 100 ml flask and dissolved in 50 ml toluene. Mixture was heated to reflux for 3 hrs and water was removed using a Dean/Stark water-separator. Crude product was concentrated on Rotavapor (40° C.) giving 47AKU-38. TLC (10% methanol in dichloromethane): R$_f$=0.3. $^1$H-NMR (400 MHz, CDCl$_3$, isomers): 7.20–7.09 (4H, m); 4.47 (1H, m); 3.81 (1H, s); 3.42 (1H, m); 3.31 (1H, m); 2.77–2.56 (2H, m); 2.47 and 2.41 (3H, 2s); 2.33 and 2.31 (3H, 2s); 2.27–1.97 (4H, m); 1.69–1.54 (2H, m).
2-(4-Methoxyphenyl)-N-(4-methylbenzyl)-N-(3-tropen-4-yl)acetamide (47AKU-39)

47AKU-38 (242 mg, 1.0 mmol) was dissolved in 5 ml dichloromethane and placed in 50 ml flask. 4-Methoxyphenylacetyl chloride (185 mg, 1.2 mmol) in 10 ml dichloromethane was added. After 16 hrs magnetic stirring the reaction mixture was concentrated on Rotavapor (40° C.). Crude product was purified by flash chromatography (0–10% methanol in dichloromethane) giving 69 mg (18%) 47AKU-39. HCl-salt was prepared from 2M HCl/diethylether in dichloromethane/heptane. TLC (10% methanol in dichloromethane): R$_f$=0.4. HPLC-MS (Method A): M$^+$=391.2 (UV/MS(%)=91/86).

$^1$H-NMR (400 MHz, CDCl$_3$, rotamers): δ=7.22–6.82 (8H, m); 5.41 (1H, bs); 4.71–4.52 (2H, m); 3.78 (3H, s); 3.68 (2H, m); 3.44–3.24 (2H, m); 2.72–2.36 (5H, m); 2.32 (3H, s); 2.25–2.00 (2H, m); 1.80–1.54 (2H, m). $^{13}$C-NMR (CDCl$_3$): δ=170.8, 158.7, 137.4, 134.9, 130.1, 129.3, 128.9, 126.9, 114.2, 59.0, 58.0, 55.5, 49.5, 46.3, 39.7, 35.9, 33.8, 29.7, 21.3.

Example 125

2-Phenyl-2-ethyl-N-(4-methylbenzyl)-N-(1-methylpiperidin-4-yl)acetamide (47AKU-40)

2-Phenylbutyric acid (197 mg, 1.2 mmol) was dissolved in 2 ml thionylchloride and placed in 50 ml flask. Mixture was heated to reflux for 2 hrs and then concentrated on Rotavapor (50° C.). The acid chloride (1.2 mmol) in 5 ml dichloromethane was added to 47AKU-5 (158 mg, 0.72 mmol) in 5 ml dichloromethane. After 20 hrs magnetic stirring the reaction mixture was concentrated on Rotavapor (40° C.). Crude product was purified by flash chromatography (0–10% methanol in dichloromethane) giving 196 mg (74%) 47AKU-40. HCl-salt was prepared from 2M HCl/diethylether in dichloromethane/heptane. TLC (10% methanol in dichloromethane): R$_f$=0.5. HPLC-MS (Method A): M$^+$=365.4 (UV/MS(%)=99/100). $^1$H-NMR (400 MHz, CDCl$_3$, rotamers): δ=7.32–6.98 (8H, m); 4.77 (1H, bs); 4.50 (1H, d); 4.29 (1H, d); 3.43 and 3.21 (3H, 2m); 2.72 (2H, m); 2.62 (3H, s); 2.43 (1H, m); 2.32 (3H, s); 2.2 (3H, m); 2.04 (2H, m); 1.67 (3H, m); 0.92–0.72 (3H, m). $^{13}$C-NMR (CDCl$_3$): δ=174.7, 139.9, 137.3, 135.2, 129.7, 129.0, 127.8, 127.3, 125.8, 54.5, 51.6, 49.4, 46.0, 43.8, 28.9, 26.7, 26.3, 21.2, 12.7.

Example 126

2-(4-Methoxyphenyl)-N-(1-indanyl)-N-(1-methylpiperidin-4-yl)acetamide (47AKU-43)
4-(1-Indanamino)-1-methyl-piperidine (47AKU-42)

1-Aminoindane (666 mg, 5.0 mmol) was dissolved in 10 ml methanol and placed in 100 ml flask. 1-Methyl-4-piperidone (566 mg, 5.0 mmol) in 10 ml methanol was added. Mixture was stirred and Acetic acid (~0.75 ml) was added until pH~5. NaCNBH$_3$ (628 g, 10 mmol) was slowly added. Gas evolution observed. After magnetic stirring for 16 hrs methanol was partly removed on Rotavapor (40° C.). Dichloromethane, 2M NaOH and water were added until pH~10. Phases were separated and aq. phase was then re-extracted with ethylacetate and dichloromethane. Combined organic phases were dried over MgSO$_4$. Concentration on Rotavapor (40° C.) yielded 1.06 g 47AKU-42. TLC (10% methanol in dichloromethane): R$_f$=0.3. HPLC-MS (Method A): M$^+$=231.1 (UV/MS(%)=72/91).

2-(4-Methoxyphenyl)-N-(1-indanyl)-N-(1-methylpiperidin-4-yl)acetamide (47AKU-43)

47AKU-42 (230 mg, 1.0 mmol) was dissolved in 10 ml dichloromethane and placed in 50 ml flask. 4-Methoxyphenylacetyl chloride (185 mg, 1.2 mmol) in 10 ml dichloromethane was added. After 16 hrs magnetic stirring the reaction mixture was concentrated on Rotavapor (40° C.). Crude product was purified by flash chromatography (0–10% methanol in dichloromethane) giving 194 mg (51%) 47AKU-43. HCl-salt was prepared from 2M HCl/diethylether in dichloromethane/heptane. TLC (10% methanol in dichloromethane): R$_f$=0.5. HPLC-MS (Method A): M$^+$=379.2 (UV/MS(%)=94/90).

Example 127

(47AKU-44)N-(4-Methylbenzyl)-N-(1-methylpiperidin-4-yl)-N'-(4-methoxybenzyl)-carbamide (47AKU-44)

47AKU-5 (219 mg, 1.0 mmol) was dissolved in 5 ml dichloromethane and placed in 50 ml flask. 4-Methoxybenzylisocyanate (196 mg, 1.2 mmol) in 10 ml dichloromethane was added. After 16 hrs magnetic stirring the reaction mixture was concentrated on Rotavapor (40° C.). Crude product was purified by flash chromatography (0–10% methanol in dichloromethane) giving 192 mg (50%) 47AKU-44. HCl-salt was prepared from 2M HCl/diethylether in dichloromethane/heptane. TLC (10% methanol in dichloromethane): R$_f$=0.3. HPLC-MS (Method A): M$^+$=382.3 (UV/MS(%)=100/94). $^1$H-NMR (400 MHz, CDCl$_3$): δ=7.10 (4H, m); 6.98 (2H, m); 6.76 (2H, m); 4.58 (1H, t); 4.45 (1H, m); 4.33 (2H, s); 4.25 (2H, d); 3.76 (3H, s); 2.97 (2H, m); 2.34 (3H, s); 2.32 (3H, s); 2.24 (2H, m); 1.78 (4H, m). $^{13}$C-NMR (CDCl$_3$): δ=158.9, 158.5, 137.3, 135.2, 131.8, 129.8, 128.8, 126.2, 114.1, 55.5, 55.4, 51.7, 45.8, 45.7, 44.5, 29.7, 21.2.

Example 128

2-(3,4-dimethoxyphenyl)-N-(4-methylbenzyl)-N-(1-methylpiperidin-4-yl)acetamide (47AKU-45)

3,4-Dimethoxyphenylbutyric acid (235 mg, 1.2 mmol) was dissolved in 2 ml thionylchloride and placed in 50 ml flask. Mixture was heated to reflux for 2 hrs and then concentrated on Rotavapor (50° C.). The acid chloride (1.2 mmol) in 5 ml dichloromethane was added to 47AKU-5 (219 mg, 1.0 mmol) in 10 ml dichloromethane. After 16 hrs magnetic stirring the reaction mixture was concentrated on Rotavapor (40° C.). Crude product was purified by flash chromatography (0–10% methanol in dichloromethane) giving 129 mg (33%) 47AKU-45. HCl-salt was prepared from 2M HCl/diethylether in dichloromethane/heptane. TLC (10% methanol in dichloromethane): R$_f$=0.4. HPLC-MS (Method A): M$^+$=397.4 (UV/MS(%)=98/89). $^1$H-NMR (400 MHz, CDCl$_3$, rotamers): δ=7.17–6.60 (7H, m); 4.75 (1H, m); 4.51 (2H, s); 3.83 (3H, s); 3.79 (3H, s); 3.53 (2H, s); 3.27 (2H, d); 2.65 (2H, t); 2.58 (3H, s); 2.32 (3H, s); 2.24 (2H, m); 1.72 (2H, d). $^{13}$C-NMR (CDCl$_3$): δ=172.8, 149.3, 148.3, 137.4, 135.0, 129.8, 127.4, 125.8, 121.0, 112.2, 111.6, 56.2, 56.1, 54.6, 49.6, 46.7, 44.0, 40.9, 27.0, 21.2.

Example 129

2-(3,4-Methylenedioxyphenyl)-N-(4-methylbenzyl)-N-(1-methylpiperidin-4-yl)acetamide (47AKU-46)

3,4-Methylenedioxyphenylacetic acid (216 mg, 1.2 mmol) was dissolved in 2 ml thionylchloride and placed in 50 ml flask. Mixture was heated to reflux for 2 hrs and then concentrated on Rotavapor (50° C.). The acid chloride (1.2 mmol) in 5 ml dichloromethane was added to 47AKU-5 (219 mg, 1.0 mmol) in 10 ml dichloromethane. After 2 hrs magnetic stirring the reaction mixture was concentrated on Rotavapor (40° C.). Crude product was purified by flash chromatography (0–10% methanol in dichloromethane) giving 188 mg (49%) product. Further purification by ion exchange chromatography (washout with 10% aq. NH$_4$OH (25%) in methanol) yielded 149 mg (39%) 47AKU-46. HCl-salt was prepared from 2M HCl/diethylether in dichloromethane/heptane. TLC (10% methanol in dichloromethane): R$_f$=0.4. HPLC-MS (Method A): M$^+$=381.2 (UV/MS(%)=96/95). $^1$H-NMR (400 MHz, CDCl$_3$, rotamers): δ=7.17–7.02 (4H, m); 6.77–6.51 (3H, m); 5.91 and 5.93 (2H, 2s); 4.70 (1H, m); 4.52 and 4.49 (2H, 2s); 3.51 (2H,.s); 3.26 (2H, d); 2.49 (3H, s); 2.33 (3H, s); 2.14–1.66 (6H, m) $^{13}$C-NMR (CDCl$_3$): δ=172.5, 148.1, 146.8, 137.3, 135.1, 129.8, 128.6, 125.8, 121.9, 109.4, 108.5, 101.2, 54.8, 50.2, 46.7, 44.6, 41.1, 27.7, 21.2.

Example 130

2-(4-Methoxyphenyl)-N-(4-methylbenzyl)-N-(1-t-butylpiperidin-4-yl)-acetamide (47AKU-49)
1-t-Butyl-4-piperidone (47AKU-47)

1-Benzyl-4-piperidone (1.89 g, 10 mmol) was dissolved in 15 ml acetone. Methyliodide (0.90 ml, 15 mmol) was slowly added over 5 min. After 2 hrs magnetic stirring additional Methyliodide (1.8 ml, 30 mmol) was added. After 1 hr magnetic stirring 20 ml diethyl-ether was added. Crude product was collected by filtration and washed with acetone/diethylether. White crystals were dried under vacuum giving 806 mg quartenary salt. TLC (10% methanol in dichloromethane): R$_f$=0.7. Partly dissolved salt in 5 ml water was added to 50° C. hot mixture of t-Butylamine (120 mg, 1.6 mmol) and Potassiumcarbonate (32 mg, 0.22 mmol) in 3 ml ethanol. The resulting mixture was stirred and heated to reflux (~80° C.) for 1 hr. After cooling water (20 ml) and dichloromethane (20 ml) were added. Phases were separated and aq. phase was re-extracted with dichloromethane and ethylacetate. Combined organic phases were dried over MgSO$_4$ and concentrated on Rotavapor (40° C.) giving 496 mg 47AKU-47. TLC (10% methanol in dichloromethane): R$_f$=0.3. $^1$H-NMR (400 MHz, CDCl$_3$): δ=2.82 (4H, t); 2.41 (4H, t); 1.12 (9H, s). $^{13}$C-NMR (CDCl$_3$): δ=210.2, 54.3, 46.4, 42.4, 26.6. Crude product contained ~25% ($^1$H-NMR) starting material (1-Benzyl-4-piperidone).

4-(4-Methylbenzylamino)-1-t-butyl-piperidine (47AKU-48)

4-Methylbenzylamine (268 mg, 2.2 mmol) was dissolved in 5 ml methanol and placed in 50 ml flask. 47AKU-47 (305 mg, 2.0 mmol) in 5 ml methanol was added. Acetic acid (0.3 ml) was added until pH~5. NaCNBH$_3$ (250 mg, 4.0 mmol) was slowly added. Gas evolution observed. After 4 hrs magnetic stirring dichloromethane, 2M NaOH and water were added until pH~10. Phases were separated and aq. phase was then re-extracted with dichloromethane and ethylacetate. Combined organic phases were dried over MgSO$_4$. Concentration on Rotavapor (40° C.) yielded 556 mg crude 47AKU-48. TLC (20% methanol in dichloromethane): R$_f$=0.4. HPLC-MS (Method A): M$^+$=261.2 (MS(%)=57).

2-(4-Methoxyphenyl)-N-(4-methylbenzyl)-N-(1-t-butylpiperidin-4-yl)-acetamide (47AKU-49)

47AKU-48 (556 mg, 2.1 mmol) was placed in 50 ml flask and 5 ml dichloromethane was added. 4-Methoxyphenylacetyl chloride (739 mg, 4.0 mmol) in 10 ml dichloromethane was added. After 4 hrs magnetic stirring the reaction mixture was concentrated on Rotavapor (40° C.). Crude product was purified by flash chromatography (0–10% methanol in dichloromethane) giving 124 mg (15%) product. Further purification by ion exchange chromatography (washout with 10% aq. NH$_4$OH (25%) in methanol) gave 91 mg (11%) 47AKU-49. HCl-salt was prepared from 2M HCl/diethylether in dichloromethane/heptane. TLC (10% methanol in dichloromethane): R$_f$=0.5. HPLC-MS (Method A): M$^+$=409.4 (UV/MS(%)=100/90). $^1$H-NMR (400 MHz, CDCl$_3$): δ=7.11 (4H, m); 7.03 (2H, d); 6.79 (2H, d); 4.78 (1H, m); 4.56 (2H, s); 3.76 (3H, s); 3.53 (2H, s); 3.43 (2H, m); 2.63 (2H, m); 2.47 (2H, m); 2.31 (3H, s); 1.74 (2H, d); 1.36 (9H, s). $^{13}$C-NMR (CDCl$_3$): δ=173.0, 158.8, 137.1, 135.3, 129.8, 129.7, 127.0, 125.8, 114.3, 55.6, 55.5, 49.8, 46.5, 46.4, 40.5, 26.7, 25.1, 21.2.

Example 131

N-(4-Methylbenzyl)-N-(1-methylpiperidin-4-yl)-N'-phenylethyl-carbamide (58AKU-1)

47AKU-5-2 (219 mg, 1.0 mmol) was dissolved in 5 ml dichloromethane and placed in 50 ml flask. Phenethylisocyanate (177 mg, 1.2 mmol) in 5 ml dichloromethane was added. After 6 hrs magnetic stirring the reaction mixture was concentrated on Rotavapor (40° C.). Crude product was purified by flash chromatography (0–15% methanol in dichloromethane) giving 134 mg (37%) 58AKU-1. HCl-salt was prepared from 2M HCl/diethylether in dichloromethane/heptane. TLC (10% methanol in dichloromethane): R$_f$=0.5. HPLC-MS (Method A): M$^+$=366.3 (UV/MS(%)=99/96). $^1$H-NMR (400 MHz, CDCl$_3$): δ=7.21–6.97 (9H, m); 4.33 (1H, m); 4.26 (1H, m); 4.21 (2H, s); 3.39 (2H, q); 2.85 (2H, m); 2.67 (2H, t); 2.31 (3H, s); 2.24 (3H, s); 2.06 (2H, m); 1.73–1.57 (4H, m). $^{13}$C-NMR (CDCl$_3$): δ=158.7, 139.5, 137.0, 135.4, 129.7, 128.8, 128.6, 126.3, 126.1, 55.6, 52.2, 46.2, 45.8, 42.2, 36.4, 30.2, 21.2.

Example 132

N-Phenylethyl-N-(1-methylpiperidin-4-yl)-N'-phenethyl-carbamide (58AKU-2)

4-(2-Phenylethyl)amino-1-methylpiperidine (131 mg, 0.6 mmol) was dissolved in 5 ml dichloromethane and placed in 50 ml flask. Phenethylisocyanate (103 mg, 0.7 mmol) in 5 ml dichloromethane was added. After 4 hrs magnetic stirring the reaction mixture was concentrated on Rotavapor (45° C.). Crude product was purified by flash chromatography (0–10% methanol in dichloromethane) giving 198 mg (90%) 58AKU-1. HCl-salt was prepared from 2M HCl/diethylether in dichloromethane/heptane. TLC (10% methanol in dichloromethane): R$_f$=0.3. HPLC-MS (Method A): M$^+$=366.3 (UV/MS(%)=100/100). $^1$H-NMR (400 MHz, CDCl$_3$): δ=7.33–7.16 (8H, m); 7.01 (2H, m); 4.23 (1H, t); 4.04 (1H, m); 3.47 (2H, q); 3.17 (2H, t); 2.89 (2H, m); 2.78 (2H, t); 2.66 (2H, t); 2.28 (3H, s); 2.05 (2H, m); 1.79–1.59 (4H, m). $^{13}$C-NMR (CDCl$_3$): δ=157.8, 139.6, 139.0, 129.0, 128.9, 128.8, 126.8, 126.7, 55.7, 52.5, 46.2, 44.6, 42.0, 37.3, 36.4, 30.5.

Example 133

N-(4-Methylbenzyl)-N-(1-t-butylpiperidin-4-yl)-N'-(4-methoxybenzyl)carbamide (58AKU-3)

47AKU-5-2 (404 mg, 1.6 mmol) was dissolved in 5 ml dichloromethane and placed in 50 ml flask. 4-Methoxybenzylisocyanate (326 mg, 2.0 mmol) in 5 ml dichloromethane was added. After 20 hrs magnetic stirring the reaction mixture was concentrated on Rotavapor (45° C.). Crude product was purified three times by flash chromatography (0–20% methanol in dichloromethane and 0–30% methanol in ethylacetate) giving 155 mg (23%) 58AKU-3. HCl-salt was prepared from 2M HCl/diethylether in dichloromethane/heptane. TLC (10% methanol in dichloromethane): R$_f$=0.3. HPLC-MS (Method A): M$^+$=424.2 (UV/MS(%)=92/83). $^1$H-NMR (400 MHz, CDCl$_3$): δ=7.10 (4H, m); 6.99 (2H, m); 6.76 (2H, m); 4.53 (1H, m); 4.35 (3H, s); 4.26 (2H, d); 3.77 (3H, s); 3.09 (2H, m); 2.32 (3H, s); 2.22 (2H, m); 1.81–1.54 (4H, m); 1.06 (9H, s). $^{13}$C-NMR (CDCl$_3$): δ=158.9, 158.6, 137.1, 135.6 131.9, 129.7, 128.8, 126.2, 114.0, 62.6, 55.5, 53.0, 45.9, 45.7, 44.5, 31.0, 26.3, 21.2.

Example 134

2-(4-Ethoxyphenyl)-N-(4-methylbenzyl)-N-(1-methylpiperidin-4-yl)acetamide (58AKU-4)

4-Ethoxyphenylacetic acid (270 mg, 1.5 mmol) was dissolved in 2 ml thionylchloride and placed in 50 ml flask. Mixture was heated to reflux for 2 hrs and then concentrated on Rotavapor (45° C.). The acid chloride (1.5 mmol) in 5 ml dichloromethane was added to 47AKU-5-2 (262 mg, 1.2 mmol) in 5 ml dichloromethane. After 20 hrs magnetic stirring the reaction mixture was concentrated on Rotavapor (40° C.). Crude product was purified by flash chromatography (0–10% methanol in dichloromethane) giving 272 mg (60%) 58AKU-4. HCl-salt was prepared from 2M HCl/diethylether in dichloromethane/heptane. TLC (10% methanol in dichloromethane): R$_f$=0.4. HPLC-MS (Method A): M$^+$=381.2 (UV/MS(%)=98/91). $^1$H-NMR (400 MHz, CDCl$_3$): δ=7.17–6.99 (6H, m); 6.82–6.76 (2H, m); 4.73 (1H, m); 4.48 (2H, s); 3.98 (2H, q); 3.52 (2H, s); 3.22 (2H, d); 2.61 (2H, t); 2.54 (3H, s); 2.32 (3H, s); 2.14 (2H, s); 1.71 (2H, d): 1.38 (3H, t). $^{13}$C-NMR (CDCl$_3$): δ=172.9, 158.2, 137.3, 135.0, 129.9, 129.8, 126.8, 125.8, 114.9, 63.7, 54.6, 49.8, 46.7, 44.1, 40.6, 27.2, 21.2, 15.0.

Example 135

2-(4-Butoxyphenyl)-N-(4-methylbenzyl)-N-(1-methylpiperidin-4-yl)acetamide (58AKU-5)

4-Butoxyphenylacetic acid (317 mg, 1.5 mmol) was dissolved in 2 ml thionylchloride and placed in 50 ml flask. Mixture was heated to reflux for 2 hrs and then concentrated on Rotavapor (45° C.). The acid chloride (1.5 mmol) in 5 ml dichloromethane was added to 47AKU-5-2 (262 mg, 1.2 mmol) in 5 ml dichloromethane. After 20 hrs magnetic stirring the reaction mixture was concentrated on Rotavapor (40° C.). Crude product was purified by flash chromatography (0–10% methanol in dichloromethane) giving 230 mg (47%) 58AKU-5. HCl-salt was prepared from 2M HCl/diethylether in dichloromethane/heptane. TLC (10% methanol in dichloromethane): $R_f$=0.5. HPLC-MS (Method A): $M^+$=409.2 (UV/MS(%)=98/93). $^1$H-NMR (400 MHz, CDCl$_3$): δ=7.15–6.96 (6H, m); 6.78 (2H, m); 4.74 (1H, m); 4.48 (2H, s); 3.91 (2H, t); 3.52 (2H, s); 3.27 (2H, d); 2.72 (2H, t); 2.58 (3H, s); 2.32 (3H, s); 2.23 (2H, m); 1.72 (4H, d); 1.45 (2H, m); 0.95 (3H, t). $^{13}$C-NMR (CDCl$_3$): δ=173.0, 158.4, 137.3, 135.0, 129.8, 126.6, 125.8, 115.0, 67.9, 54.4, 49.5, 46.7, 43.8, 40.6, 31.5, 26.8, 21.2, 19.4, 14.0.

Example 136

2-(4-i-Propoxyphenyl)-N-(4-methylbenzyl)-N-(1-methylpiperidin-4-yl)acetamide (58AKU-6)

47AKU-29-2 (245 mg, 0.7 mmol) was dissolved in 10 ml dimethylformamide and placed in 50 ml flask. KOH (196 mg, 3.5 mmol) and Isopropylbromide (200 μl, 2.1 mmol) were added. Mixture was heated to 50° C. and stirred for 24 hrs. After cooling water and ethylacetate were added. Phases were separated and aq. phase was then re-extracted with dichloromethane. Combined organic phases were washed with brine, dried over MgSO$_4$ and concentrated on Rotavapor (40° C.) giving 188 mg. Crude product was purified by flash chromatography (0–10% methanol in dichloromethane) yielding 136 mg (49%) 58AKU-6. HCl-salt was prepared from 2M HCl/diethylether in dichloromethane/heptane. TLC (10% methanol in dichloromethane): $R_f$=0.3. HPLC-MS (Method B): $M^+$=395 (UV/MS(%)=95/91). $^1$H-NMR (400 MHz, CDCl$_3$, rotamers): δ=7.23–7.01 (6H, m); 6.79 (2H, m); 4.60 (1H, m); 4.51 (1H, m); 4.44 (1H, s); 3.77 (1H, s); 3.52 (1H, s); 2.83 (2H, m); 2.76 (2H, m); 2.28 and 2.34 (3H, 2s); 2.19 and 2.22 (3H, 2s); 2.05 (1H, m); 1.86–1.55 (4H, m); 1.32 (6H, d). $^{13}$C-NMR (CDCl$_3$): δ=172.6, 157.0, 137.1, 135.6, 129.8, 129.7, 125.8, 116.2, 70.1, 55.3, 51.6, 46.6, 46.1, 40.8, 29.6, 22.3, 21.2.

Example 137

Receptor Selection and Amplification (R-SAT) Assays.

The functional receptor assay, Receptor Selection and Amplification Technology (R-SAT), was used (with minor modifications from that previously described U.S. Pat. No. 5,707,798) to screen compounds for efficacy at the 5-HT2A receptor. Briefly, NIH3T3 cells were grown in 96 well tissue culture plates to 70–80% confluence. Cells were transfected for 12–16 hours with plasmid DNAs using superfect (Qiagen Inc.)as per manufacture's protocols. R-SAT's were generally performed with 50 ng/well of receptor and 20 ng/well of Beta-galactosidase plasmid DNA. All receptor and G-protein constructs used were in the pSI mammalian expression vector. (Promega Inc) as described in U.S. Pat. No. 5,707,798. The 5HT2A receptor gene was amplified by nested PCR from brain cDNA using the oligodeoxynucleotides based on the published sequence (see Saltzman et. al. Biochem. Biophys. Res. Comm. 181:1469–78 (1991)). Large-scale transfections, cells were transfected for 12–16 hours, then trypsinized and frozen in DMSO. Frozen cells were later thawed, plated at 10,000–40,000 cells per well of a 96 well plate that contained drug. With both methods, cells were then grown in a humidified atmosphere with 5% ambient CO2 for five days. Media was then removed from the plates and marker gene activity was measured by the addition of the beta-galactosidase substrate ONPG (in PBS with 5% NP-40). The resulting colorimetric reaction was measured in a spectrophotometric plate reader (Titertek Inc.) at 420 nM. All data were analyzed using the computer program XLFit (IDBSm). Efficacy is the percent maximal repression compared to repression by a control compound (ritanserin in the case of 5HT2A). pIC50 is the negative of the log(IC50), where IC50 is the calculated concentration in Molar that produces 50% maximal repression. The results obtained for several compounds of the invention are presented in Table 4, below.

TABLE 4

Efficiency and pIC50 of Compounds at the 5-HT2A Receptor Compared to Ritanserin

| Compound | Percent Efficacy | pIC50 |
|---|---|---|
| 26HCH17 | 94 | 8.3 |
| 26HCH65 | 103 | 8.2 |
| 26HCH66-05 | 126 | 8.1 |
| 26HCH79-5 | 94 | 8.2 |
| 26HCH79-6 | 83 | 8.3 |
| 26HCH79-10 | 102 | 7.8 |
| 26HCH71B | 124 | 7.9 |
| 42ELH45 | 108 | 9.0 |
| 50ELH27 | 108 | 8.7 |
| 47AKU-7 | 120 | 8.1 |
| 42ELH80 | 122 | 8.5 |
| 42ELH79 | 110 | 8.5 |
| 42ELH91 | 108 | 8.0 |
| 42ELH85 | 118 | 7.8 |
| 42ELH75 | 109 | 8.3 |
| 47AKU-12 | 112 | 8.1 |
| 47AKU-8 | 113 | 8.1 |
| 47AKU-22 | 117 | 7.9 |
| 47AKU-21 | 117 | 7.9 |
| 47AKU-20 | 120 | 8.0 |
| 50ELH8 | 129 | 7.8 |
| 50ELH68 | 96 | 8.4 |
| 50ELH65 | 92 | 7.9 |
| 47AKU-44 | 112 | 8.5 |
| 57MBT12B | 75 | 7.7 |
| 58AKU-4 | 110 | 9.6 |
| 58AKU-3 | 111 | 8.1 |
| 58AKU-5 | 99 | 9.5 |
| 58AKU-6 | 101 | 9.8 |
| 57MBT54B | 95 | 7.9 |
| 50ELH95B | 119 | 8.0 |
| 50ELH93E | 72 | 8.1 |
| 50ELH93D | 58 | 7.8 |
| 50ELH93A | 106 | 8.7 |
| 63ELH1A | 104 | 8.3 |
| 50ELH89 | 111 | 9.7 |
| 63ELH20 | 95 | 9.0 |
| 57MBT70-8D | 119 | 7.7 |
| 57MBT70-5D | 105 | 8.4 |
| 57MBT70-4D | 98 | 8.5 |
| 57MBT70-3D | 87 | 8.9 |
| 57MBT70-2D | 105 | 8.2 |
| 57MBT70-1D | 120 | 7.9 |
| 63ELH21 | 100 | 8.5 |
| 57MBT62B | 119 | 7.9 |
| 57MBT70-6E | 115 | 8.0 |

Example 138

Selectivity Profile for 2-(4-Methoxyphenyl)-N-(4-methylbenzyl)-N-(1-methylpiperidin-4-yl)acetamide hydrochloride The R-SAT assay (described above in example 137) was used to investigate the selectivity of 2-(4-Methoxyphenyl)-

N-(4-methylbenzyl)-N-(1-methylpiperidin-4-yl)acetamide hydrochloride. The results from a broad profiling of this compound at a variety of receptors are reported in Table 4 below. NR means No Response, i.e. the compound investigated showed no effect at the receptor studied.

TABLE 4

Selectivity of 2-(4-Methoxyphenyl)-N-(4-methylbenzyl)-N-(1-methylpiperidin-4-yl)acetamide

| RECEPTOR | ASSAY | pEC50/pIC50 |
| --- | --- | --- |
| $5\text{-}HT_{1A}$ | agonist | NR |
| | antagonist | NR |
| $5\text{-}HT_{1B}$ | agonist | NR |
| | antagonist | NR |
| $5\text{-}HT_{1D}$ | agonist | NR |
| | antagonist | NR |
| $5\text{-}HT_{1E}$ | agonist | NR |
| | antagonist | NR |
| $5\text{-}HT_{1F}$ | agonist | NR |
| | antagonist | NR |
| $5\text{-}HT_{2A}$ | agonist | NR |
| | inverse agonist | 8.8 |
| $5\text{-}HT_{2B}$ | agonist | NR |
| | inverse agonist | 6.9 |
| $5\text{-}HT_{2C}$ | agonist | NR |
| | inverse agonist | 7 |
| $5\text{-}HT_4$ | agonist | NR |
| | inverse agonist | NR |
| $5\text{-}HT_6$ | agonist | NR |
| | Inv. Agonist | 6.8 |
| 5-HT7 | agonist | NR |
| | inverse agonist | 6.9 |
| m1 | agonist | NR |
| | antagonist | NR |
| m2 | agonist | NR |
| | antagonist | NR |
| m3 | agonist | NR |
| | antagonist | NR |
| m4 | agonist | NR |
| | antagonist | NR |
| m5 | agonist | NR |
| | antagonist | NR |
| D1 | agonist | NR |
| | antagonist | NR |
| D2 | agonist | NR |
| | antagonist | NR |
| D3 | agonist | NR |
| | antagonist | NR |
| D5 | agonist | NR |
| | antagonist | NR |
| Histamine 1 | agonist | NR |
| | Inv. agonist | NR |
| Histamine 2 | agonist | NR |
| | antagonist | NR |
| Histamine 3 | agonist | NR |
| | antagonist | NR |
| alpha-1A(a/c) | agonist | NR |
| | antagonist | NR |
| alpha-1B | agonist | NR |
| | In. Agonist | NR |
| alpha-2A | agonist | NR |
| | antagonist | NR |
| alpha-2B | agonist | NR |
| | antagonist | NR |
| alpha-2C | agonist | NR |
| | antagonist | NR |
| beta 1 | agonist | NR |
| | antagonist | NR |
| beta 2 | agonist | NR |
| | antagonist | NR |
| endothelinB | agonist | NR |
| CCK-A | agonist | NR |
| NK-1 | agonist | NR |
| Vasopressin1A | agonist | NR |
| K-opiod | agonist | NR |

Example 139

In Vivo Pharmacology of 2-(4-Methoxyphenyl)-N-(4-methylbenzyl)-N-(1-methylpiperidin-4-yl) acetamide hydrochloride(AC-90,179)

Methods

Animals and Apparatus

Instruments) were used for rat experiments (details on startle apparatus and measures, see Male Non-Swiss Albino mice and male Sprague-Dawley rats (Harlan Sprague-Dawley) were housed (4 mice/cage; 2 rats/cage) in rooms with temperature and humidity controlled and water and food (Harlan Teklad) freely available. Mice were kept on a 12-hr light:dark cycle, whereas rats were kept on a 12-hr reverse light:dark cycle. For locomotor and observation experiments in mice, plastic 20×20×30 cm activity cages were equipped with photocell beams (AccuScan Instruments). Startle chambers (San Diego Instruments) were used for rat experiments (for details on startle apparatus and measures, see Mansbach et al., (1988) *Psychopharmacology* 94:507–14).

Procedure

Observation for Head Twitches

Mice were treated with 2.5 mg/kg DOI i.p. Five min later, mice were treated with AC-90179 s.c. and placed into activity cages. Ten min later, mice were observed using a repeated sampling technique. Each mouse was observed for 10 sec and rated for presence (1) or absence (0) of head twitch behavior for a total of 6 observations in 15 min and a total head twitch score of 0–6. Each dose combination was tested in a separate group of animals (n=8) and the experimenter was blind to drug conditions. Head twitch scores were averaged followed by analysis of variance (ANOVA) and post-hoc Dunnett's t-test comparisons.

Locomotor Activity

For hyperactivity experiments, mice were treated with 0.3 mg/kg dizocilpine or 3.0 mg/kg d-amphetamine i.p. 15 min before the session. Five minutes after the pretreatment, mice were treated with AC-90179 s.c. and placed into the activity cages. For spontaneous activity, AC-90179 was administered alone. Locomotor data were collected during a 15 min session without habituation in a lit room. Each dose combination was tested in a separate group of animals (n=8). Distance traveled (cm) was calculated and averaged followed by ANOVA and post-hoc Dunnett's t-test comparisons.

Startle Testing

Rats were tested and groups (n=10) matched for levels of startle reactivity and prepulse inhibition (PPI; see Mansbach et al., (1988) *Psychopharmacology* 94:507–14). Two days later, test sessions started and consisted of a 5-min acclimation period with a constant background noise (65 dB), followed by 60 presentations of acoustic stimuli to measure acoustic startle responses. The 60 trials consisted of: twenty two 40-ms presentations of a 120 dB broadband pulse, ten 20-ms presentations of each prepulse intensity (68, 71, 77 dB) 100 ms prior to a 40-msec presentation of a 120 dB broadband pulse, and 8 NOSTIM trials in which no stimuli were delivered in order to assess general motor activation in the rats. Thirty min before testing, rats were treated with sterile water (s.c.), risperidone (1.0 mg/kg, i.p.), or AC-90179 (s.c.). Five min later, rats were administered DOI (0.5 mg/kg, s.c.) or 0.9% saline (s.c.). One-week later, rats were administered the same pretreatment drug or vehicle and crossed over to receive the treatment opposite to that they received the previous week. Startle magnitudes and percent PPI for the three prepulse intensities were calculated as described elsewhere (Bakshi, et al., (1994) *J. Pharmacol.*

*Exp. Ther.* 271:787–94) and ANOVAs with repeated measures performed.

Results

To further characterize the clinical utility of a selective 5-HT2A receptor inverse agonist as a novel antipsychotic agent, AC-90179 was tested in head twitch, locomotor and pre pulse inhibition behavioral models. DOI-treated (2.5 mg/kg, i.p., 15 min) mice exhibited an average head twitch score of 2.6 (±0.3, S.E.M.). AC-90179 (0.1–30 mg/kg, s.c., 10 min) caused a dose-related decrease in DOI-induced head-twitches with a minimum effective dose of 1 mg/kg and with higher doses completely eliminating head twitch behavior (FIG. 2A).

In the locomotor experiments (FIG. 2B), mice traveled an average of 794 cm (±122 S.E.M.) after vehicle administration. Dizocilpine (0.3 mg/kg, i.p., 15 min) and d-amphetamine (3.0 mg/kg, i.p., 15 min) caused increases in distance traveled with averages of 2625 cm (±312) and 3367 cm (±532), respectively. AC-90179 (0.3–10 mg/kg, s.c., 10 min) attenuated the hyperactivity induced by dizocilpine, but not by d-amphetamine. The minimum effective dose against dizocilpine was 1 mg/kg, whereas AC-90179 reduced spontaneous locomotor activity only at the highest dose tested (30 mg/kg).

Figure 2:
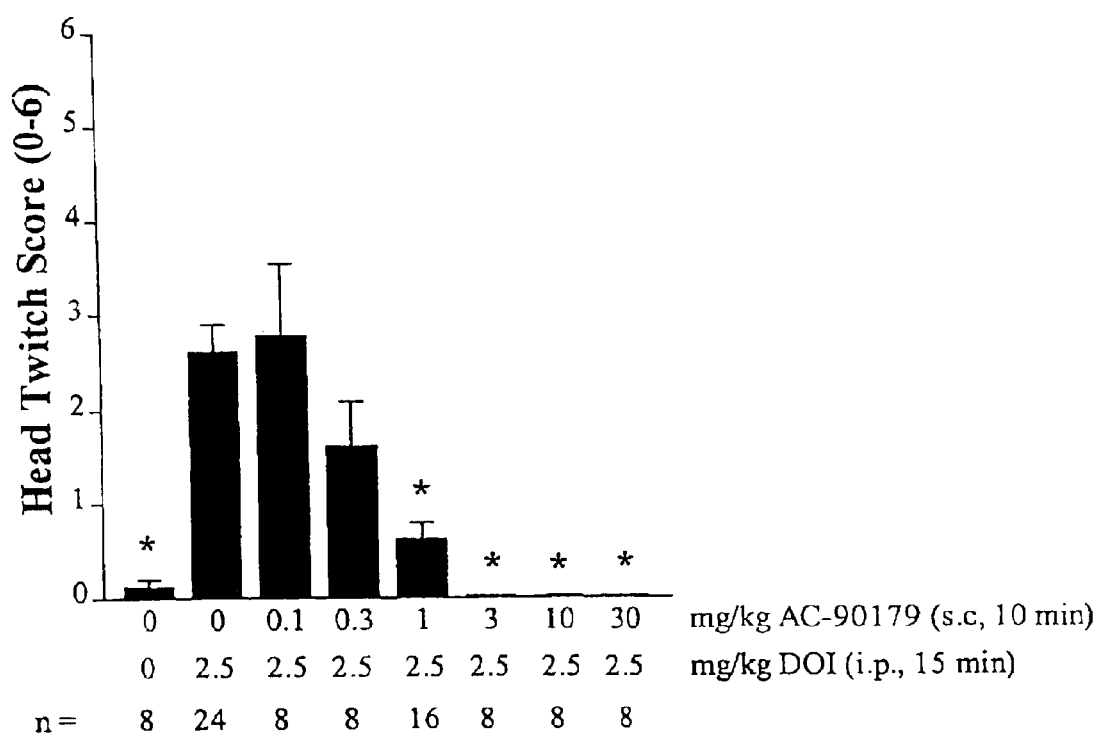
FIGS. 2–4 are graphic representations of in vivo pharmacology data obtained in mice with 2-(4-methoxyphenyl)-N-(4-methylbenzyl)-N-(1-methylpiperidin-4-yl)acetamide hydrochloride.
Figure 3:
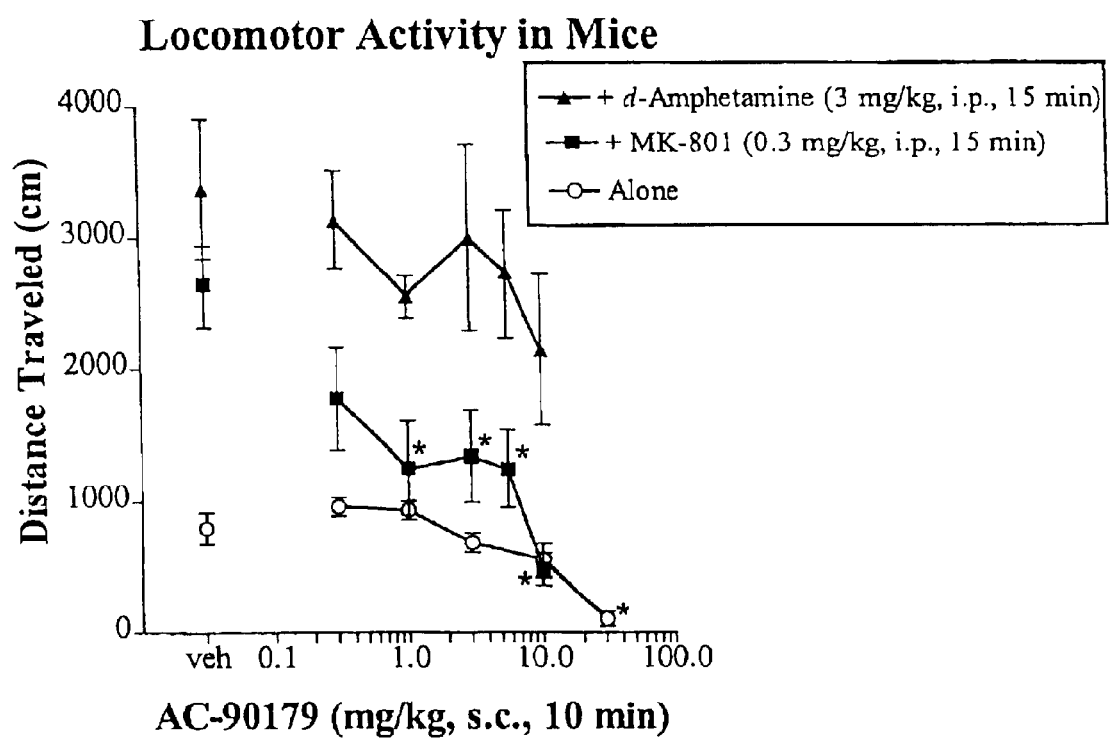
Figure 4:
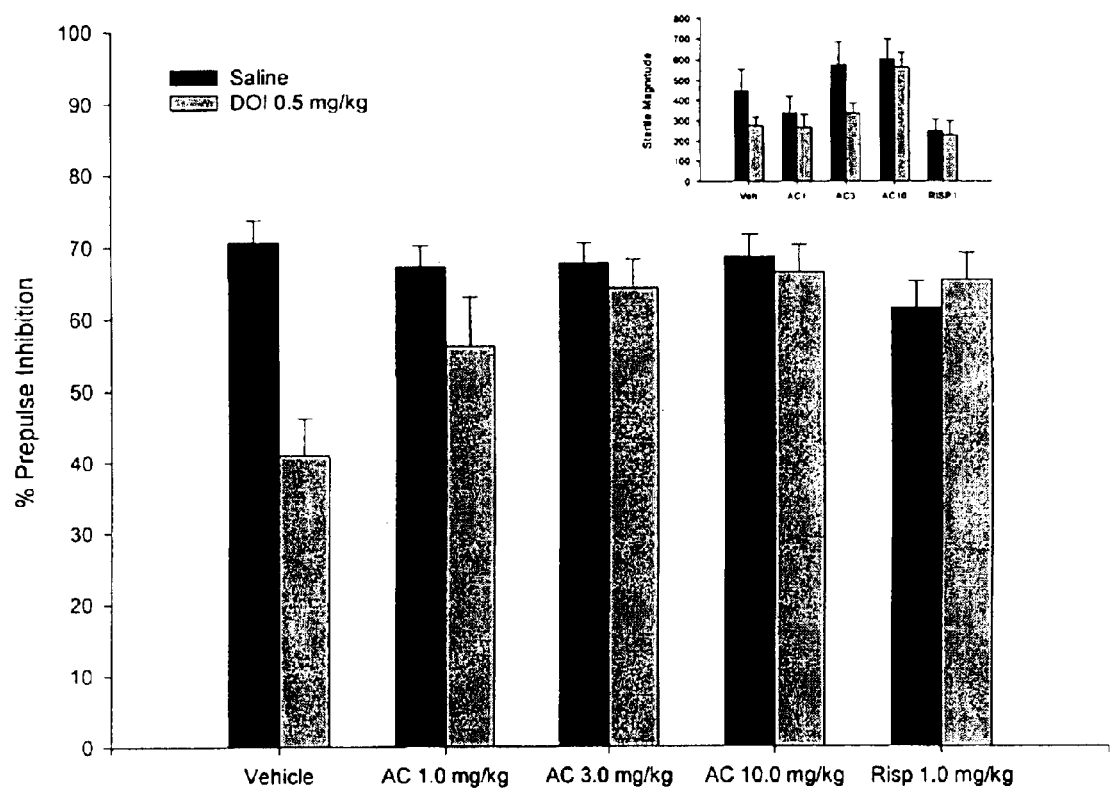

The 3-way repeated measures ANOVA on the PPI data from the AC-90179 groups revealed an overall effect of treatment [F(1,37)=27.73, p=<0.01] and a treatment by pretreatment interaction [F(3,37)=8.22, p<0.01] (FIG. 2C). DOI significantly disrupted PPI, and AC-90179 was effective in restoring this disruption especially at the higher doses. AC-90179 did not affect PPI on its own, with no significant effect of pretreatment (p>0.05) on percent PPI. Risperidone was used as a positive control because previous studies in our laboratory have suggested that it is effective in blocking the PPI-disruptive effects of DOI. The 3-way repeated measures ANOVA on the PPI data from the risperidone group also revealed a significant effect of treatment [F(1,18)=14.08, p<0.01] and a treatment by pretreatment interaction [F(1,18)=24.48, p<0.01). As predicted, risperidone was also effective in restoring PPI in DOI-treated rats. Risperidone also had no effect on PPI by itself, as evidenced by a lack of a pretreatment effect (p>0.05). Since there were no significant interactions with prepulse intensity, the data were collapsed across the three prepulse is intensities for graphical purposes.

Since there was a significant pretreatment by treatment interaction, pair-wise 2-way repeated measures ANOVAs were conducted on the saline- and DOI-treated groups. In the vehicle-treated rats, there was no effect of AC-90179 (p>0.025) or risperidone (p>0.025) on PPI. In the DOI-treated groups, there were significant effects of AC-90179 [F(3,37)=5.68, p<0.01] and risperidone [F(1,18)=16.73, p<0.01) on percent PPI.

The 3-way repeated measures ANOVA on startle magnitude from the AC-90179 groups revealed a significant effect of pretreatment [F(3,37)=2.89, p=0.048) and treatment [F(1.37)=10.27, p<0.01] on startle magnitude, but no treatment by pretreatment interaction (p>0.05; FIG. 1, panel C inset). Risperidone, on the other hand, had no effect on startle magnitude (p>0.05).

Example 140

In Vivo Pharmacology of Additional Compounds
The Effect of Various Compounds on Head Twitch Behavior in Mice Treated with DOI was Observed as Described Above in Example 139. The Results are Summarized Below in Table 5.

The effect of various compounds on head twitch behavior in mice treated wth DOI was observed as described in Example 139. Animals received 0.1–30 mg/kg of the compound indicated via subcutaneous injection. MED indicates the minimum effective dose at which a statistically significant reduction in head twitching score (described above) was observed. MED minimum effective dose in vivo.

TABLE 5

Comparison Of Analogs For Their Ability To Attenuate DOI-Induced Head Twitches In Mice.

| Compound | MED |
|---|---|
| 26HCH17 | 30 |
| 44ELH45 | 30 |
| 50ELH27 | 1 |
| 42ELH80 | ≦10 |
| 42ELH79 | ≦10 |
| 47AKU-7 | ≦10 |
| 42ELH85 | ≦10 |
| 47AKU-8 | ≦10 |
| 47AKU-12 | ≦10 |
| 47AKU-13 | ≦10 |
| 42ELH91 | >10 |
| 42ELH90 | ~10 |
| 47AKU-20 | ≦10 |
| 47AKU-19 | >10 |
| 47AKU-22 | ≦10 |
| 47AKU-21 | >10 |
| 42ELH75 | ≦10 |
| 47AKU-11 | ~10 |
| 47AKU-14 | ≦10 |
| 47AKU-18 | >10 |
| 50ELH6 | ≦10 |
| 47AKU-33 | ≦10 |
| 47AKU-25 | >10 |
| 50ELH65 | ≦10 |
| 50ELH68 | ≦10 |
| 47AKU-49 | ≦10 |
| 47AKU-44 | ≦10 |
| 58AKU-4 | ≦10 |
| 58AKU-5 | ≦1 |
| 50ELH93A | ≦10 |
| 58AKU-6 | ≦10 |
| 63ELH20 | ≦10 |
| 63ELH21 | ≦10 |

MED = minimum effective dose in vivo.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The disclosures of all references cited herein are incorporated by reference in their entireties.

We claim:
1. A compound of formula (I)

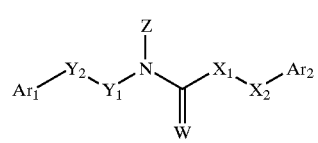

wherein
Z is

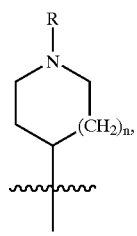

wherein R is a lower alkyl group, wherein said lower alkyl group is a methyl; and n is 1;
$X_1$ is methylene, vinylene, or an NH or N(lower alkyl) group; and $X_2$ is methylene; or, when $X_1$ is methylene or vinylene, $X_2$ is methylene or a bond; or when $X_1$ is methylene, $X_2$ is O, S, NH, or N(lower alkyl) or a bond;
$Y_1$ is methylene and $Y_2$ is methylene, vinylene, ethylene, propylene, or a bond; or
$Y_1$ is a bond and $Y_2$ is vinylene; or
$Y_1$ is ethylene and $Y_2$ is O, S, NH, or N(lower alkyl);
$Ar_1$ and $Ar_2$ independently are unsubstituted or substituted aryl or heteroaryl groups, provided that $Ar_1$ and $Ar_2$ are not simultaneously unsubstituted phenyl; and
W is oxygen; or
a pharmaceutically acceptable salt or prodrug thereof.

2. A compound of formula (I)

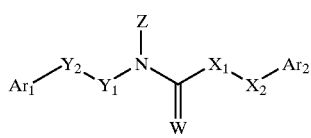

wherein
Z is

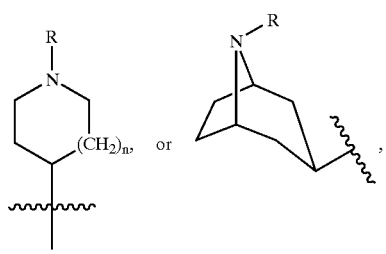

wherein R is a hydrogen, a cyclic or straight-chained or branched acyclic organyl group, a lower hydroxyalkyl group, a lower aminoalkyl group, or an aralkyl or heteroaralkyl group; and n is 1;
$X_1$ is an NH, and $X_2$ is methylene;
$Y_1$ is methylene and $Y_2$ is methylene, vinylene, ethylene, propylene, or a bond; or
$Y_1$ is a bond and $Y_2$ is vinylene; or
$Y_1$ is ethylene and $Y_2$ is O, S, NH, or N(lower alkyl);
$Ar_1$ and $Ar_2$ independently are unsubstituted or substituted aryl or heteroaryl groups, provided that $Ar_1$ and $Ar_2$ are not simultaneously unsubstituted phenyl; and
W is oxygen; or
a pharmaceutically acceptable salt or prodrug thereof.

3. A compound of formula (I)

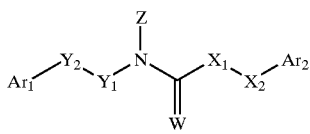

wherein
Z is

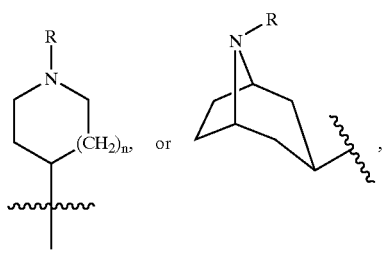

wherein R is a hydrogen, a cyclic or straight-chained or branched acyclic organyl group, a lower hydroxyalkyl group, a lower aminoalkyl group, or an aralkyl or heteroaralkyl group; and n is 1;
$X_1$ is methylene, vinylene, or an NH or N(lower alkyl) group; and
$X_2$ is methylene, or, when $X_1$ is methylene or vinylene, $X_2$ is methylene or a bond; or when $X_1$ is methylene, $X_2$ is O, S, NH, or N(lower alkyl) or a bond;
$Y_1$ is methylene and $Y_2$ is a bond;
$Ar_1$ and $Ar_2$ independently are unsubstituted or substituted aryl or heteroaryl groups, provided that $Ar_1$ and $Ar_2$ are not simultaneously unsubstituted phenyl; and
W is oxygen; or
a pharmaceutically acceptable salt or prodrug thereof.

4. A compound of formula (I)

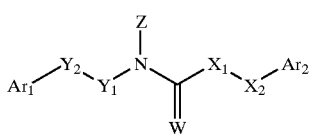

wherein
Z is

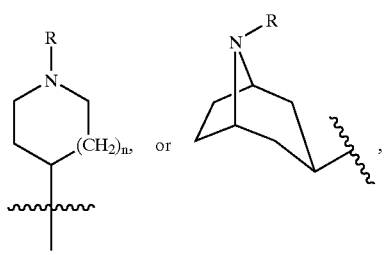

wherein R is a hydrogen, a cyclic or straight-chained or branched acyclic organyl group, a lower hydroxyalkyl group, a lower aminoalkyl group, or an aralkyl or heteroaralkyl group; and n is 1;
$X_1$ is methylene, vinylene, or an NH or N(lower alkyl) group; and $X_2$ is methylene, or, when $X_1$ is methylene or vinylene, $X_2$ is methylene or a bond; or when $X_1$ is methylene, $X_2$ is O, S, NH, or N(lower alkyl) or a bond;

$Y_1$ is methylene and $Y_2$ is methylene, vinylene, ethylene, propylene, or a bond; or $Y_1$ is a bond and $Y_2$ is vinylene; or $Y_1$ is ethylene and $Y_2$ is O, S, NH, or N(lower alkyl);

$Ar_1$ is a 4-haloaryl, wherein said aryl is phenyl and said halo is a fluoro;

$Ar_2$ is a 4-substituted aryl, wherein said aryl is phenyl, and said phenyl is substituted with a lower alkoxy group, wherein the alkyl group of said lower alkoxy group is an isobutyl; and W is oxygen; or a pharmaceutically acceptable salt or prodrug thereof.

5. A tartrate salt of a compound of formula (I)

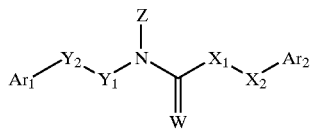

I wherein
Z is

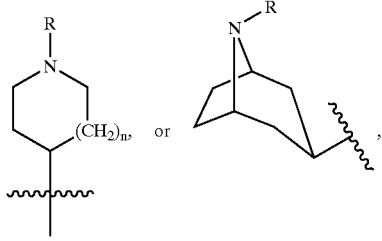

wherein R is a hydrogen, a cyclic or straight-chained or branched acyclic organyl group, a lower hydroxyalkyl group, a lower aminoalkyl group, or an aralkyl or heteroaralkyl group; and n is 1;

$X_1$ is methylene, vinylene, or an NH or N(lower alkyl) group; and $X_2$ is methylene, or, when $X_1$ is methylene or vinylene, $X_2$ is methylene or a bond; or when $X_1$ is methylene, $X_2$ is O, S, NH, or N(lower alkyl) or a bond;

$Y_1$ is methylene and $Y_2$ is methylene, vinylene, ethylene, propylene, or a bond; or $Y_1$ is a bond and $Y_2$ is vinylene; or $Y_1$ is ethylene and $Y_2$ is O, S, NH, or N(lower alkyl);

$Ar_1$ and $Ar_2$ independently are unsubstituted or substituted aryl or heteroaryl groups, provided that $Ar_1$ and $Ar_2$ are not simultaneously unsubstituted phenyl; and W is oxygen.

* * * * *